United States Patent
Koide et al.

(10) Patent No.: US 12,312,392 B2
(45) Date of Patent: May 27, 2025

(54) METHODS AND COMPOSITION INVOLVING THERMOPHILIC FIBRONECTIN TYPE III (FN3) MONOBODIES

(71) Applicant: The University of Chicago, Chicago, IL (US)

(72) Inventors: Shohei Koide, Chicago, IL (US); Shun-Ichi Tanaka, Chicago, IL (US); Akiko Koide, Chicago, IL (US)

(73) Assignee: The University of Chicago, Chicago, IL (US)

( * ) Notice: Subject to any disclaimer, the term of this patent is extended or adjusted under 35 U.S.C. 154(b) by 0 days.

(21) Appl. No.: 18/312,100

(22) Filed: May 4, 2023

(65) Prior Publication Data
US 2024/0018216 A1 Jan. 18, 2024

Related U.S. Application Data

(62) Division of application No. 15/733,530, filed as application No. PCT/US2019/018866 on Feb. 21, 2019, now Pat. No. 11,680,091.

(60) Provisional application No. 62/634,616, filed on Feb. 23, 2018.

(51) Int. Cl.
C07K 14/78 (2006.01)
C40B 40/10 (2006.01)

(52) U.S. Cl.
CPC ............. *C07K 14/78* (2013.01); *C40B 40/10* (2013.01)

(58) Field of Classification Search
None
See application file for complete search history.

(56) References Cited

U.S. PATENT DOCUMENTS

| | | |
|---|---|---|
| 6,180,341 B1 | 1/2001 | Iverson et al. |
| 6,673,901 B2 | 1/2004 | Koide |
| 6,703,199 B1 | 3/2004 | Koide |
| 6,818,418 B1 | 11/2004 | Lipovsek et al. |
| 7,119,171 B2 | 10/2006 | Koide |
| 7,153,661 B2 | 12/2006 | Koide |
| 7,556,925 B2 | 7/2009 | Koide et al. |
| 7,598,352 B2 | 10/2009 | Koide |
| 8,263,350 B2 | 9/2012 | Koide et al. |
| 9,885,050 B2 | 2/2018 | Koide et al. |
| 11,680,091 B2 * | 6/2023 | Koide ............. C07K 14/78 514/9.3 |
| 2002/0025317 A1 | 2/2002 | Leung et al. |
| 2002/0090607 A1 | 7/2002 | Fields et al. |
| 2002/0197694 A1 | 12/2002 | Shao |
| 2003/0027209 A1 | 2/2003 | Huse |
| 2003/0170615 A1 | 9/2003 | Ustav et al. |
| 2004/0005540 A1 | 1/2004 | Petrenko et al. |
| 2004/0018570 A1 | 1/2004 | Sedivy et al. |
| 2004/0058400 A1 | 3/2004 | Holliger et al. |
| 2007/0196274 A1 | 8/2007 | Sun |
| 2007/0264234 A1 | 11/2007 | Sayers et al. |
| 2009/0087445 A1 | 4/2009 | Freund et al. |
| 2010/0227913 A1 | 9/2010 | Lyakhov et al. |
| 2010/0298541 A1 * | 11/2010 | Wu ............. A61P 9/10 530/350 |
| 2010/0311094 A1 | 12/2010 | Mui et al. |
| 2011/0289625 A1 | 11/2011 | Chen et al. |
| 2013/0096058 A1 | 4/2013 | Baca et al. |
| 2014/0057807 A1 | 2/2014 | Loew et al. |
| 2014/0141994 A1 | 5/2014 | Wu et al. |
| 2014/0377776 A1 | 12/2014 | Salafsky |
| 2015/0218251 A1 | 8/2015 | Chuang et al. |
| 2016/0024191 A1 | 1/2016 | Koide |
| 2018/0208678 A1 | 7/2018 | Koide |

FOREIGN PATENT DOCUMENTS

| | | |
|---|---|---|
| WO | WO 01/64942 | 9/2001 |
| WO | WO 02/04523 | 1/2002 |
| WO | WO 2004/039845 | 5/2004 |
| WO | WO 2008/031098 | 3/2008 |
| WO | WO 08/066752 | 5/2008 |
| WO | WO 2009/062170 | 5/2009 |
| WO | WO 2010/028214 | 3/2010 |
| WO | WO 2017/015119 | 1/2017 |

OTHER PUBLICATIONS

Spaete, Richard R. et al., "Human cytomegalovirus strain towne glycoprotein b is processed by proteolytic cleavage." Virology (1988) 167(2) p. 207-225.*

Lowe, Derek; "Not alphafold's fault" Blog "In the pipeline" entry of Sep. 7, 2022.*

"Together." The Merriam-Webster.Com Dictionary, www.merriam-webster.com/dictionary/together?src=search-dict-hed. Accessed Mar. 17, 2021.

Abbas et al. *Cellular and Molecular Immunology*. Maarssen-Netherlands, Netherlands, Elsevier Gezondheidszorg, 2007, p. 80, p. 91-92.

Appleton et al., "Comparative structural anaylysis of Erbin PDZ domain and the first PDZ domain of ZO-1. Insights into the determinants of PDZ domain specificity," *J Biol Chem*, 281:22312-22320, 2006.

Asian et al., "Engineered single-chain dimeric streptavidins with an unexpected strong preference for biotin-4-fluorescein," *Proc Natl Acad Sci US A* 102:8507-12, 2005.

Baird et al., "Circular permutation and receptor insertion within green fluorescent proteins," *Proc Natl Acad Sci US A*, 96:11241-6, 1999.

(Continued)

*Primary Examiner* — Fred H Reynolds

(74) *Attorney, Agent, or Firm* — Norton Rose Fulbright US LLP

(57) ABSTRACT

The current application describes various compositions and methods for the production of FN3-based binding proteins with improved stability properties. Aspects of the disclosure relate to polypeptides comprising a variant fibronectin type III (FN3) domain from *Sulfolobus tokodaii* or *Pyrococcus horikoshii* comprising one or more amino acid substitutions or insertions in a loop region of FN3, in a non-loop region of FN3, or in both.

12 Claims, 18 Drawing Sheets

Specification includes a Sequence Listing.

(56) References Cited

OTHER PUBLICATIONS

Batori et al., "Exploring the potential of the of the monobody scaffold: effects of loop elongation on the stability of a fibronectin type III domain," *Protein Eng*, 15:1015-20, 2002.
Beebe et al. "Determination of the Binding Specificity of the SH2 Domains of Protein Tyrosine Phosphatase SHP-1 through the Screening of a Combinatorial Phosphotyrosyl Peptide Library." *Biochemistry* 2000, 39 (43), pp. 13251-60.
Berglund et al. "The Epitope Space of the Human Proteome." *Protein Science* 2008, 17(4), 606-613.
Binz et al., "Engineered proteins as specific binding reagents," *Curr Opin Biotechnol*, 16:459-69, 2005.
Binz et al., "Engineering novel binding proteins from nonimmunoglobulin domains," *Nat. Biotechnol*, 23:1257-1268, 2005.
Birrane et al., "Novel mode of ligand recognition the Erbin PDZ domain," *J Biol Chem.*, 278:1399-1402, 2003.
Blagoev et al., "A proteomics strategy to elucidate functional protien-protein interactions applied to EGF signaling," *Nat. Biotechnol.*, 21:315-318, 2003.
Blasioli et al. "Definition of the Sites of Interaction between the Protein Tyrosine Phosphatase SHP-1 and CD22." *Journal of Biological Chemistry* 1999, 274(4), pp. 2303-2307.
Boder et al., "Directed evolution of antibody fragments with monovalent femtomolar antigen-binding affinity," *Proc Natl Acad Sci.* 2000, 97:10701-5.
Boder et al., "Yeast surface display for directed evolution of protein expression, affinity, and stability," *Methods Enzymol*, 328: 430-44, 2000.
Boder et al., "Yeast surface display for screening combinatorial polypeptide libraries," *Nat Biotechnol*, 15: 553-7, 1997.
Bogan, "Anatomy of hot spots in protein interfaces," *J Mot Biol*, 280:1-9, 1998.
Bork et al., "Proposed acquisition of an animal protein domain by bacteria," *Proc. Natl. Acad. Sci. USA*, 89:8990-8994, 1992.
Bornscheuer et al., "Engineering the third wave of biocatalysis" Nature, 2012, 485:185-194.
Carr et al., "Backbone dynamics of homologous fibronectin type III cell adhesion domains from fibronectin and tenascin," *Structure*, 5:949-959, 1997.
Chen et al., "Enzyme engineering for nonaqueous solvents: random mutagenesis to enhance activity of subtilisin E in polar organic media." Biotechnology (NY.), 1991, 9: 1073-1077.
Chen-Goodspeed et al., "Enhancements, Relaxation and Reversal of the Stereoselectivity for Phosphotriesterase by Rational Evolution of Active Site Residues", Biochemistry, 2001, 40: 1332-1339.
Chou et al., "A simple apparatus for generating stretched polyacrylamide gels, yielding uniform alignment of proteins and detergent micelles," *J Biomol NMR*, 21:377-82, 2001.
Chou et al., "Study of conformational rearrangement and refinement of structural. Homology models by the use of heteronuclear dipolar couplings," *J Biomol NMR* 2000, 18:217-27.
Davids et al., "Strategies for the discovery and engineering of enzymes for biocatalysis" Curr. Opin. Chem. Biol., 2013, 17:215-220.
Decanniere et al., A single domain anti-body in a complex with RNase A: non-canonical loop structures nanomolar affinity using two CDR loops. *Structure Fold Des*, 7:361-70.
Dickinson et al., "Crystal structure of the tenth type III cell adhesion module of human fibronectin," *J Mot Biol*, 236:1079-1092, 1994.
Dieckman et al., "High throughput methods for gene cloning and expression," *Protein Expr Purif*, 25:1-7, 2002.
Dong et al., "Molecular forceps from cominatorial libraries prevent prevent the farnesylation of Ras by binding to its carboxyl terminus," *Chemistry and Biology*, 6:133-141, 1999.
Erickson, "Stretching fibronectin" J Muscle Res. Cell Motility, 2002, 23(5-6):575-580.
Fan et al., "Biosensors based on binding-modulated donor-acceptor distances," *Trends Biotechnol.*, 23:186-92, 2005.
Fellouse et al., "Molecular recognition by a binary code," *J Mot Biol*, 348:1153-1162. 2005.
Fellouse et al., "Synthetic antibodies from a four-amino-acid code: a dominant role for tyrosine in antigen recognition," *Proc. Natl Acad Sci US A*, 101:12467-72, 2004.
Ferrer et al., "Directed evolution of PDZ variants to generate high-affinity detection reagents," *Protein Eng Des Set*, 18:165-173, 2005.
Fuh et al., "Analysis of PDZ domain-ligand interactions using carboxyl-terminal phage display," *J. Biol. Chem.*, 275:21486-91, 2000.
Gilbreth et al., "A Dominant Conformational Role for Amino Acid Diversity in Minimalist Protein-Protein Interfaces" l., 2008, 381:407-418, J. Mol. Biol.
Gilbreth et al., "Isoform-specific monobody inhibitors of small ubiquitin-related modifiers engineered using structure-guided library design" Proc Natl. Acad. Sei. U.S.A., 2011, 108:7751-7756.
Goldsmith et al., "Directed enzyme evolution: beyond the low-hanging fmit" Curr. Opin. Struct. Biol., 2012, 22:406-412.
Grebien et al., "Targeting the SH2-Kinase Interface in Bcr-Abl Inhibits Leukemogenesis" Cell, 2011, 147:306-319.
Hogrefe et al., "A bacteriophage lambda vector for the cloning and expression of immunoglobulin Fab fragments on the surface of filamentous phage," *Gene*, 128:119-26, 1993.
Hosse et al., "A new generation of protein display scaffolds for molecular recognition," *Protein Sci*, 15:14-27, (2006).
Howes, L. "Deepmind ai predicts protein structures", *C&ENews*, 2020.
Huang et al., "A peptide tag system for facile purification and single-molecule immobilization," *Biochemistry*, 48: 11834-11836, 2009.
Huang et al., "Confirmation specific affinity purifications using engineered binding proteins: Application to the estrogen receptor," *Protein Expr Purif*, 2005.
Huang et al., "Design of protein function leaps by directed domain interface evolution," *Proc Natl Acad Sci USA*, 105:6578-83, 2008.
Huang et al., "IH, 13C, 15N NMR backbone assignments of 37kDa surface antigen OspC from Borrelia burgdorferi," *J Biomol NMR*, 14:283-284, 1999.
International Search Report and Written Opinion issued in Corresponding PCT Application No. PCT/US2019/018866, dated May 8, 2019.
International Search Report and Written Opinion issued in International Patent Application No. PCT/US16/42516, dated Dec. 27, 2016.
Ishii et al., "Controlling residual dipolar couplings in high-resolution NMR of protiens by strain induced alignment in a gel," *J Biomol NMR*, 21:141-151, 2001.
Iwakura et al., "Effects of the length of a glycine linker connecting the N-and C-termini of a circularly permuted dihydrofolate reductase," *Protein Eng*, 11:707-13, 1998.
Jacobs et al., "FN3 Domain Engineering", Protein Engineering, Kaumaya (Ed.), 2012.
Jones et al., "A quantative protein interaction network for the ERbB receptors using protein microarrays," *Nature*, 439:168-174, 2006.
Kaplan et al. "Solid-Phase Synthesis and Characterization of Carcinoembryonic Antigen (CEA) Domains." *The Journal of Peptide Research* 2009, 52(4), pp. 249-260.
Karatan et al., "Molecular recognition properties of FN3 monobodies that bind the Src SH3 domain," *Chem. Biol.*, 11:835-844, 2004.
Kessels et al. "Specificity and affinity motifs of Grb2-SH2-lignad interactions," *Proc Natl Acad Sci US A*, 99:8524-9, 2002.
Kohda et al., "Solution structure and ligand-binding site of the carboxy-terminal SH3 domain of GRB2," *Structure*, 2:1029-40, 1994.
Kohno et al., "A new general method for the biosynthesis of stabel isotope-enriched peptides using a decahistidine-tagged ubiquitin fusion system: an application to the production of mastoparan-X uniformly enriched with 15N and 15N/13C," *J Biomol NMR*, 12:109-121, 1998.
Koide et al., "Design of single-layer beta-sheets without a hydrophobic core," *Nature*, 403:456-460, 2000.

(56) References Cited

OTHER PUBLICATIONS

Koide et al., "High affinity single-domain binding proteins with a binary-code interface," *Proc. Natl. Acad. Sci*, 104:6632-6637, 2007.
Koide et al. "Monobodies:antibody mimics based on the scaffold of fibronectin type III domain," 35:95-109, 2007, Methods Mol. Biol.
Koide et al., "Stabilization of a fibronectin type III domain by the removal of unfavorable electrostatic interactions on the protein surface," *Biochemistry*, 40:20326-33, 2001.
Koide et al., "Teaching an old scaffold new tricks: Monobodies constmcted using alternative surfaces ofthe FN3 scaffold" 2012, 415:393-405, J. Mol. Biol.
Koide et al., The fibronectin type III domain as a scaffold for novel binding proteins, *J* 284:1141-1151, 1998, J. Mol. Biol.
Kojima et al., "Importance of terminal residues on circularly permutated *Escherichia coli* alkaline phosphatase with high specific activity," *J Biosci Bioeng*, 100:197-202, 2005.
Kunkel et al., "Rapid and efficient site-directed mutagenesis without phenotypic selection," *Methods Enzymol*, 154:367-382, 1987.
Laura et al., "The Erbin PDZ domain binds with high affinity and specificity to the carboxyl termini of delta-catenin and ARVCF," *J Biol Chem*, 277:12906-12914, 2002.
Law, Brian. *Immunoassay, a practical guide*. Abingdon-United Kingdom, United Kingdom, Taylor & Francis, 2005, table of contents only.
Lo Conte et al., "The atomic structure of protein-protein recognition sites," 285:2177-2199, 1999, J. Mol. Biol.
Looger et al., "Computational design of receptor and sensor proteins with novel functions," *Nature*, 423:185-90, 2003.
Lu et al., "Function of WW domains as phosphoserine- or phosphothreonine-binding modules," *Science* 283:1325-8, 1999.
Main et al., The three-dimensional structure of the tenth type III cell adhesion module of fibronectin: an insight into RGD-mediated interactions, *Cell*, 71:671-678, 1992.
Mak et al., "Computational enzyme design: transitioning from catalytic proteins to enzymes" Curr. Opin. Struct. Biol., 2014, 27:87-94.
Martinez et al., "Thermodynamic analysis of alpha-spectrin SH3 and two of its circular permutants with different loop lengths: discerning the reasons for rapid folding in proteins," *Biochemistry* 38:549-59, 1999.
Miyawaki et al., "Dynamic and quantitative Ca2+ measurements using improved cameleons," *Proc Natl Acad Sci US A*, 96:2135-40, 1999.
Miyawaki et al., "Fluorescent indicators for Ca2+ based on green fluorescent proteins and calmodulin," *Nature* 1997, 388:882-7.
Murphy et al., "Substrates for cell adhesion prepared via active site-directed immobilization of a protein domain," *Langmuir*, 20:1026-1030, 2004.
NCBI reference sequence WP_156014442, uploaded May 2021.
Nguyen et al., "Evolutionary optimization of fluorescent proteins for antracellular FRET," *Nat Biotechnol*, 23:355-60, 2005.
Nioche et al., "Crystal Structures of the SH2 domain of Grb2: highlight on the binding of a new high-affinity inhibitor," *J Mot Biol*, 315:1167-77, 2002.
Nourry et al., "PDZ domain proteins: plug and play!," *Sci STKE*, RE7, 2003.
Ohnishi et al., "Solution Confirmation and Amyloid-like Fibril Formation of a Polar Peptide Derived from a 13-Sheet,", 301:477-489, 2000, J. Mol. Biol.
Olson et al., "Design, expression and stability of a diverse protein library based on human fibronectin type III domain," *Protein Science*, 16:476-484, 2007.
Ostermeier et al., "Engineering allosteric protein switches by domain insertion," *Protein Eng Des Set*, 18:359-64, 2005.
Osuna et al., "Improving a circularly permuted TEM-1 beta-lactamase by directed evolution," *Protein Eng*, 15:463-70, 2002.
Ottiger et al., "Measurement of J and dipolar couplings from simplified two dimensional NMR spectra," *J Magn Reson*, 131:373-8, 1998.
Pankov et al., "Fibronectin at a glance" J Cell Sci., 2002, 115(pt20):3861-3863.
Panni et al., "In vitro evolution of recognition specificity mediated by SH3 domains reveals target recognition rules," *J. Biol. Chem*, 277:21666-74.
Partial Supplemental Search Report and Provisional Opinion for EP16828310.9, mailed Dec. 5, 2018.
Pawson et al., "Assembly of a cell reulatory systems through protein interaction interaction domains," *Science*, 300:445-52, 2003.
Pham et al., "NMR studies of *Borrelia burgdorferi* OspA, a 28kDa protein containing a single-layer 13-sheet," *J Biomol NMR*, 11:407-414, 1998.
Plaxco et al., "A comparison of the folding kinetics and thermodynamics of two homologous fibronectin type III modules," *J Mot Biol.*, 270:763-770, 1997.
Plaxco et al., "Rapid refolding of praline-rich all-beta-sheet fibronectin type III module," *Proc. Natl. Acad. Sci. USA*, 93:10703-10706, 1996.
Portnoff et al., "Ubiquibodies, Synthetic E3 Ubiquitin Ligases Endowed with Unnatural Substrate Specificity for Targeted Protein Silencing", *The Journal of Biological Chemistry* 289:11,7844-7855,2014.
Prestegard., "New techniques in structural NMR—anisotropic interactions," *Nature Struct Biol*, 5:517-522, 1998.
Rahuel et al., "Structural basis for specificty of Grb2-SH2 revealed by a novel ligand binding mode," *Nat Struct Bio/* 3:589-9, 1996.
Reina et al., "Computer-aided design of a PDZ domain to recognize new target sequences," *Nat. Struct Biol.*, 9:621-7, 2002.
Rippmann et al., "Phosphorylation-dependent praline isomerization catalyzed by Pin1 is essential for tumor cell survival and entry into mitosis," *Cell Growth Differ* 11:409-16, 2000.
Robert et al., "Tumor targeting with newly designed biparatopic antibodies directed against two different epitopes of the carcinoembryonic antigen (CEA)" *Int. J. Cancer* 1999, 81, 285-291.
Rocklin et al. "Global analysis of protein folding using massively parallel design, synthesis, and testing", *Science*, vol. 357, pp. 168-175, 2017.
Schlessinger et al., "SH2 and PTB domains in tyrosine kinase signaling," *Sci Stke*, RE12, 1999.
Schmitt et al., "Blocking the tunnel: engineering of Candida rugosa lipase mutants with short chain length specificity" Protein Eng., 2002, 15:595-601.
Sechler et al., "Modulatory Roles for Integrin Activation and the Synergy Site of Fibronectin during Matrix Assembly" Malec. Biol. Cell., 1997, 8(12):2563-2573.
Sha et al., "Dissection of the BCR-ABL signaling network using highly specific monobody inhibitors to the SHP2 SH2 domains" Proc Natl. Acad. Sci. U.S.A., 2013, 110:14924-14929.
Shaner et al., "A guide to choosing fluorescent proteins," *Nat Methods*, 2:905-9, 2005.
Shierle et al., "The DsbA signal sequence directs efficient, cotranslational export of passenger proteins to the *Escherichia coli* periplasma via the signal recognition particle pathway," *J Biotechnol*, 185:5706-13, 2003.
Sidhu et al., "Phage display for selection of novel binding peptides," *Methods Enymol*, 328:333-363, 2000.
Skelton et al., "Origins of PDZ domain binds with high affinity and specificity structure. Structure determination and mutagenesis of PDZ domain," *J Biol Chem.*, 278:7645-7654, 2003.
Skerraa, "Engineered protein scaffolds for molecular recognition," *J. Mot. Recognit.*, 13(4):167-87, 2000.
Smith et al. "Protein loop grafting to construct a variant of tissue type plasminogen activator that binds platelet integrin alpha llb beta 3", *J. Biol. Chem.*, vol. 270, No. 51, pp. 30486-30490, 1995.
Song et al., "Cloning and expression of a B-Galactosidase Gene of Bacillus Circulans" Biosci. Biotechnol. Biochem., 2011, 75:1194-1197.
Songyang et al., "A single point mutation switches the specificity of group III Src homology," *J Biol Chem* 270:26023-32, 1995.
Songyang et al., "Recognition and specificty in protein tyrosine kinase-mediated signalling," *Trends Biochem Sci*, 20:470-5, 1995.
Songyang et al., "SH2 Domains Recognize Specific Phosphopeptide Sequencess," *Cell*, 72:767-78, 1993.

(56) References Cited

OTHER PUBLICATIONS

Starkenburg et al. "Genome Sequence of the Chemolithoautotrophic Nitrite-Oxidizing Bacterium Nitrobacter Winogradskyi Nb-255." *Applied and Environmental Microbiology* 2006, 72(3), pp. 2050-2063.

Steiner et al., "Signal sequences directing cotransitonal translocation expand the range of proteins amenable to phage display," *Nat Biotechnol.*, 24:823-31, 2006.

Steitz et al., "Structural dynamics of yeast hexokinase during catalysis," *Phi/as. Trans. R. Soc. Land. B. Biol Sci.*, 293:43-52, 1981.

Stern et al., "Tyrosine kinase signaling in breast cancer: ErbB family receptor tyrosine kinases," *Breast Cancer Res*, 2:176-83, 2000.

Tenev et al. "Both SH2 Domains are Involved in Interaction of SHP-1 with the Epidermal Growth Factor Receptor but Cannot Confer Receptor-Directed Activity to SHP-1/SHP-2 Chimera." *Journal of Biological Chemistry* 1997, 272(9), 5966-73.

Tjandra et al., "Defining long range order in NMR structure determination from the dependence of heteronuclear relaxation times on rotational diffusion," *Nature Struct Biol*, 4:443-449, 1997.

Tsien et al., "Seeing the machinery of live cells," *Science*, 280:1654-5, 1998.

Van der Veen et al., "Rational design of cyclodextrin glycosyltransferase from Bacillus circulans strain 251 to increase a-cyclodextrin production" 2000, 296:1027-1038, J. Mol. Biol.

VanAntwerp et al., "Fine affinity discrimination by yeast surface display and flow cytometry," *Biotechnol Prag* 16:31-7, 2000.

Verdecia et al., "Structural basis for phosphoserine-proline recognition by group IV WW domains," *Nat Struct Bio/* 7:639-43, 2000.

Weiss et al., "The development of molecular clams as drugs," *Drug Discovery Today*, 11:819-824, 2006.

Wiedemann et al., "Quantification of PDZ domain specificty, prediction of ligand affinity and rational designe of super-binding peptides," *J. Mot. Biol.*, 343:703-18, 2004.

Wilks et al., "A specific, highly active malate dehydrogenase by redesign of a lactate dehydrogenase framework" Science, 1988, 242:1541-1544.

Wojcik et al., "A potent and highly specific FN3 monobody inhibitor of the Abl SH2 domain" Nat. Struct. Mal. Biol., 2010, 17:519-527.

Xu et al., "Directed evolution of high-affinity antibody mimics using mRNAdisplay," *Chem Biol*, 9:933-942, 2000.

Yaffe et al., "A motif-base profile scanning approach for genome-wide prediction of signaling pathways," *Nat. Biotechnol*, 19:348-353, 1998.

Yaffe et al., "PhosphoSerine/threonine binding domains: you can pSERious?" *Structure* 9:R33-8, 2001.

Yan et al., "Themodynamic and Kinetic Exploration of the Energy Landscape of Borrelia burgdorferi OspA by Native-state Hydrogen Exchange," *J Mot Biol*, 323:363- 75,2002.

Yang et al., "TROSY-based HNCO pulse sequences for the measurement of 1HN-15N, 15N-13CO, 1HN-13CO, 13CO-13Ca and 1HN-13Ca dipolar couplings in 15N, 13C, 2H-labeled proteins," *J Biomol NMR*, 14:333-343, 1999.

Zhang et al., "Convergent and divergent ligand specificity among PDZ domains of the LAP and zonula occludens (ZO) families," *J Biol. Chem.*, 281 :22299-311, 2006.

Zucconi et al., "Domain repertoires as a tool to derive protein recognition rules," *FEBS Lett*, 480:49-54, 2000.

\* cited by examiner (a)

```
STOFN3-1    315 PP--PKPQIASIASGNE--TITVKWYDTNASG---YYITYWSNFSQKVT 356
STOFN3-2    399 PSSVPNPPIIKVKIGNL--NATLTWYDTFNGG---YPIEGYYLYVNGKG 442
STOFN3-3    488 -----ANLTVTVYKKIN--GFLVSWNSTSKAK---YIL--TVSKENVVL 524
STOFN3-4    568 ----PASPTVNWSITLN--TVSLNWSKVSGAE---Y----YLIYDNGKL 603
PDB ID: 2DJU  1 ----PKPPIDLVVTETTATSVTLTWDSGNSEPVTYYGIQYRAAGTEGPF  45
```
```
STOFN3-1    357 INVGNV--TSYTIKHLKDGVTYYIQIVPYNSLGNGT-PSDIISAT--- 398
STOFN3-2    443 INVGNI--TSYVLTNLTAGELYTIELIAYNKIGNSS-ISSVSFIAASK 484
STOFN3-3    525 LNVSTT--NTSYFVKVPFGV-YNISLEAVNIVGITKYAFILIYYIQ-- 566
STOFN3-4    604 ITNTTN--TAFTFN-LTIGQN-EIEVYAANAYYKSA-PYIINDVR--- 643
PDB ID: 2DJU 46 QEVDGVATTRYSIGGLSPFSEYAFRVLAVNSIGRGPPSEAVRARTGEQ 106
```

(b)
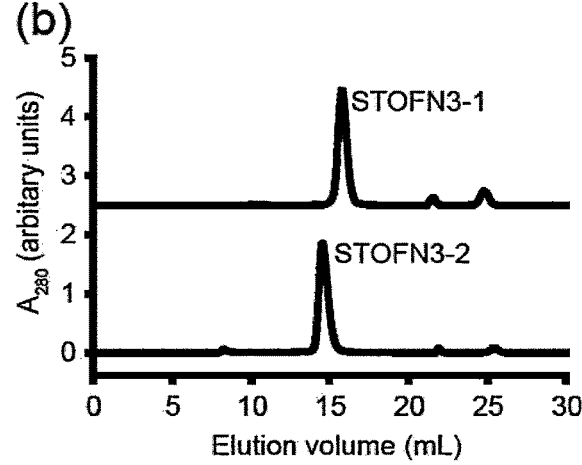

(c)
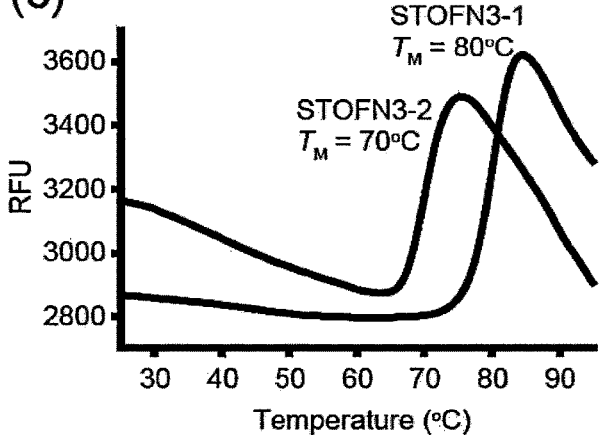

FIG. 1A-C

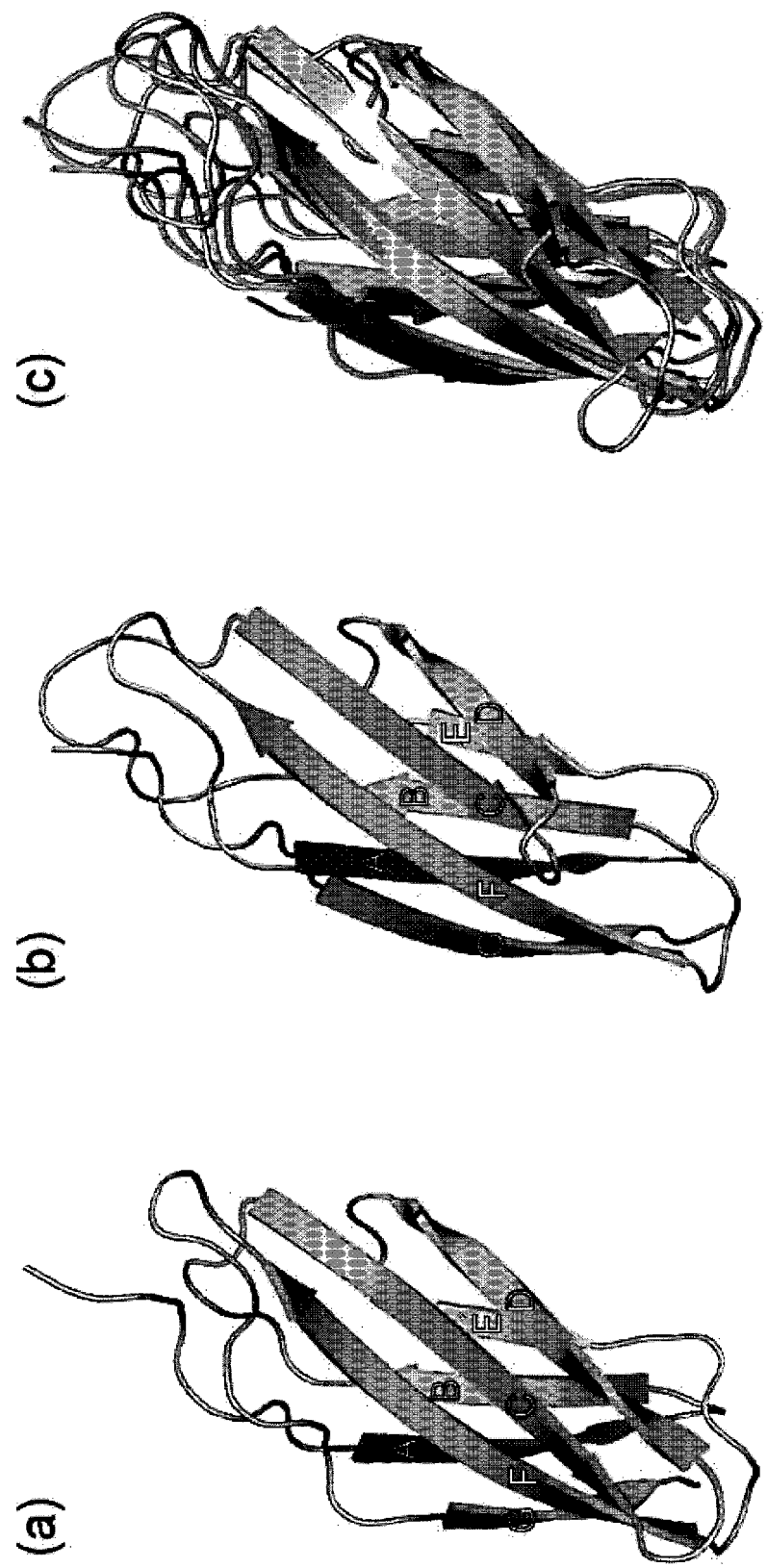
FIG. 2A-C

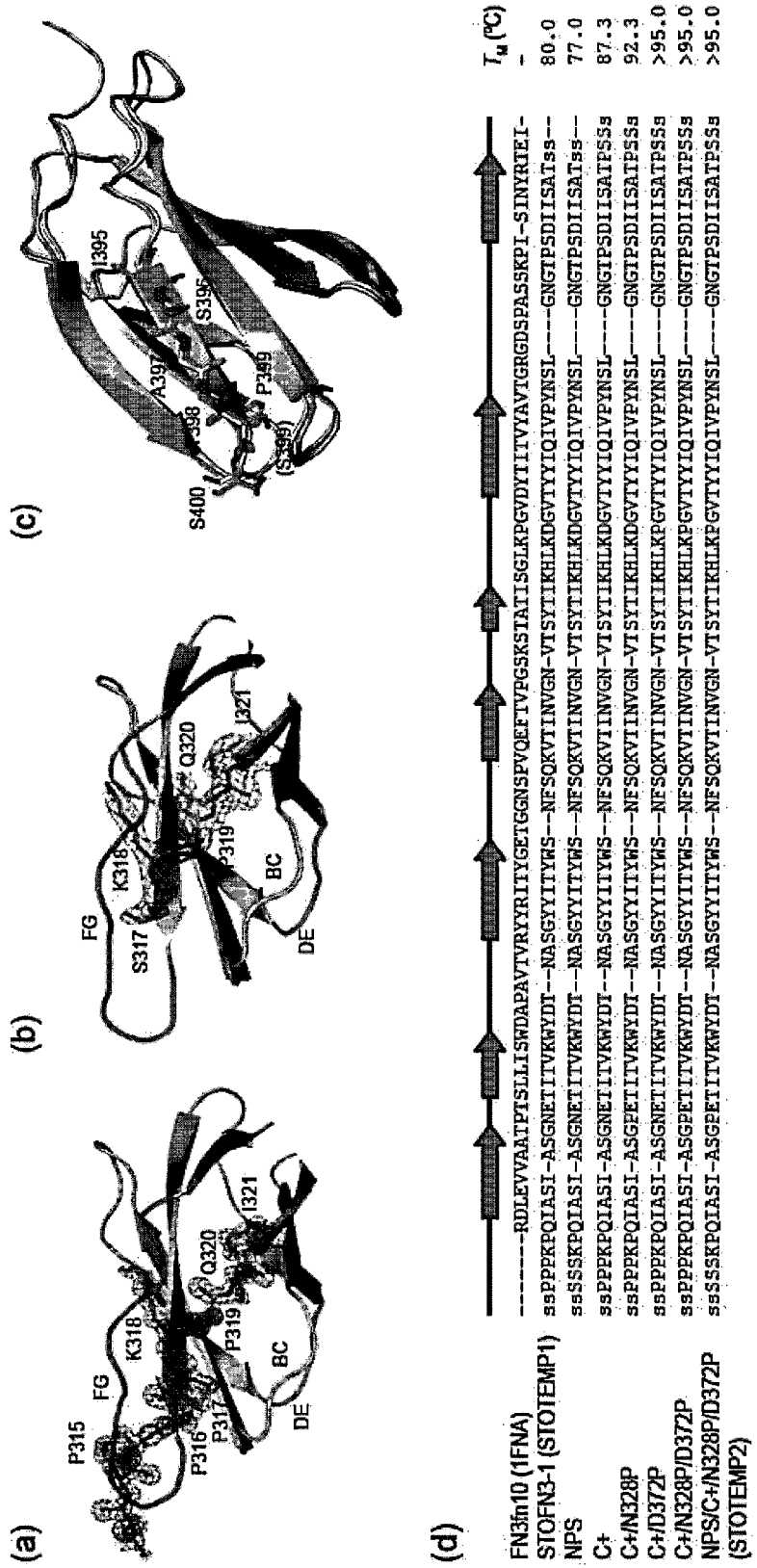
FIG. 3A-D (b)

| | AB | BC | CD | DE | EF | FG | $T_M$ (°C) |
|---|---|---|---|---|---|---|---|
| STOFN3-1 | ASGNETIT | WYDTNASG | WSNFSQK | VGNVTSY | IKHLKDGVT | PYNSLGNGTPSDII | 80.0 |
| STOFN3-1/ABSer | ASSSSSIT | WYDTNASG | WSNFSQK | VGNVTSY | IKHLKDGVT | PYNSLGNGTPSDII | 79.0 |
| STOFN3-1/BCSer | ASGNETIT | WYSSSSSG | WSNFSQK | VGNVTSY | IKHLKDGVT | PYNSLGNGTPSDII | 74.7 |
| STOFN3-1/CDSer | ASGNETIT | WYDTNASG | WSSSSSQK | VGNVTSY | IKHLKDGVT | PYNSLGNGTPSDII | 82.2 |
| STOFN3-1/DESer1 | ASGNETIT | WYDTNASG | WSNFSQK | VGSSSSY | IKHLKDGVT | PYNSLGNGTPSDII | 81.7 |
| STOFN3-1/DESer2 | ASGNETIT | WYDTNASG | WSNFSQK | VSSSSSY | IKHLKDGVT | PYNSLGNGTPSDII | 54.3 |
| STOFN3-1/EFSer | ASGNETIT | WYDTNASG | WSNFSQK | VGNVTSY | IKSSSSVT | PYNSLGNGTPSDII | 64.0 |
| STOFN3-1/FGSer1 | ASGNETIT | WYDTNASG | WSNFSQK | VGNVTSY | IKHLKDGVT | PYSSSSSSPSDII | 66.7 |
| STOFN3-1/FGSer2 | ASGNETIT | WYDTNASG | WSNFSQK | VGNVTSY | IKHLKDGVT | PSSSSSSSSPSDII | 60.0 |
| STOFN3-1/FGSer3 | ASGNETIT | WYDTNASG | WSNFSQK | VGNVTSY | IKHLKDGVT | PYSSSSSSSSSDII | 63.2 |
| STOFN3-1/FGSer4 | ASGNETIT | WYDTNASG | WSNFSQK | VGNVTSY | IKHLKDGVT | PSSSSSSSSSSSII | 62.0 |
| STOTEMP3* | ASGPETIT | WYDTNASG | WSSSSQK | VGNVTSY | IKHLKPGVT | PYNSLGNGTPSDII | >95.0 |
| STOTEMP4* | ASGPETIT | WYDTNASY | WSSSSQK | VGNVTSY | IKHLKPGVT | PVNSLGNGTPSDII | >95.0 |
| STOTEMP4*/FGSer5 | ASGPETIT | WYDTNASY | WSSSSQK | VGNVTSY | IKHLKPGVT | PVSSSSSSSPSDII | 89.3 |
| STOTEMP4*/FGSer6 | ASGPETIT | WYDTNASY | WSSSSQK | VGNVTSY | IKHLKPGVT | PYSSSSSSSPSDII | 85.8 |
| STOTEMP4*/FGSer7 | ASGPETIT | WYDTNASY | WSSSSQK | VGNVTSY | IKHLKPGVT | PSSSSSSSPSDII | 86.5 |

*C-terminal extented.

FIG. 4B (c)

| | BC | CD | DE | FG | | $T_M$ (°C) |
|---|---|---|---|---|---|---|
| STOFN3-1 | WYDT------- | -NASG WSN------- | ----FSQ VGN------- | ----VTSY PYNS------- | ----LGNGTPSDII | 80.0 |
| STOFN3-1/BC+2 | WYDTSS----- | -NASG WSN------- | ----FSQ VGN------- | ----VTSY PYNS------- | ----LGNGTPSDII | 80.3 |
| STOFN3-1/BC+4 | WYDTSSSS--- | -NASG WSN------- | ----FSQ VGN------- | ----VTSY PYNS------- | ----LGNGTPSDII | 76.7 |
| STOFN3-1/BC+8 | WYDTSSSSSSSS | -NASG WSN------- | ----FSQ VGN------- | ----VTSY PYNS------- | ----LGNGTPSDII | 77.7 |
| STOFN3-1/CD+2 | WYDT------- | -NASG WSNSS----- | ----FSQ VGN------- | ----VTSY PYNS------- | ----LGNGTPSDII | 71.7 |
| STOFN3-1/CD+4 | WYDT------- | -NASG WSNSSSS--- | ----FSQ VGN------- | ----VTSY PYNS------- | ----LGNGTPSDII | 70.0 |
| STOFN3-1/CD+8 | WYDT------- | -NASG WSNSSSSSSSS | FSQ VGN------- | ----VTSY PYNS------- | ----LGNGTPSDII | 67.7 |
| STOFN3-1/DE+2 | WYDT------- | -NASG WSN------- | ----FSQ VGNSS----- | ----VTSY PYNS------- | ----LGNGTPSDII | 55.8 |
| STOFN3-1/DE+4 | WYDT------- | -NASG WSN------- | ----FSQ VGNSSSS--- | ----VTSY PYNS------- | ----LGNGTPSDII | 55.0 |
| STOFN3-1/DE+8 | WYDT------- | -NASG WSN------- | ----FSQ VGNSSSSSSSS | VTSY PYNS------- | ----LGNGTPSDII | 54.8 |
| STOFN3-1/FG+2 | WYDT------- | -NASG WSN------- | ----FSQ VGN------- | ----VTSY PYNSSS----- | ----LGNGTPSDII | 68.2 |
| STOFN3-1/FG+4 | WYDT------- | -NASG WSN------- | ----FSQ VGN------- | ----VTSY PYNSSSSS--- | ----LGNGTPSDII | 68.0 |
| STOFN3-1/FG+8 | WYDT------- | -NASG WSN------- | ----FSQ VGN------- | ----VTSY PYNSSSSSSSSSL | GNGTPSDII | 67.2 |

FIG. 4C

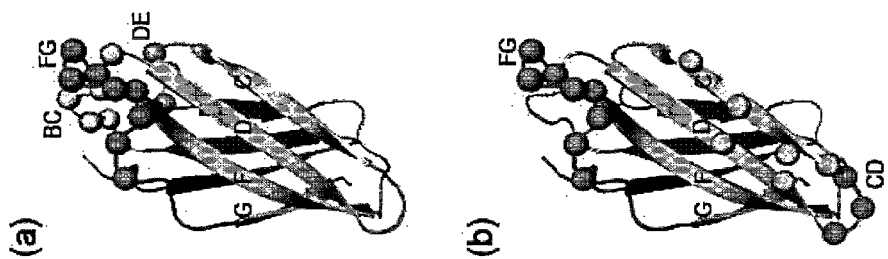
FIG. 6A-B

(c)

| | Oligomerization state | Thermal stability ($T_M$, °C) |
|---|---|---|
| STOTEMP5 | Monomeric | >95.0 |
| SUMOMbL03 | Monomeric | 63.5 |
| SUMOMbL14 | Monomeric | 63.5 |
| MBPMbL08 | Large aggregate | - |
| MBPMbL17 | Late elution* | 73.3 |
| EGFPMbL24 | Monomeric | 54.2 |
| EGFPMbL26 | Late elution* | 53.5 |
| AbISH2MbL03 | Monomeric | 74.0 |
| AbISH2MbL04 | Monomeric | 69.5 |
| NSH2MbL06 | Monomeric | 86.3 |
| NSH2MbL10 | Monomeric | 80.5 |
| CSH2MbL01 | Late elution* | 64.8 |
| CSH2MbL03 | Late elution* | 66.5 |
| | Mean | 68.1 ±10.1 |
| SUMOMbS08 | Large aggregate | - |
| SUMOMbS20 | Monomeric | 53.5 |
| SUMOMbS34 | Large aggregate | - |
| MBPMbS01 | Late elution* | 53.7 |
| MBPMbS09 | Late elution* | 53.2 |
| MBPMbS12 | Monomeric | 53.5 |
| EGFPMbS04 | Monomeric | 85.5 |
| EGFPMbS05 | Monomeric | 70.2 |
| EGFPMbS12 | Monomeric | 66.0 |
| AbISH2MbS01 | Monomeric | 71.0 |
| AbISH2MbS02 | Monomeric | 53.5 |
| AbISH2MbS07 | Monomeric | 50.5 |
| | Mean | 61.1 ±11.6 |

*Mono-dispersed single peak

FIG. 7C

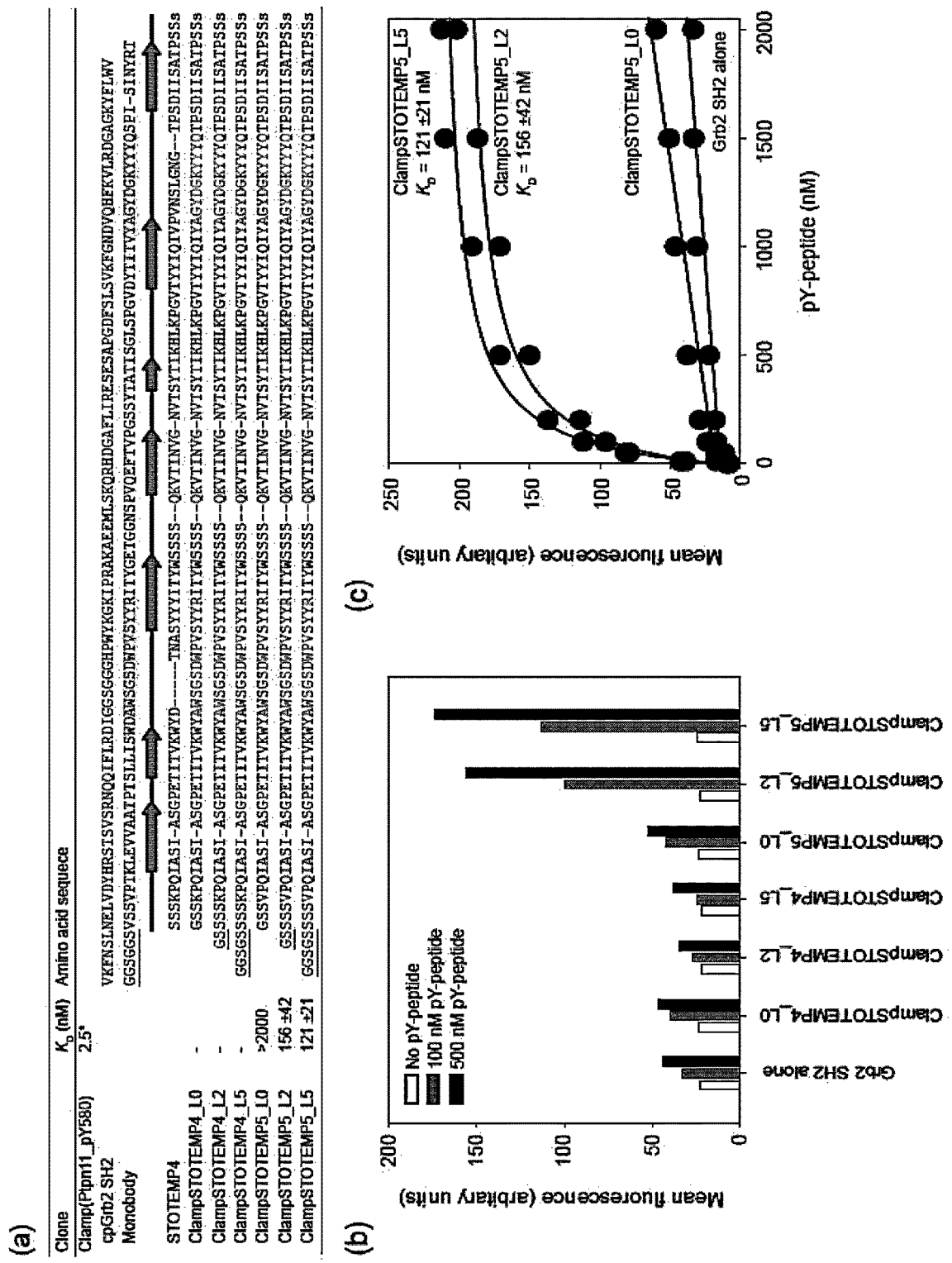
FIG. 8A-C

FIG. 11A-B

```
                        SEQUENCE LISTING

Sequence total quantity: 7
SEQ ID NO: 1            moltype = AA  length = 84
FEATURE                 Location/Qualifiers
source                  1..84
                        mol_type = protein
                        organism = Sulfolobus tokodaii
SEQUENCE: 1
PPPKPQIASI ASGNETITVK WYDTNASGYY ITYWSNFSQK VTINVGNVTS YTIKHLKDGV   60
TYYIQIVPYN SLGNGTPSDI ISAT                                         84

SEQ ID NO: 2            moltype = AA  length = 86
FEATURE                 Location/Qualifiers
source                  1..86
                        mol_type = protein
                        organism = Sulfolobus tokodaii
SEQUENCE: 2
PSSVPNPPII KVKIGNLNAT LTWYDTFNGG YPIEGYYLYV NGKGINVGNI TSYVLTNLTA   60
GELYTIELIA YNKIGNSSIS SVSFIA                                       86

SEQ ID NO: 3            moltype = AA  length = 79
FEATURE                 Location/Qualifiers
source                  1..79
                        mol_type = protein
                        organism = Sulfolobus tokodaii
SEQUENCE: 3
ANLTVTVYKK INGFLVSWNS TSKAKYILTV SKENVVLLNV STTNTSYFVK VPFGVYNISL   60
EAVNIVGITK YAFILIYYI                                               79

SEQ ID NO: 4            moltype = AA  length = 76
FEATURE                 Location/Qualifiers
source                  1..76
                        mol_type = protein
                        organism = Sulfolobus tokodaii
SEQUENCE: 4
PASPTVNWSI TLNTVSLNWS KVSGAEYYLI YDNGKLITNT TNTAFTFNLT IGQNEIEVYA   60
ANAYYKSAPY IINDVR                                                  76

SEQ ID NO: 5            moltype = AA  length = 709
FEATURE                 Location/Qualifiers
source                  1..709
                        mol_type = protein
                        organism = Sulfolobus tokodaii
SEQUENCE: 5
MKRNTLLALV LVILIFPTLS TAYIEFTTSI NQAIPDSLVY ATSAYYDGKI FLIGGENLYS   60
TPVNSVYVYE NGSWYLGPSL PFSLSSAGAT VCNNTLYVVG GANSTSIFGG ILEFIGNGWK  120
VITNSMPIPV YGAIVFSYDY KIYVIGGMNY SGNSLVPPVN YIQVYNLKTN SWQIIGNAPL  180
RLAYSAYYFN GSALFVVGGF TQSATLTSSV FVYYPENNTW ISLPSLPGVE AGGVLGYYNG  240
YMYLVGGLYY VSGAYQLGEI LYYYNGTWRN TNIQEQIPTQ FSTSVQIGNK LIILGGFGPG  300
NIPSNAMQTV SIYLPPPKPQ IASIASGNET ITVKWYDTNA SGYYITYWSN FSQKVTINVG  360
NVTSYTIKHL KDGVTYYIQI VPYNSLGNGT PSDIISATPS SVPNPPIIKV KIGNLNATLT  420
WYDTFNGGYP IEGYYLYVNG KGINVGNITS YVLTNLTAGE LYTIELIAYN KIGNSSISSV  480
SFIAASKANL TVTVYKKING FLVSWNSTSK AKYILTVSKE NVVLLNVSTT NTSYFVKVPF  540
GVYNISLEAV NIVGITKYAF ILIYYIQPAS PTVNWSITLN TVSLNWSKVS GAEYYLIYDN  600
GKLITNTTNT AFTFNLTIGQ NEIEVYAANA YYKSAPYIIN DVRNYIVVVN STAISISVPQ  660
```

```
IKVVSGENTD APLQTNNIDL KSAIIVITVF VIALLMILVI LRERSDNYW           709

SEQ ID NO: 6              moltype = AA  length = 108
FEATURE                   Location/Qualifiers
source                    1..108
                          mol_type = protein
                          organism = Pyrococcus horikoshii
SEQUENCE: 6
PSPPSGVTLM LNGSYVELSW LPSPDSDVAG YFIYKDGKRL NEVPIEKPNF RDIYSGTLNY 60
SISAIDFSGF ESEKTEVFPV KLEVDEENLT AGYPGAVKVK VENLDGEA            108

SEQ ID NO: 7              moltype = AA  length = 4436
FEATURE                   Location/Qualifiers
source                    1..4436
                          mol_type = protein
                          organism = Pyrococcus horikoshii
SEQUENCE: 7
MINIKGLILT LILFISLIPP WALGEGSKDT KVFADYYLAG DSVVINATLY DAGSCNLTFS 60
VFSPIEAPNV SEISFTWMNL SEYIESATEA TYGEYLRDGN VIMREDDGYF IYELPFSLNY 120
FGREIKKIAV NTNGLIELLE EYEEPRIEDY YGIHEEGEFY ESDVIFGLDE DLVTYDGYLL 180
LVNLQDKIVI EWLASTYEDY ESEIVDNINF QVIINSNGTI TWSYKSLEYS YHDYDLFSGY 240
YSKVSGDVKG FTKGEGKSFA IQVPLGTPKL YTYQVRESGS YLLTLPLSNY HVEVFANCMD 300
DPDLSNNLAE VGVWPGDYWV ENASINNLIP GEFASINFKV RTTSKIPSAK VKLLRNGVEE 360
KIEYLSFYNG IAEGEISWLV QGGNYTLALL VEGKGDINSS NNIYLLGNYN FPLPNFEVGN 420
YSIDLPTCVD STGEVRVNVT STANWSIPVR LTLVYEEGNR SYTRYISTKG EEESEVIFTP 480
MIKAGTLEKV VIEIDPWNEV EESNESDNKV EVPYHIIIEK PDFTVKSLNI PGNVSIGNLY 540
EVNVTLDNLG GCYGRNVLVK LYENGTSKDW RRVRINNETN VTLTWKPGNA GLVNLTVVVD 600
PYSYVDEINE GNNRLSRLIF VNAPDFKISK VELLSFDGIA GSKAKFNVTV KNEGEDYSGY 660
FSIAVYGGLR SSIAYLRGIK SGEEKWTIIS LPINGGNSTL IFVVDPHNVI SETNEGNNVI 720
FYNMGYIPKP NFVVKEISLP NNTVGYIPLN ITIGNVGAPY NATSYQVPVK IKTEYGWKVS 780
YLRGIIRDNY TISIDSLAML PPGSTINVTV NYNMKVNETS YSDNSLIINY TTGYPDLELG 840
IIPPSGELSA GKDVKITFLV KNVGNATLRI DRSSWYSPYL GLYVTLEDEN GKTHTLGRYE 900
LAPATLSPGA NISQVVWITL NGGTNKIMGR IVDEYENIYE NNNDTLILTL EKPDFAILNY 960
SIPDEILNGT AYLYKAYPIV LNISNLGGNF SDGIRVDLFD NGIIKTSTSV YGLESGASRD 1020
VTLRYLPSSG KHNLSIVLDP YNRWIEENEE NNNLTFSLSF GKPDLKVEGI TWAPYNFTSG 1080
ENVLFTIYVK NLGQPPLKSF TVRAEIWNGT RKIYSTNAYP RNWSFGKGET KEFNWRWYNA 1140
KPGNLTVKIV VDYYNSIPEG NESNNEFSAF LGNVGTPDFK LENLSVEDLA YGKFVRINAT 1200
VKNLGDSIYR PITVLFNVSG ERYYRTVYGI KENESKSVTL PWYVDRVGEV RVKVEVDGEN 1260
RIVEGNESNN IIERTYYVES PELMLSGYEW LEEEVRRGYL AYKVNVTNTG GDVYRGFYVQ 1320
MFVDGEPKSS VWINKLLHGE TAERTLRWRF SSGGRKEVRI VVDPQDYIPE SNEDNNAIVE 1380
NVTIVLPDIE VLSLNIPSMH ANSYFKVNAT IKNSGGQDVK RIFYVSLYQD GKLLGSAPVY 1440
SLASGEVKEV TLTIRPYPGN STFKVVVDPT NAVVELNEDN NEISVRSYVK APDIVVVSAD 1500
LGNFTYPGEM VNAKVRIRNS GDYKSGVYLL IRNKRRKLGS AYVDSITPGE EIEVNVPWLV 1560
DSGDYNVSVI ADPYNSVREW DEENNKLDIE VSVPSPDLTV ENITHSGKEV AGEEIIIKVT 1620
VKNIGESSKL PFYIVLYANS SFVGINRVTK IDKGESITLE FKWRASYGEY ALRAIVDPYD 1680
EVYEENESNN EGMVKVFIED EEPPVLKLTY PENGTFTNKP YIGAYLRDEG SGVKFGEIEV 1740
YREGTSVPGS TKFSGGWLIF QNSTPLLDGK YTVTVKAVDR AGNEITYSWN FTLDREPPRI 1800
VCNLTDGTLY NGTVVPGVQV IDDNLDWYKV KVNGREFSGP IKLDGTYTLN VTAKDKAGNL 1860
AEKIIRFTVN GVPSPPSGVT LMLNGSYVEL SWLPSPDSDV AGYFIYKDGK RLNEVPIEKP 1920
NFRDIYSGTL NYSISAIDFS GFESEKTEVF PVKLEVDEEN LTAGYPGAVK VKVENLDGEA 1980
NGTLSIILID EFGNEIEKLS RKVEVPRGRS SHEFVFMVPR GLTLIRGELK VGNSTARIIH 2040
RAKVREGENP EIRVGKLLAG FPGLVEVEIR NCGIVELNTS ETLMKLDNSS GELIEAPLTI 2100
PPGKKTVLRY KIVPPKKGSY NLTFRIADVE VRKIVNVSES VLNPITISTE NFIKGGKAKI 2160
YVSFRNIGSA PIFVKSIELN GMSKRLSIEL PPNLSVEESF EYLISEENVE INATVNTDVG 2220
KFRKSLTLTA EQPEYNADVS VSSVYEVGKE ILITGVYNSN SGMLSNVPVK VSIARGGFVR 2280
EYIVTTNENG YFNLTFRPFK GESGHFIVSA THPKIELLER DAEFDVVGIE VIPSLYLLTV 2340
PVEFNGTVRV RLINYWRASD VSVSVKAPPE YEVSIPKVLH LKPGSNIINI GLSSKNAVNG 2400
SIMITFKARQ LGLNITRSLT LKLKVLPPAP AIVTSPNFLD VGVLTNETAS AEVVVRNLGF 2460
TALRNVSIRS SIPWVKVVSN FTEVDPKDNE SISLYIEPPR YNTGTFKGEI TISSSNYNPI 2520
KVPMRIRVTP NATGGVKVTV MDPNATRLEN VKLTLYNGYF HFEGYTNKNG TLEVENVPIG 2580
EYKLFASLEG YYGYSTSITI EVGVEKNVSI ILTPSILEVE WEVVPVTIQD VYIIKHEMWY 2640
STHVPAPEIR MEGGDLEVYV DYEKLAEEGM LEFRGQVIVR NTHQYISVYN VTFESGGSHY 2700
IDVEFGINRI DELKPGEAVI VPYVVRIYYS RSPPINPCLH ETKVFKLKAG VVCVEEAGKI 2760
TLKAQRIHQI VVKPTCKGCW ESVFPVAGKL AFMAIAQKVG QALGNIDDTG VLSTLAGEAL 2820
NNLESLFDAY NAYKANPTKE NMENYVKTFN SVKANLASLF MFDPVAYQEI NSLQLTLIKT 2880
PKGDIAGFAV SRTATPVYAL GMGVGKIENG QLKVDYKKAV NIANGIVLNV MSKMGGALGG 2940
IASGVGLLQL LDKAAEDLPP YIAQLFLNCA ICLMRNDCTL PEGEEIRPIQ IIASGSLGGY 3000
PSMIPSGLAG GGDGGTAVGR FTCGGLPTVK KSSTSMSCST CSSEDVVKER VCRLFRESET 3060
HDEEEPSNTL HMCVDLVLTI EQRLTFERQA FRASLKFTNT NRNYSLENVS VRVIFFDEEG 3120
NRVDDKFFVR LDEKAGLSGS SLEPEKTAEM KWLIIPKVGA AEKFRARYYV MANITARVGS 3180
TKLVYETWPA MIEVEPVPQL VLDYVLPSYV FGDDPYTPEK ELPIPIFGV RVKNVGYGTA 3240
RKLRIASAQP KIERSNYPGV YIDFKIIGTL VNGKKVPNSL TIDFGDLNPG ESSTAAWLMI 3300
AEVSGKFLQY NATFKHSDEL GGNETSLIKE VRTHFLIRAF NNTENDDGML DFLVDDDGDG 3360
KPEKIIDSRG FDYNVLLLNF TEVEEGSMRK IIPEMKTPFW VYFTVPFKGS VVRSDGKNPM 3420
DQWMENGTLH VLDDLGTPEFY ILKSNQPPIP RIYVKEPVIA NETVVLDGSL SYDPDGSIIA 3480
YTWKIGNESF VGDKVSYVFR EPGTYNVTLT VRDDKGTESS KTMEIKVYLG PKFNESLKVE 3540
PQWGIVPFNL SITFNVTNVG DVSGEYSYII KLGNSTIAEG SEIIESGRWK VINSTVEIRK 3600
EGNYTVTANN LSKTVTAYRK VYGNLTENYI KEKDFGHYKS FYWNEFKRDF EGWVEEALST 3660
IELPKVNFKV LNYFPGNWSL LNYSEMLNIT KGWGWINATY ARRVRVEGLE EFKYLIVNVT 3720
```

-continued

```
QLVVLLGNAT HELDESPPTL NVTPSSGIYS EIPKIQVRTC DETGITLVWG AVGNYTKEFT    3780
EVESNGTCST WEGIVPLNIG NNTVAIYAED EFGNRGNVSL WIYLNPEAPV IYIESPEEKV    3840
YNSREVMINY TVVNHDLVGV VAYLNGELIS SNASYSGFIK LDYGWHNFTI YAWDVSYNVS    3900
KSVIFRVNEP PSVDFSWEVD NLTVKFEANA SDEDGISKYL WDFGDNESSL LVNPTHTYRK    3960
GGRYNVTLTV WDSYNLSSSI SKEVVVFGSS TLTMVKEYSY TKDFGFYNTT SWKDFLKDFE    4020
VWVNLTLRNV TLPLEYFEEI IEVNVENWSL ISVEKNLKND IGEMSAEYER NATIVGIMNY    4080
TRVTLKLTQE VILSGRARKV EDKIPPLVEI LFPRNMTYNE TIREIKVRAT DESGIANVTA    4140
TINGESLSLE KVNETWIGRV ELDDGKYELN VFASDKWGNV GCSTVNFTIN RSVKVRIING    4200
TEIVTIPGDI KTRVYFEGDI IVEIVKESLR FKIPSGGTLV IDERGRKDPW LLARINSTIE    4260
NISKTSRIFE ENGKKVHEIR YRISISRGYA ILVVPLEGMK VSSIRIIKNG TVTRDEKHGN    4320
YYKLSKGYLF IFLSEDPIVE VTLSKIEKKD IFRVLYYAGI IWERNYLRLK EEFIMKMSNE    4380
TSQEAIRLHE EAEKYYLKGR EYYPRIPSPS AIYWYAVYMR KAYLTERKAL ELLSIS       4436
```

METHODS AND COMPOSITION INVOLVING THERMOPHILIC FIBRONECTIN TYPE III (FN3) MONOBODIES

CROSS-REFERENCE TO RELATED APPLICATIONS

This application is a divisional of U.S. patent application Ser. No. 15/733,530 filed Aug. 21, 2020, now U.S. Pat. No. 11,680,091, which is national phase application under U.S.C. § 371 of International Application No. PCT/US2019/018866 filed Feb. 21, 2019, which claims the benefit of priority of U.S. Provisional Patent Application No. 62/634,616 filed Feb. 23, 2018, all of which are hereby incorporated by reference in their entirety.

STATEMENT OF GOVERNMENT SUPPORT

This invention was made with government support under GM090324 awarded by the National Institutes of Health. The government has certain rights in the invention.

SEQUENCE LISTING

The application contains a Sequence Listing prepared in compliance with ST.26 format and is hereby incorporated by reference in its entirety. Said Sequence Listing, created on Oct. 10, 2023 is named ARCDP0616USD1.xml and is 12,650 bytes in size.

BACKGROUND OF THE INVENTION

II. Field of the Invention

Embodiments are directed generally to biology, medicine, and protein engineering.

III. Background

The fibronectin type III domain (FN3) has been established as an effective non-antibody, "alternative" scaffold for the generation of novel binding proteins. A member of the immunoglobulin superfamily, FN3 has three surface exposed loops at one end of the molecule which are analogous to antibody CDRs. Engineering strategies using this scaffold are based on combinatorial libraries created by diversifying both the length and amino acid sequence of these surface loops. From such libraries, FN3 variants capable of binding to a target of interest can be isolated using various selection methods. The utility of the FN3 scaffold has been demonstrated in producing high-affinity binding proteins to a number of different protein targets (reviewed in Bloom and Calabro, 2009). These binding proteins generated from this scaffold are referred to as monobodies. The FN3 scaffold offers many advantages compared to conventional antibodies or fragments thereof because it lacks disulfide bonds, can be readily and highly expressed in bacterial systems, and is relatively small.

The FN3 scaffold has produced high-affinity binding proteins to a number of distinct targets, achieving dissociation constants in the low- to mid-nanomolar range and as low as 1.1 picomolar (Bloom and Calabro, 2009; Hackel et al., 2008). Binding proteins based on the FN3 domain have also been used in a number of applications including, conformation specific purification of a target protein (Huang et al., 2006), probing protein conformational changes in cells (Koide et al., 2002), antagonism of a growth factor receptor for therapeutic use (Getmanova et al., 2006), inhibition of virus replication (Liao et al., 2009), and specifically inhibiting a protein-protein interaction in cells (Wojcik et al., 2010).

The ability to generate novel binding proteins capable of interacting with other proteins with high-affinity and/or specificity is important in biotechnology, medicine and molecular biology. Such designer binding proteins can be used in numerous applications. They can be used to label a protein of interest for detection and visualization, to purify a target protein from a complex mixture or to functionally perturb a target by blocking a functional site. Because of their broad utility, there is a need to develop strategies for producing novel binding proteins quickly and effectively and with improved stability properties. To date, FN3-based binding proteins have been constructed by selections from combinatorial libraries in which loop regions are diversified (Bloom and Calabro, 2009).

SUMMARY OF THE INVENTION

The present application describes various compositions and methods for the production and use of FN3-based binding proteins with improved stability properties. Aspects of the disclosure relate to polypeptides comprising a variant fibronectin type III (FN3) domain from *Sulfolobus tokodaii* that includes one or more amino acid substitutions or insertions in a loop region of FN3, in a non-loop region of FN3, or in both.

In some embodiments, a polypeptide comprises a non-variant FN3 domain. In particular embodiments, the non-variant FN3 domain comprises at least 70% identity to SEQ ID NO:1. In some embodiments, the non-variant FN3 domain comprises SEQ ID NO:1. In further embodiments, the non-variant FN3 domain comprises a polypeptide with at least 70% identity to SEQ ID NO:2 (STOFN3-2), 3 (STOFN3-3), or 4 (STOFN3-4). In some embodiments, the non-variant FN3 domain comprises SEQ ID NO:2, 3, or 4. In some embodiments, the amino acid substitution comprises one or more substitutions of the FN3 domain corresponding to amino acid positions 1, 2, and 3 of SEQ ID NO:1. In some embodiments, the amino acid substitutions at one or more positions corresponding to amino acid positions 1, 2, and/or 3 of SEQ ID NO:1 are a substitution with a hydrophilic amino acid or combinations thereof. In some embodiments, the amino acid insertion comprises one or more amino acid insertions of the FN3 domain after the amino acid corresponding to amino acid position 84 of SEQ ID NO:1. In some embodiments, the amino acid insertion comprises 1-3 amino acids. In some embodiments, the inserted amino acids are proline and serine or combinations thereof. In some embodiments, the substitution comprises one or more substitutions of the FN3 domain corresponding to amino acid positions 4, 14, 28, and 58 of SEQ ID NO:1. In some embodiments, the substitution corresponding to amino acid position 4 of SEQ ID NO:1 is with a valine. In some embodiments, the substitution corresponding to amino acid position 14 of SEQ ID NO:1 is with a proline. In some embodiments, the substitution corresponding to amino acid position 28 of SEQ ID NO:1 is with a tyrosine. In some embodiments, the substitution corresponding to amino acid position 58 of SEQ ID NO:1 is with a proline. In some embodiments, the one or more amino acid substitutions or insertions is in one or more of beta strand C or beta strand D. In some embodiments, the one or more amino acid substitutions or insertions correspond to or after positions 28, 29, 30, 31, 32, 33, 34, or 35 of SEQ ID NO:1. In some embodiments, the one or more amino acid substitutions or insertions correspond to or after positions 38, 39, 40, 41, 42, 43, 44, 45, or 46 of SEQ ID NO:1. In some embodiments, the one or more amino acid substitutions or insertions in the loop region of FN3 are in the BC loop, DE loop, FG loop and/or CD loop. In some embodiments, the DE loop does not comprise any inserted amino acids. In some embodiments, the EF loop comprises less than 3 substitutions or insertions. In some embodiments, the FN3 domain does not have substitutions at amino acid positions corresponding to positions 69 and 77 of SEQ ID NO:1. In some embodiments, the polypeptide further comprises a non-FN3 polypeptide that enhances the FN3 polypeptide binding affinity for a target molecule. In some embodiments, the polypeptide comprises or further comprises an insertion or deletion of at least 1 amino acids in at least one loop region of FN3. In some embodiments, at least one loop region of FN3 comprises an insertion of at least 2 amino acids. In some embodiments, at least one region of FN3 comprises an insertion of 2 to 25 amino acids in at least one loop region. In some embodiments, at least two loop regions comprise an insertion. In some embodiments, at least one loop region of FN3 comprises a deletion of at least 1 amino acid. In some embodiments, at least one loop region of FN3 comprises a deletion of 2 to 10 amino acids. In some embodiments, at least two loop regions comprise a deletion of at least 1 amino acid. In some embodiments, the polypeptide comprises at least 1 amino acid insertion and 1 amino acid deletion in at least one loop region. In some embodiments, the polypeptide comprises an insertion and deletion of at least 1 amino acid in the same loop region. In some embodiments, the polypeptide further comprises one or more serine residues immediately before amino acid 1 or immediately after amino acid 84 of SEQ ID NO:1.

In certain aspects, the insertion, deletion, or substitution, when described with respect to an amino acid at a position in SEQ ID NO:1 may be the corresponding amino acid at a corresponding position in SEQ ID NO:2, 3, and/or 4. The corresponding positions are those that are aligned with the amino acid in SEQ ID NO:1 in FIG. 1.

In some embodiments, the AB, BC, CD, DE, EF, and/or FG loop or A, B, C, D, E, F, or G beta-strand may have at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid substitutions, insertions and/or deletions (or combinations thereof). In certain aspects, beta strand variations can be used in conjunction with variations in the AB loop, the BC loop, the CD loop, the DE loop, and/or the FG loop of FN3 to generate a polypeptide library or a nucleic acid library encoding the same. FN3 polypeptides can be modified by inserting or deleting 1, 2, 3, 4, 5, 6, 7, 8, 9, 10, 20 or more amino acids, or any range derivable therein, in a FN3 loop. In certain aspects, variations in loops AB, CD, and EF may be specifically excluded from invention, either individually or in various combinations. In some embodiments it is contemplated that an FN3 variant does not include a substitution, insertion and/or deletion in a bottom loop (loop AB, CD, EF). In further embodiments modifications in the bottom loop(s) is limited to 1, 2, 3, 4, or 5 or fewer substitutions, insertions, and/or deletions.

In certain embodiments, polypeptides comprise a variant fibronectin type III (FN3) domain comprising one or more amino acid substitutions in both a loop region of FN3 and in a non-loop region of FN3. In certain aspects, the one or more amino acid substitution in the non-loop segment is one or more substitution in beta strand C, beta strand D, beta strand F, and/or beta strand G.

In certain embodiments, the polypeptide can comprise 1, 2, 3, 4 or more insertions and/or deletions of amino acids corresponding to amino acids of SEQ ID NO:1. Insertions can include, but are not limited to stretches of poly-serine, poly-alanine, poly-valine, poly-threonine, or polymers of any other of the 20 amino acids, that is subsequently mutagenized or diversified for generating a combinatorial polypeptide library. Diversification of these inserted residues can include alteration to 1, 2, 3, 4, 5, 6, 7, 8, 9, 10, 11, 12, 13, 14, 15, 16, 17, 18, or 19 of the other natural amino acids. In certain aspects 1, 2, 3, 4, 5, 6, 7, 8, 9, 10, 11, 12, 13, 14, 16, 17, 18, 19, 20, 21, 22, 23, 24, 25 or more contiguous amino acids are inserted into one or more of the AB, BC, CD, DE, EF, FG loops of a FN3 domain polypeptide. In a further aspect, the polypeptide can comprise an insertion, a deletion, or both an insertion and a deletion. The insertion and/or deletion can be at the beginning and/or end of the polypeptide. The insertion and deletion need not be located at the same position and may be located at sites distal or proximal to each other. The insertion and/or deletion can be in a loop or non-loop portion of the FN3 domain polypeptide. In certain aspects, at least one loop region of FN3 comprises an insertion of at least 2 amino acids. In a further aspect, at least one region of FN3 comprises an insertion of 2 to 25 amino acids in at least one loop region. In certain aspects at least 2, 3, or more loop regions comprise an insertion. In certain aspects, the polypeptide has at least one loop region of FN3 comprises a deletion of at least 1, 2, 3, 4, 5, 6, 7, 8, 9, or 10 amino acids, including all values and ranges there between. In certain aspects, at least 2, 3, or 4 loop or non-loop segments, portions, or regions comprise a deletion of at least 1 amino acid. In certain aspects, the polypeptide comprises at least one insertion and one deletion in at least one loop or non-loop region. In a further aspect, the polypeptide comprises an insertion and a deletion in the same loop or non-loop region. The term region indicates the amino acids of a particular structural segment of the polypeptide as defined by secondary structure and/or crystal structure corresponding to the amino acids of SEQ ID NO:1 or its variants.

Further aspects relate to a polypeptide comprising a variant fibronectin type III (FN3) domain from *Pyrococcus horikoshii* comprising one or more amino acid substitutions or insertions in a loop region of FN3, in a non-loop region of FN3, or in both. In some embodiments, the non-variant FN3 domain comprises at least 70% identity to SEQ ID NO:6. In some embodiments, the non-variant FN3 domain comprises SEQ ID NO:6. In some embodiments, the one or more amino acid substitutions or insertions in the non-loop segment is in one or more of beta strand C or beta strand D. In some embodiments, the one or more amino acid substitutions or insertions correspond to or after positions 13 and/or 14 of SEQ ID NO:6. In some embodiments, the one or more amino acid substitutions or insertions correspond to or after positions 20, 21, 22, 23, 24, 25, 26, and/or 27 of SEQ ID NO:6. In some embodiments, the one or more amino acid substitutions or insertions correspond to or after positions 36 and/or 37 of SEQ ID NO:6. In some embodiments, the one or more amino acid substitutions or insertions correspond to or after positions 40, 41, 42, 43, 44, 45, 46, 47, and/or 48 of SEQ ID NO:6. In some embodiments, the one or more amino acid substitutions or insertions correspond to or after positions 54, 55, 56, 57, 58, and/or 59 of SEQ ID NO:6. In some embodiments, the one or more amino acid substitutions or insertions correspond to or after positions 67, 68, 69, 70. 71, 72, 73, and/or 74 of SEQ ID NO:6. In some embodiments, the one or more amino acid substitutions or insertions in the loop region of FN3 are in the AB loop, BC loop, CD loop, DE loop, EF loop, and/or FG loop. In some embodiments, the polypeptide further comprises a non-FN3 polypeptide that enhances the FN3 polypeptide binding affinity for a target molecule. In some embodiments, the polypeptide further comprises an insertion or deletion of at least 1 amino acids in at least one loop region of FN3. In some embodiments, at least one loop region of FN3 comprises an insertion of at least 2 amino acids. In some embodiments, at least one region of FN3 comprises an insertion of 2 to 25 amino acids in at least one loop region. In some embodiments, at least two loop regions comprise an insertion. In some embodiments, at least one loop region of FN3 comprises a deletion of at least 1 amino acid. In some embodiments, at least one loop region of FN3 comprises a deletion of 2 to 10 amino acids. In some embodiments, at least two loop regions comprise a deletion of at least 1 amino acid. In some embodiments, the polypeptide comprises at least 1 amino acid insertion and 1 amino acid deletion in at least one loop region. In some embodiments, the polypeptide comprises an insertion and deletion of at least 1 amino acid in the same loop region.

In certain aspects, the polypeptide is at least or at most 50, 55, 60, 65, 70, 75, 80, 85, 91, 92, 93, 94, 95, 96, 97, 98, 99, or 100% identical (or any derivable range therein) to a polypeptide sequence of the disclosure, including any of SEQ ID NOS:1-4 or 6.

In some embodiments, the polypeptide is isolated, recombinant, a non-natural polypeptide, engineered, and/or synthetic.

In some embodiments, the polypeptides of the disclosure bind specifically to a site on a target motif. In some embodiments, the polypeptides of the disclosure specifically bind a target motif. In some embodiments, the polypeptide further comprises a polypeptide comprising a biorecognition module including a molecular recognition domain; wherein the polypeptide comprising the biorecognition molecule and the polypeptide comprising the variant FN3 domain are operatively linked together either directly or indirectly via the linker, and are spatially oriented to bind the same, overlapping, or distinct sites on the target motif. In some embodiments, the polypeptide comprising the biorecognition molecule and the polypeptide comprising the variant FN3 domain bind overlapping sites on the target motif at the same time and are capable of forming a complex with the target motif. In some embodiments, the Kd for the polypeptide being equal to or lower than one µM. In some embodiments, the target motif is a peptide, a phosphorylated peptide or a methylated peptide. In some embodiments, the peptide is present within a protein. In some embodiments, the molecular recognition domain comprises an interaction domain or mutants of interaction domains. In some embodiments, the interaction domain is selected from the group consisting of PDZ, WW, SH2, PTB, SH3, Bromo, Chromo, PHD, Polobox and FHA domains. In further embodiments, the polypeptide comprising the variant FN3 domain further comprises a first signaling moiety and the polypeptide comprising the biorecognition molecule further comprises a second signaling moiety and wherein the first and second signaling moieties are capable of interacting to produce a detectable signal. In some embodiments, the signaling moiety is a dye, a quencher, a reporter protein, or a quantum dot. In some embodiments, the first and second signaling moieties comprise a fluorescent resonance energy transfer (FRET) donor group and a FRET acceptor group, respectively, and binding of the first and second molecular recognition domains to the target motif results in a change in the FRET efficiency between the FRET donor and FRET acceptor groups.

The polypeptides of the invention can be comprised in a polypeptide library or encoded in a polynucleotide library that can be screened for particular polypeptide characteristics, e.g., biding affinity. One or more members of the library can then isolated from other members of the library and analyzed. In certain aspects the library comprises or encodes a plurality of those polypeptides described herein. In certain aspects, the polypeptide library is pre-selected to bind a target and those preselected members are then further diversified in selected amino acid position to generate a targeted library that is subsequently screened for a particular characteristic or property.

Certain aspects relate to a polypeptide library comprising a plurality of modified FN3 domain polypeptides comprising one or more amino acid substitutions, insertions, or deletions a loop region of FN3, in a non-loop region of FN3, or in both; wherein the unmodified FN3 domain comprises a polypeptide comprising the amino acid sequence of SEQ ID NOS:1-4 or 6. In some embodiments, the FN3 domain polypeptides comprises one or more amino acid substitutions corresponding to amino acid positions corresponding to positions 1, 2, 3, 4, 14, 28, and/or 58 of SEQ ID NO:1.

Certain aspects are directed to polynucleotides encoding one or more polypeptide described herein. In certain embodiments the polynucleotide is an expression cassette or an expression construct. The expression construct can be capable of expressing the encoded polypeptide in a host cell, such as a prokaryotic or eukaryotic cell line or strain. In certain aspects the expression construct is functional in one or more polypeptide expression systems known in the art. In a further aspect, the expression construct is functional in bacteria, yeast, insect cells or the like.

The polypeptide can further comprise a second FN3 domain that may or may not have been selected for affinity to a particular target. The second FN3 domain may or may not contain additional amino acid variations or diversification. In other aspects, the polypeptide can further comprise a non-FN3 polypeptide that enhances the FN3 polypeptide binding affinity for a target molecule. The non-FN3 polypeptide can include, but is not limited to domains involved in phospho-tyrosine binding (e.g., SH2, PTB), phosphoserine binding (e.g., UIM, GAT, CUE, BTB/POZ, VHS, UBA, RING, HECT, WW, 14-3-3, Polo-box), phosphothreonine binding (e.g., FHA, WW, Polo-box), proline-rich region binding (e.g., EVH1, SH3, GYF), acetylated lysine binding (e.g., Bromo), methylated lysine binding (e.g., Chromo, PHD), apoptosis (e.g., BIR, TRAF, DED, Death, CARD, BH), cytoskeleton modulation (e.g., ADF, GEL, DH, CH, FH2), or other cellular functions (e.g., EH, CC, VHL, TUDOR, PUF Repeat, PAS, MH1, LRR1 IQ, HEAT, GRIP, TUBBY, SNARE, TPR, TIR, START, SOCS Box, SAM, RGS, PDZ, PB1, LIM, F-BOX, ENTH, EF-Hand, SHADOW, ARM, ANK).

In certain aspects, variants in any one or more of positions that correspond with amino acid position 13, 14, 15, 16, 22, 23, 24, 25, 26, 27, 36, 37, 47, 48, 49, 54, 55, 56, 57, 58, 59, 60, 71, 72, 73, 74, 75, 76, 77, 78, 79 and/or 80 of SEQ ID NO:1, including all ranges there between, can be specifically included in the claimed embodiments.

In other embodiments, variants in any one or more of positions that correspond with amino acid positions 13, 14, 20, 21, 22, 23, 24, 25, 26, 27, 36, 37, 40, 41, 42, 43, 44, 45, 46, 47, 48, 54, 55, 56, 57, 58, 59, 67, 68, 69, 70, 71, 72, 73 and 74 of SEQ ID NO:6, including all ranges there between, can be specifically included in the claimed embodiments.

In some embodiments, the polypeptide library comprises domain polypeptides are at least 50%, 60%, 70%, 80%, or 90% identical to SEQ ID NO:1, 2, 3, 4, or 6.

In some embodiments, the length of the polypeptide is at least, at most, or exactly about 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 625, 650, 675, 700, 750, 800, or 900 amino acids (or any derivable range therein). In some embodiments, the polypeptide is truncated or not full length.

In some embodiments, the polypeptide library further comprises a non-FN3 polypeptide that enhances the FN3 polypeptide binding affinity for a target molecule. In some embodiments, the polypeptide library further comprises an insertion or deletion of at least 1 amino acids in at least one loop region of the FN3 domain polypeptides. In some embodiments, at least one loop region of FN3 comprises an insertion of at least 2 amino acids. In some embodiments, at least one region of FN3 comprises an insertion of 2 to 25 amino acids in at least one loop region. In some embodiments, at least two loop regions comprise an insertion. In some embodiments, at least one loop region of FN3 comprises a deletion of at least 1 amino acid. In some embodiments, at least one loop region of FN3 comprises a deletion of 2 to 10 amino acids. In some embodiments, at least two loop regions comprise a deletion of at least 1 amino acid. In some embodiments, the polypeptide comprises at least 1 amino acid insertion and 1 amino acid deletion in at least one loop region. In some embodiments, the FN3 domain polypeptides comprise an insertion and deletion of at least 1 amino acid in the same loop region. In some embodiments, the library is pre-selected to bind a target.

Certain embodiments are directed to a monobody library comprising a plurality of polypeptides having a variant fibronectin type III (FN3) domain, compared to wildtype (SEQ ID NO:1-4 or 6), comprising one or more alterations or variants in a beta strand or a loop region. In some embodiments, the alterations are in one or more of beta strand C, beta strand D, BC loop, CD loop, DE loop, or and/or FG loop. In some embodiments, the monobody comprises one or more of the variant amino acids corresponding to position 1, 2, 3, 4, 14, 28, and/or 58 of SEQ ID NO:1. In some embodiments, the variant FN3 domains further comprise an insertion, substitution, or deletion of at least 1, 2, 3, 4, 5, 6, 7, 8, 9, 10, 15, 20, 25 amino acids in at least one loop region of FN3.

The monobody library can also comprise variant FN3 domains comprising an amino acid insertion in loop FG. The monobody library can also comprise a plurality of those polypeptides described above.

Certain embodiments include methods of making a polypeptide or polynucleotide library comprising a plurality of FN3 variants. In certain aspects the library can contain 10, 100, 1000, 104, 105, 106, 107, 108, 109, 1010, 1011, 1012, 1013, 1014, 1015 or more different polypeptide or polynucleotide variants, including all values and ranges there between, though it will be understood that there may be duplicate variants. The methods of making such a polypeptide or polynucleotide include the engineering of various amino acids substitutions, deletions, and/or insertion described herein.

Certain embodiments include methods of selecting one or more FN3 variants comprising conducting one or more binding assays using a FN3 library having a plurality of different FN3 variants. In certain aspects the library can comprise FN3 polypeptides having amino acid variations in the FN3 loops, FN3 beta-strands, or both FN3 loops and beta-strands. After conducting the binding assay(s) one or more FN3 variants are selected that have a particular property, such as binding specificity and/or binding affinity to a target. In certain aspects, the amino acid or nucleic acid sequence of one or more of the selected library members can be determined using conventional methods. The sequence of the selected FN3 polypeptide(s) can then be used to produce a second library that introduces further variation of the selected sequences. The second library can then be screened for FN3 polypeptides having a particular property. The process can be repeated 1, 2, 3, 4, 5, 6, 7, 8, 9, 10 or more times. Additional iterations would enrich the library as well as potentially include other variants. In certain aspects the method for selecting a protein binding domain specific for a target comprises (a) detecting target specific binding of one or more members of a polypeptide library comprising a plurality of FN3 domain polypeptides as described herein; and (b) selecting the protein binding domain that specifically binds the target. The method can further comprise first preparing the plurality of FN3 domain polypeptide variants described herein. A polypeptide identified as exhibiting a particular characteristic can be isolated. In certain aspects, the method can further comprise determining the nucleic acid and/or the amino acid of sequence of the selected protein binding domain. The selected protein binding domain can then be synthesized or expressed.

Methods can further comprise conducting a first screen of a library having amino acid variations in only FN3 loops or only FN3 beta strands and conducting a second screen using variations in only FN3 loops or only FN3 beta strands. In certain aspects the first screen uses only variations in the FN3 loops and the second screen only uses variations in the FN3 beta-strands. In a further aspect, the second screen can use variations in both FN3 loops and beta-strands. In certain aspects, the FN3 amino acid residues varied in the first screen are or are not varied in the second screen.

Further aspects include methods of identifying a polypeptide that specifically binds a target comprising detecting specific binding of one or more polypeptides of a polypeptide library, the library comprising a plurality of fibronectin type III (FN3) polypeptides as described herein.

Further aspects include methods of detecting a target molecule comprising contacting a sample containing the target with a fibronectin type III (FN3) binding domain that specifically binds the target.

Yet further aspects relate to a method of making a polypeptide or polypeptide library according to the disclosure, the method comprising expressing a polynucleotide of the disclosure or a polynucleotide encoding such polypeptide in a host cell.

Certain aspects include methods of producing a fibronectin type III (FN3) variant comprising: (a) expressing a polypeptide comprising an amino acid sequence; and (b) isolating and/or purifying the expressed variant FN3 domain from a host cell expressing the variant FN3.

Certain embodiments are directed to kits. In certain aspects, a kit can comprise a plurality of polypeptides as described herein. In a further aspect, a kit can comprise a plurality of polynucleotides encoding FN3 domain variants as described herein.

Further aspects of the disclosure relate to methods for testing a polypeptide according to the embodiments described herein, the method comprising contacting the polypeptide with a target molecule and testing for binding activity between the polypeptide and the target molecule.

The term "fibronectin type III domain" or "FN3 domain" refers to a domain (region) from a wild-type fibronectin from any organism.

The term "fibronectin type III domain variant" or "FN3 variant domain" refers to a polypeptide region in which one or more amino acid substitutions, deletions, and/or insertions are present as compared to the amino acid sequence of a wildtype FN3 domain. In certain embodiments, the FN3 variant or FN3 variant domain has an alteration with respect to specifically the fibronectin type III domain of SEQ ID NO:1-4 or 6. The term "substitutional variant" includes the replacement of one or more amino acids in a peptide sequence with a conservative or non-conservative amino acid(s). In some embodiments, the FN3 domain variant has increased binding properties compared to the wildtype FN3 domain relative to a particular target.

The term "FN3-domain polypeptide" refers to a polypeptide that includes at least one FN3 domain. A "variant FN3 domain polypeptide" refers to a polypeptide that includes at least one variant FN3 domain. It is contemplated that such polypeptides are capable of specifically binding a polypeptide or protein.

A "non-FN3 binding sequence" refers to an amino acid sequence of more than 15 contiguous amino acid residues that is not present in an FN3 domain or an FN3 domain variant and that specifically binds to a protein or polypeptide. In some embodiments, a non-FN3 binding sequence is specifically a non-tenth module fibronectin type III domain binding sequence.

The β sheet is a form of regular secondary structure in proteins. Beta sheets consist of beta strands connected laterally by at least two or three backbone hydrogen bonds, forming a generally twisted, pleated sheet. A beta strand (also β strand) is a stretch of polypeptide chain typically 3 to 10 amino acids long with backbone in an almost fully extended conformation. A loop is a less ordered, flexible stretch of amino acids (as compared to alpha helices and beta sheets) that typically connect other structural elements of a protein. In the context of FN3, the loops are designated by the beta-strands they connect, for example the loop connecting beta-strand A and beta-strand B is the AB loop.

Beta strand A refers to the amino acids preceding the AB loop

Beta strand B refers to the amino acids connecting the AB and BC loops

Beta strand C refers to the amino acids connecting the BC and CD loops.

Beta strand D refers to the amino acids connecting the CD and DE loops.

Beta strand E refers to the amino acids connecting the DE and EF loops.

Beta strand F refers to the amino acids connecting the EF and FG loops.

Beta strand G refers to the amino acids after the FG loop.

The term "binding protein" refers to a polypeptide that specifically binds another compound, such as a polypeptide through non-covalent chemical interactions.

As used herein, "monobody" is intended to mean a polypeptide having a sequence and structure related to the tenth module of the fibronectin type III domain (FN3) that includes a beta-strand domain lacking in disulfide bonds and containing a plurality of beta-strands, two or more loop regions each connecting one beta-strand to another beta-strand, and optionally an N-terminal tail, a C-terminal tail, or both, wherein at least one of the two or more loop regions, the N-terminal tail, and or the C-terminal tail is characterized by activity in binding a target protein or molecule. More specifically, in some embodiments such monobodies can include three or more loop regions or, even more specifically, four or more loop regions. The size of such polypeptide monobodies is preferably less than about 30 kDa, more preferably less than about 20 kDa.

The term "library" refers to a collection (e.g., to a plurality) of polypeptides having different amino acid sequences and different protein binding properties. In some embodiments there is a variant FN3 domain library comprising polypeptides having different variations of the FN3 domain. Unless otherwise noted, the library is an actual physical library of polypeptides or nucleic acids encoding the polypeptides. In further embodiments, there is a database that comprises information about a library that has been generated or a theoretical library that can be generated. This information may be a compound database comprising descriptions or structures of a plurality of potential variant FN3 domains. "FN3-based molecule" refers to a molecule having an amino acid sequence of an FN3 domain or FN3 variant domain.

The term "specifically binds" or "specific binding" refers to the measurable and reproducible ability of an FN3-based molecule to bind another molecule (such as a target), that is determinative of the presence of the target molecule in the presence of a heterogeneous population of molecules including biological molecules. For example, an FN3-based molecule that specifically or preferentially binds to a target is a polypeptide that binds this target with greater affinity, avidity, more readily, and/or with greater duration than it binds to most or all other molecules. "Specific binding" does not necessarily require (although it can include) exclusive binding.

An polypeptide that specifically binds to a target with an affinity of at least $1 \times 10^{-6}$ M at room temperature under physiological salt and pH conditions, as measured by surface plasmon resonance.

The term "non-natural amino acid residue" refers to an amino acid residue that is not present in the naturally occurring FN3 domain in a mammal, such as a human. The term "non-natural polypeptide" refers to a polypeptide that is not wild-type and/or not found in nature.

The terms "tag", "epitope tag" or "affinity tag" are used interchangeably herein, and usually refers to a molecule or domain of a molecule that is specifically recognized by an antibody or other binding partner. The term also refers to the binding partner complex as well. Thus, for example, biotin or a biotin/avidin complex are both regarded as an affinity tag. In addition to epitopes recognized in epitope/antibody interactions, affinity tags also comprise "epitopes" recognized by other binding molecules (e.g., ligands bound by receptors), ligands bound by other ligands to form heterodimers or homodimers, His6 bound by Ni-NTA, biotin bound by avidin, streptavidin, or anti-biotin antibodies, and the like.

Epitope tags are well known to those of skill in the art. Moreover, antibodies specific to a wide variety of epitope tags are commercially available. These include but are not limited to antibodies against the DYKDDDDK epitope, c-myc antibodies (available from Sigma, St. Louis), the HNK-1 carbohydrate epitope, the HA epitope, the HSV epitope, the His4, His5, and His6 epitopes that are recognized by the His epitope specific antibodies (see, e.g., Qiagen), and the like. In addition, vectors for epitope tagging proteins are commercially available. A polypeptide can be tagged with the FLAG® epitope (N-terminal, C-terminal or internal tagging), the c-myc epitope (C-terminal) or both the FLAG (N-terminal) and c-myc (C-terminal) epitopes.

The term "conjugate" in the context of an FN3-based molecule refers to a chemical linkage between the FN3-based molecule and a non-FN3-based molecule. It is specifically contemplated that this excludes a regular peptide bond found between amino acid residues under physiologic conditions in some embodiments.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

"Biorecognition module" and "recognition module" (used interchangeably), as used herein, refer to a biomolecule which makes up one module of the modular molecular affinity clamp embodying the principles of the invention. A biorecognition module contains a molecular recognition domain that has affinity for a target motif of interest.

"Molecular recognition domain" and "recognition domain", (used interchangeably), as used herein, refer to a binding domain within a biorecognition module that demonstrates an ability to bind to a target motif, i.e., has binding affinity for a target motif.

The terms "target" and "target molecule," as used herein, refer to a peptide, antigen or epitope that specifically binds to an FN3-based binding molecule or monobody described herein, or any biomolecule of interest for which a molecular affinity clamp is sought. Targets include, but are not limited to, epitopes present on proteins, peptides, carbohydrates, and/or lipids. Exemplary targets include, but are not limited to, secreted peptide growth factors, pharmaceutical agents, cell signaling molecules, blood proteins, portions of cell surface receptor molecules, portions of nuclear receptors, steroid molecules, viral proteins, carbohydrates, enzymes, active sites of enzymes, binding sites of enzymes, portions of enzymes, small molecule drugs, cells, bacterial cells, proteins, epitopes of proteins, surfaces of proteins involved in protein-protein interactions, cell surface epitopes, diagnostic proteins, diagnostic markers, plant proteins, peptides involved in protein-protein interactions, and foods. The target may be associated with a biological state, such as a disease or disorder in a plant or animal as well as the presence of a pathogen. When a target is "associated with" a certain biological state, the presence or absence of the target or the presence of a certain amount of target can identity the biological state.

A "target motif", as used herein, refers to any portion or sequence of a target of interest for which a molecular affinity clamp is sought, e.g., refers to a pattern of amino acid residues which is recognized by particular recognition domains. In accordance with the invention, the target motif can bind more than one recognition domain. In other words, a target motif is one to which an affinity clamp embodying the principles of the invention can bind with high affinity and specificity. Of particular importance are target motifs that are short peptides of about 2-100 amino acid residues, especially those of 3-10 amino acid residues. A target motif may be, be at least, or be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 residues in length (or any range derivable therein), which may or may not be contiguous. A target motif may include 1, 2, 3, 4, 5 or more noncontiguous residues and/or regions of residues that may be, be at least, or be at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 residues in length (or any range derivable therein).

As used herein, the term "binds" in connection with the interaction between a target motif and a recognition domain indicates that the recognition domain associates with (e.g., interacts with or complexes with) the target motif to a statistically significant degree as compared to association with proteins generally (i.e., non-specific binding). Thus, the term "molecular recognition domain" is also understood to refer to a domain that has a statistically significant association or binding with a target motif.

In the context of a recognition domain binding to a target motif, the term "greater affinity" indicates that an affinity clamp binds more tightly than a reference domain, or than the same domain in a reference condition, i.e., with a lower dissociation constant. In particular embodiments, the greater affinity is at least 2-fold.

Also in the context of recognition domain binding to a target motif, the term "altered specificity" indicates that relative binding affinity of an affinity clamp is different from that exhibited by a biorecognition module alone. In other words, "altered binding specificity" may refer to an increased binding constant of the affinity clamp for one target motif without the same level of increase for another target, an unchanged binding constant for one target with a decreased binding constant for another, target or a combination thereof.

The term "linked" refers to any method of functionally connecting peptides, particularly the two modules of the modular affinity clamps embodying the principles of the invention. "Linked" may also refer to non-covalent physical association. The biomolecular modules making up the biorecognition modules of the affinity clamps may be linked directly covalently, e.g., via a peptide linkage, or non-covalently, or indirectly via a linker.

A "linker" or "linker moiety," (used interchangeably) may refer to a peptide sequence of about 30 or more amino acid residues that is configured to associate two biorecognition modules in an orientation that facilitates binding of each module to a target motif. The linker, generally, is bifunctional in that it includes a functionality for linking the first biorecognition module and a functionality for linking the second biorecognition module.

By "binding site" is meant an area or region within a recognition domain where a biomolecule can bind non-covalently, i.e., interact with higher affinity than background interactions between molecules. Binding sites embody particular shapes and often can contain multiple binding pockets present within the binding site. The particular shapes are often conserved within a class of molecules, such as a protein family. Binding sites within a class also can contain conserved structures such as, for example, chemical moieties, the presence of a binding pocket, and/or an electrostatic charge at the binding site or some portion of the binding site, all of which can influence the shape of the binding site. It is noted that a molecular affinity clamp is distinguishable from other protein-based compositions that are multivalent—i.e., bind multiple but separate target motifs that are the same. Moreover, in some embodiments a molecular affinity clamp has one component that specifically binds to a target motif or an amino acid sequence that is distinct, overlapping, or the same as another target motif or amino acid sequence specifically bound by another component in the affinity clamp. The different binding components of a molecular affinity clamp do not compete against one another for binding to a target motif.

By "binding pocket" is meant a specific volume of space within a binding site that is available for occupation by a biomolecule. A binding pocket can often be a particular shape, indentation, groove, or cavity in the binding site. Binding pockets can contain particular chemical groups or structures that are important in the non-covalent binding of another molecule such as, for example, groups that contribute to ionic, hydrogen bonding, or van der Waals interactions between the molecules.

By "orientation" or "oriented," in reference to a biorecognition module bound to a target motif, is meant the spatial relationship of the biorecognition module, and at least some of its constituent atoms, to the atoms of the target motif.

By "assaying" is meant the creation of experimental conditions and the gathering of data regarding a particular result of the experimental conditions. For example, enzymes can be assayed based on their ability to act upon a detectable substrate. A particular target motif, in a test sample, can be assayed based on its ability to bind to a monobody or molecular affinity clamp.

As used herein, the terms "peptide," "polypeptide," and "protein" are used interchangeably and mean polymers of amino acid monomers linked by peptide linkages between carboxyl (COOH) groups and amine (NH2) groups. A peptide may consist entirely of naturally occurring amino acid monomers, non-naturally occurring amino acids, or mixtures thereof. Unless denoted otherwise, whenever an amino acid sequence is represented, it will be understood that the amino acids are in N-terminal to C-terminal order from left to right. The term "polypeptide" may refer to small peptides, larger polypeptides, proteins containing single polypeptide chains, proteins containing multiple polypeptide chains, and multi-subunit proteins.

The term "amino acid", as used herein, refers to any amino acid, natural or non-natural, that may be incorporated, either enzymatically or synthetically, into a polypeptide or protein. Amino acids may also be altered. The term thus encompasses amino acids that have been modified naturally or by interaction. Examples may include, but are not limited to, phosphorylation, glycosylation, methylation, biotinylation, and any covalent and non-covalent additions to a protein that do not result in a change in amino acid sequence.

The term "label" as used herein refers to any tag, marker, or identifiable moiety. The skilled artisan will appreciate that many labels may be used in the methods of the invention. For example, labels include, but are not limited to, affinity tags, fluorophores, radioisotopes, chromogens, dyes, magnetic probes, magnetic particles, paramagnetic particles, electrophoretic molecules and particles, dielectrophoretic particles, phosphorescence groups, chemiluminescent, mobility modifiers, and particles that confer a dielectrophoretic change.

As used herein, the term "modulating" or "modulate" refers to an effect of altering a biological activity, especially a biological activity associated with a particular biomolecule. For example, an agonist or antagonist of a particular biomolecule modulates the activity of that biomolecule, e.g., an enzyme.

As used herein, the term "library" refers to any collection of two or more different polypeptides or proteins. In certain embodiments, a library may be a collection of polypeptides that have been modified to favor the inclusion of certain amino acid residues, or polypeptides of certain lengths.

As used herein, the term "variant" is meant to refer to a polypeptide differing from another polypeptide by one or more amino acid substitutions resulting from engineered mutations in the gene coding the polypeptide.

As used herein in connection with numerical values, the terms "approximately" and "about" are meant to encompass variations of ±20% to ±10% or less of the indicated value.

The terms "inhibiting," "reducing," or "preventing," or any variation of these terms, when used in the claims and/or the specification includes any measurable decrease or complete inhibition to achieve a desired result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any other embodiment discussed herein, and vice versa. Furthermore, compositions and kits can be used to achieve recited methods.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or." It is also contemplated that anything listed using the term "or" may also be specifically excluded.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-C. Sequence alignment and biophysical properties of predicted STOFN3 domains. (a) Alignment of four predicted STOFN3 domains and the homologue FN3 domain of human receptor-type tyrosine-protein phosphatase F (PDB ID: 2DJU). Gaps are denoted as dashes. The human FN3 domain shows the sequence identities of 27, 29, 19 and 18% to STOFN3-1, STOFN3-2, STOFN3-3 and STOFN3-4, respectively. The ranges of the secondary structure of the human FN3 domain are shown below the sequences. Dots indicate the highly conserved residues of FN3 domains reported by Main et al. and Dickinson et al. (Main et al., 1992; Dickinson et al., 1994). Shown are SEQ ID NOS:8-17. (b) Size-exclusion chromatograms of STOFN 3-1 and STOFN3-2. The chromatographs are shown with vertical offsets for clarity. Both STOFN3 domains exhibited a mono-dispersed peak with the calculated molecular weight of ~12 kDa based on the calibration standards (not yet done, will do it). (c) Thermal stability of purified STOFN3-1 and STOFN3-2 monitored by DSF. One representative trace of three technical replicates is shown for each STOFN3 domains. The TM value is the mean of three replicates. The melting curves were measured by heating the samples at a rate of 0.5° C. per 30 seconds.

FIG. 2A-C. The crystal structures of STOFN3-1 (a) and STOFN3-2 (b). For panel (a) and (b), the β-strands are labeled A-G. (c) Superposition of STOFN3-1, STOFN3-2 and FN3fn10 (PDBID: 1FNA). STOFN3-1, STOFN3-2 and FN3fn10 are colored green, cyan and gray, respectively.

FIG. 3A-D. The structures of STOFN3-1 (STOTEMP1) and STOTEMP4 around the N-terminal (a-b) and C-terminal (c) regions. The 2Fo-Fc maps around the N-terminal regions of STOTEMP1 (a) and STOTEMP4 (b) are shown as mesh at the 1.56 level. The N-terminal residues are indicated by green stick models, in which the oxygen and nitrogen atoms are colored red and blue, respectively. The BC-, DE- and FG-loops are colored yellow, pink and red. The low electron density of the segment N-terminal to P316S of STOTEMP4 indicates that this segment is conformationally disordered and dislodged from the folded portion. (c) Superposition of STOTEMP1 and STOTEMP4. STOTEMP1 is colored gray and the C-terminal residues are indicated as gray stick models. The C-terminal residues and A- and F-strands of STOTEMP4 are colored green, and the C-terminal residues are indicated as green stick models. The label of position 399 for STOTEMP1 is shown in parentheses. (d) Structure based alignment of STOFN3-1 with FN3fn10 (PDB ID: 1FNA) and amino acid sequences and melting temperatures of STOFN3-1 mutants. The ranges of the secondary structure of FN3fn10 are shown above the sequences. Mutated residues are colored in red. The mean TM values from three replicates are indicated. Shown are SEQ ID NOS:18-25.

FIG. 4A-C. Schematic drawing of the amino acid sequence of STOFN3-1 in its secondary structure context (a). Loop residues as assigned by the program DSSP are shown in yellow. G342 and Y383 subjected to mutation in this work are also shown in cyan. An arrow marks the site at which poly-Serine residues were inserted. Residues of the β-strands whose side chain forms the hydrophobic core are enclosed in circles with thicker ring. (b)-(c) Amino acid sequences and melting temperatures of STOFN3-1 variants. Mutated residues are colored in red. The mean TM values from three replicates are indicated. FIG. 4B shows SEQ ID NOS:26-41. FIG. 4C shows SEQ ID NOS:42-54.

FIG. 6A-C. therMonobody library designs and generated clones. Amino acid sequences of therMonobodies generated from the loop-only library (a) and the side-and-loop library (b). The locations of diversified residues in the libraries are shown as spheres on the STOTEMP4 structure. "X" denotes a mixture of 30% Tyr, 13% Ser, 10% Gly, 5% Asp, 5% Leu, 5% Pro, 5% Trp and 2.5% each of all pther amino acids except for Cys and Met; "B", a mixture of Ala, Ser, Thr, Asn, Asp and Tyr; "U", a mixture of Ser, Thr, Asn and Tyr; "Z", a mixture of Ala, Glu, Lys and Thr. (c) Binding measurements by yeast surface display of representative therMonobodies for each combination of library and target. The mean fluorescence intensities of yeast cells displaying therMonobodies are plotted as a function of the target concentration. The error indicated are the standard deviations from curve fitting of the 1:1 binding model. FIG. 6A shows SEQ ID NOS:59-71. FIG. 6B shows SEQ ID NOS:72-84.

FIG. 7A-C. Oligomerization state and thermal stability of generated therMonobodies. (a) Size-exclusion chromatograms of therMonobodies. The chromatographs are shown with vertical offsets for clarity. The labels show the identities of analyzed samples. MBPMbL17 and MBPMbS09 exhibited a mono-dispersed peak but appeared to interact with the chromatography media, resulting in late elution. SUMOMbS34 was eluted at the void volume fraction, indicating the large aggregate. (b) Thermal stability of therMonobodies monitored by DSF. The traces of three technical replicates are shown for each therMonobody. The TM value is the mean of three replicates. The melting curves were measured by heating the samples at a rate of 0.5° C. per 30 seconds. (c) Summary of oligomerization state and thermal stability measurements of 24 therMonobodies.

FIG. 8A-C. Affinity clamp using therMonobody. (a) Amino acid sequences of Clamp(Ptpn11_pY580) and STOTEMP4 variants. The monobody segment of Clamp (Ptpn11_pY580) and STOTEMP4 variants are aligned based on structure based alignment of the monobody segment and STOTEMP4. The ranges of the secondary structure of the monobody segment of Clamp(Ptpn11_pY580) are shown below its sequence. Residues grafted to the structurally equivalent positions of STOTEMP4 are shaded in yellow. Mutated residues in STOTEMP4 are colored in red. Linkers are indicated by underlining. Shown in FIG. 8a are SEQ ID NOS:85-93. (b)-(c) pY-peptide binding properties of designed pY-clamps measured by yeast surface display. In panel (b), binding of the designed pY-clamps to the target pY-peptide (Ptpn11_pY580) at the concentration of 0, 100 and 500 nM is shown. In panel (c), binding titration curves and the dissociation constants (KD) of the designed pY-clamps are shown. The mean fluorescence intensities of yeast cells displaying the designed pY-clamp are plotted as a function of the target peptide concentration. The errors shown are the standard deviations from curve fitting of the 1:1 binding model.

DETAILED DESCRIPTION OF THE INVENTION

Figure 4A:
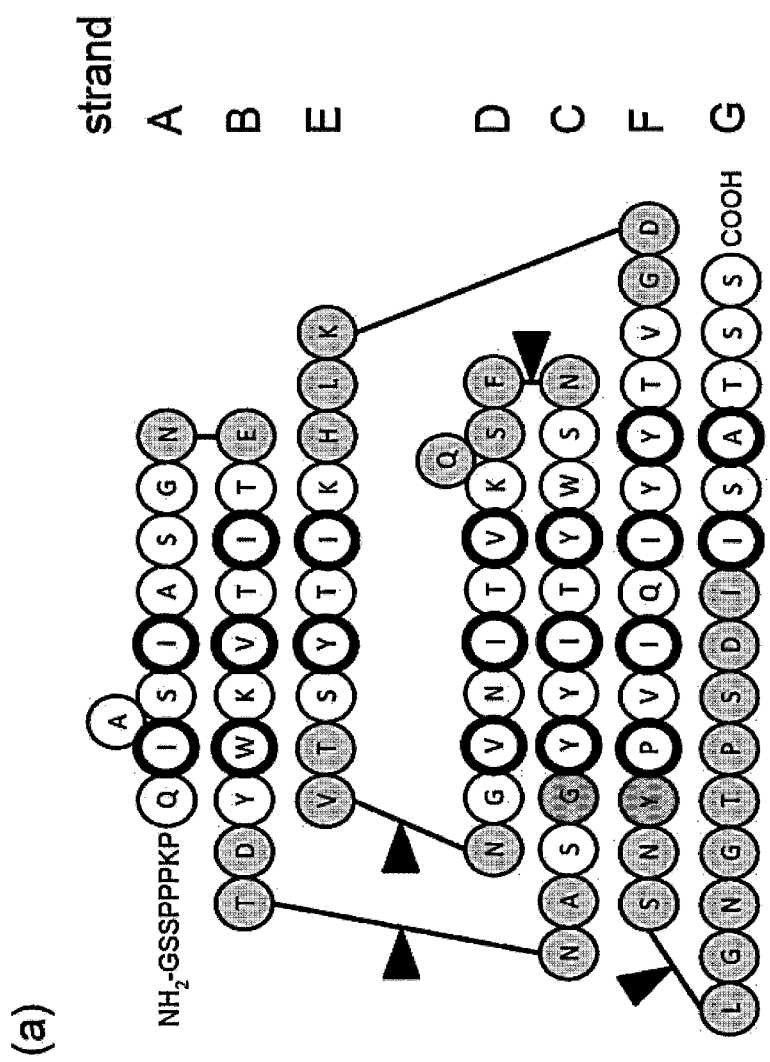

The fibronectin type III domain (FN3) has been particularly successful as a protein scaffold for generating synthetic binding proteins. Since the pioneering work by inventors on the tenth FN3 of human fibronectin (FNfn10), numerous binding proteins, termed monobodies, have been generated to diverse target molecules. To date, all FN3-based scaffolds have been derived from human proteins, primarily because of the prediction that molecules engineered from a human protein may have low immunogenicity, an important consideration in biotherapeutic development. However, immunogenicity concerns are less important in applications where synthetic binding proteins are not exposed directly to patients or consumers including chemical processing and research tools. Therefore, this current application is directed toward the development of a molecular scaffold for industrial applications using FN3's from non-human origins, in particular thermophiles.

IV. Fibronectin Type III (FN3) Domain

A. *Sulfolobus tokodaii*

The inventors utilized the SMART database to explore FN3 domains from hyperthermophiles. The database predicted many FN3 domains in hyperthermophilic archaea and bacteria such as *Thermococcus kodakaraensis, Sulfolobus tokodaii, Pyrococcus horikoshii* and *Thermotoga lettingae*.

The inventors first eliminated predicted domains that were shorter than the length of the shortest FN3 domains that had been structurally characterized (75 amino acids). Then, four predicted FN3 domains in the sequence of Kelch domain-containing protein ST0939 from the hyperthermophilic archaeon *Sulfolobus tokodaii* DSM 16993 were chosen as the candidate proteins, because of their detectably homology to a human FN3. In the predicted constructs, termed STOFN3-1, -2, -3 and -4.

STOFN3-1 comprises 84 amino acids at positions 315-398:

(SEQ ID NO: 1)
PPPKPQIASIASGNETITVKWYDTNASGYYITYWSNFSQKVTINVGNVTS

YTIKHLKDGVTYYIQIVPYNSLGNGTPSDIISAT.

STOFN3-2 comprises 86 amino acids at positions 399-484:

(SEQ ID NO: 2)
PSSVPNPPIIKVKIGNLNATLTWYDTFNGGYPIEGYYLYVNGKGINVGNI

TSYVLTNLTAGELYTIELIAYNKIGNSSISSVSFIA.

STOFN3-3 comprises 79 amino acids at positions 488-566:

(SEQ ID NO: 3)
ANLTVTVYKKINGFLVSWNSTSKAKYILTVSKENVVLLNVSTTNTSYFVK

VPFGVYNISLEAVNIVGITKYAFILIYYI.

STOFN3-4 comprises 76 amino acids at positions 568-643:

(SEQ ID NO: 4)
PASPTVNWSITLNTVSLNWSKVSGAEYYLIYDNGKLITNTTNTAFTENLT

IGQNEIEVYAANAYYKSAPYIINDVR.

Each construct maintains at least two of the three highly conserved hydrophobic amino acids of FN3 domains (FIG. 1A).

The full-length ST0939 comprises the sequence:

(SEQ ID NO: 5)
MKRNTLLALVLVILIFPTLSTAYIEFTTSINQAIPDSLVYATSAYYDGKI

FLIGGENLYSTPVNSVYVYENGSWYLGPSLPFSLSSAGATVCNNTLYVVG

GANSTSIFGGILEFIGNGWKVITNSMPIPVYGAIVFSYDYKIYVIGGMNY

SGNSLVPPVNYIQVYNLKTNSWQIIGNAPLRLAYSAYYFNGSALFVVGGF

TQSATLTSSVFVYYPENNTWISLPSLPGVEAGGVLGYYNGYMYLVGGLYY

VSGAYQLGEILYYYNGTWRNTNIQEQIPTQFSTSVQIGNKLIILGGFGPG

NIPSNAMQTVSIYLPPPKPQIASIASGNETITVKWYDTNASGYYITYWSN

FSQKVTINVGNVTSYTIKHLKDGVTYYIQIVPYNSLGNGTPSDIISATPS

SVPNPPIIKVKIGNLNATLTWYDTFNGGYPIEGYYLYVNGKGINVGNITS

YVLTNLTAGELYTIELIAYNKIGNSSISSVSFIAASKANLTVTVYKKING

FLVSWNSTSKAKYILTVSKENVVLLNVSTTNTSYFVKVPFGVYNISLEAV

NIVGITKYAFILIYYIQPASPTVNWSITLNTVSLNWSKVSGAEYYLIYDN

-continued

```
GKLITNTTNTAFTENLTIGQNEIEVYAANAYYKSAPYIINDVRNYIVVVN

STAISISVPQIKVVSGENTDAPLQTNNIDLKSAIIVITVFVIALLMILVI

LRERSDNYW.
```

In certain aspects, the FN3 domain comprises beta strand A, beta strand B, beta strand C, beta strand D, beta strand E, beta strand F, and beta strand G. Connecting beta strands A, B, C, D, E, F, and G are loop regions AB, BC, CD, DE, EF, and FG. Beta strand A precedes the AB loop and beta strand G follows the FG loop. The loop regions correspond to the following amino acid positions in SEQ ID NO:1—AB (13-16), BC (22-27), CD (36-37), DE (47-49), EF (54-60), and FG (71-80). The loop regions in STOFN3-2, STOFN3-3, and STOFN3-4 are the corresponding amino acids in SEQ ID NO:2, 3, and 4, respectively. The corresponding amino acids can be determined from the alignment of FIG. 1

FN3 polypeptides can be modified by inserting or deleting 1, 2, 3, 4, 5, 6, 7, 8, 9, 10, or more amino acids, or any range derivable therein, in a FN3 loop. Variants are discussed in U.S. Pat. No. 6,673,901, which is hereby incorporated by reference with respect to embodiments regarding FN3 monobodies.

B. *Pyrococcus horikoshii*

The inventors also characterized a FN3 domain in the sequence of putative uncharacterized protein PH0954 from the hyperthermophilic archaeon *Pyrococcus horikoshii* OT3, termed PHOFN3, as the candidate protein, because of its detectably homology to a bacterial FN3 domain in the *Clostridium Perfringens* Glycoside Hydrolase Gh84c whose FN3 fold has been experimentally confirmed. The SMART database predicted PHOFN3 with 108 (P1873-A1980) amino acid residues, but the C-terminal 26 residues (E1955-A1980) did not have detectable homology to the sequence of the bacterial homologue (FIG. 9) and shown below:

```
                                           (SEQ ID NO: 6)
PSPPSGVTLMLNGSYVELSWLPSPDSDVAGYFIYKDGKRLNEVPIEKPNF

RDIYSGTLNYSISAIDFSGFESEKTEVFPVKLEVDEENLTAGYPGAVKVK

VENLDGEA.
```

The full-length PH0954 comprises the sequence:

```
                                           (SEQ ID NO: 7)
MINIKGLILTLILFISLIPPWALGEGSKDTKVFADYYLAGDSVVINATLYDAGSCNLTFSVFS

PIEAPNVSEISFTWMNLSEYIESATEATYGEYLRDGNVIMREDDGYFIYELPFSLNYFGREIK

KIAVNTNGLIELLEEYEEPRIEDYYGIHEEGEFYESDVIFGLDEDLVTYDGYLLLVNLQDKIV

IEWLASTYEDYESEIVDNINFQVIINSNGTITWSYKSLEYSYHDYDLFSGYYSKVSGDVKGFT

KGEGKSFAIQVPLGTPKLYTYQVRESGSYLLTLPLSNYHVEVFANCMDDPDLSNNLAEVGVWP

GDYWVENASINNLIPGEFASINFKVRTTSKIPSAKVKLLRNGVEEKIEYLSFYNGIAEGEISW

LVQGGNYTLALLVEGKGDINSSNNIYLLGNYNFPLPNFEVGNYSIDLPTCVDSTGEVRVNVTS

TANWSIPVRLTLVYEEGNRSYTRYISTKGEEESEVIFTPMIKAGTLEKVVIEIDPWNEVEESN

ESDNKVEVPYHIIEKPDFTVKSLNIPGNVSIGNLYEVNVTLDNLGGCYGRNVLVKLYENGTS

KDWRRVRINNETNVTLTWKPGNAGLVNLTVVVDPYSYVDEINEGNNRLSRLIFVNAPDFKISK

VELLSFDGIAGSKAKFNVTVKNEGEDYSGYFSIAVYGGLRSSIAYLRGIKSGEEKWTIISLPI

NGGNSTLIFVVDPHNVISETNEGNNVIFYNMGYIPKPNFVVKEISLPNNTVGYIPLNITIGNV

GAPYNATSYQVPVKIKTEYGWKVSYLRGIIRDNYTISIDSLAMLPPGSTINVTVNYNMKVNET

SYSDNSLIINYTTGYPDLELGIIPPSGELSAGKDVKITFLVKNVGNATLRIDRSSWYSPYLGL

YVTLEDENGKTHTLGRYELAPATLSPGANISQVVWITLNGGTNKIMGRIVDEYENIYENNNDT

LILTLEKPDFAILNYSIPDEILNGTAYLYKAYPIVLNISNLGGNFSDGIRVDLFDNGIIKTST

SVYGLESGASRDVTLRYLPSSGKHNLSIVLDPYNRWIEENEENNNLTFSLSFGKPDLKVEGIT

WAPYNFTSGENVLFTIYVKNLGQPFLKSFTVRAEIWNGTRKIYSTNAYPRNWSFGKGETKEFN

WRWYNAKPGNLTVKIVVDYYNSIPEGNESNNEFSAFLGNVGTPDFKLENLSVEDLAYGKFVRI

NATVKNLGDSIYRPITVLFNVSGERYYRTVYGIKENESKSVTLPWYVDRVGEVRVKVEVDPGN

RIVEGNESNNIIERTYYVESPELMLSGYEWLEEEVRRGYLAYKVNVTNTGGDVYRGFYVQMFV

DGEPKSSVWINKLLHGETAERTLRWRFSSGGRKEVRIVVDPQDYIPESNEDNNAIVENVTIVL

PDIEVLSLNIPSMHANSYFKVNATIKNSGGQDVKRIFYVSLYQDGKLLGSAPVYSLASGEVKE

VTLTIRPYPGNSTFKVVVDPTNAVVELNEDNNEISVRSYVKAPDIVVVSADLGNFTYPGEMVN

AKVRIRNSGDYKSGVYLLIRNKRRKLGSAYVDSITPGEEIEVNVPWLVDSGDYNVSVIADPYN

SVREWDEENNKLDIEVSVPSPDLTVENITHSGKEVAGEEIIIKVTVKNIGESSKLPFYIVLYA
```

-continued

```
NSSFVGINRVTKIDKGESITLEFKWRASYGEYALRAIVDPYDEVYEENESNNEGMVKVFIEDE
EPPVLKLTYPENGTFTNKPYIGAYLRDEGSGVKFGEIEVYREGTSVPGSTKFSGGWLIFQNST
PLLDGKYTVTVKAVDRAGNEITYSWNFTLDREPPRIVCNLTDGTLYNGTVVPGVQVIDDNLDW
YKVKVNGREFSGPIKLDGTYTLNVTAKDKAGNLAEKIIRFTVNGVPSPPSGVTLMLNGSYVEL
SWLPSPDSDVAGYFIYKDGKRLNEVPIEKPNFRDIYSGTLNYSISAIDFSGFESEKTEVFPVK
LEVDEENLTAGYPGAVKVKVENLDGEANGTLSIILIDEFGNEIEKLSRKVEVPRGRSSHEFVF
MVPRGLTLIRGELKVGNSTARIIHRAKVREGENPEIRVGKLLAGFPGLVEVEIRNCGIVELNT
SETLMKLDNSSGELIEAPLTIPPGKKTVLRYKIVPPKKGSYNLTFRIADVEVRKIVNVSESVL
NPITISTENFIKGGKAKIYVSFRNIGSAPIFVKSIELNGMSKRLSIELPPNLSVEESFEYLIS
EENVEINATVNTDVGKFRKSLTLTAEQPEYNADVSVSSVYEVGKEILITGVAYNESGMLSNVP
VKVSIARGGFVREYIVTTNENGYFNLTFRPFKGESGHFIVSATHPKIELLERDAEFDVVGIEV
IPSLYLLTVPVEFNGTVRVRLINYWRASDVSVSVKAPPEYEVSIPKVLHLKPGSNIINIGLSS
KNAVNGSIMITFKARQLGLNITRSLTLKLKVLPPAPAIVTSPNFLDVGVLTNETASAEVVVRN
LGFTALRNVSIRSSIPWVKVVSNFTEVDPKDNESISLYIEPPRNVTGTFKGEITISSSNYNPI
KVPMRIRVTPNATGGVKVTVMDPNATRLENVKLTLYNGYFHFEGYTNKNGTLEVENVPIGEYK
LFASLEGYYGYSTSITIEVGVEKNVSIILTPSILEVEWEVVPVTIQDVYIIKHEMWYSTHVPA
PEIRMEGGDLEVYVDYEKLAEEGMLEFRGQVIVRNTHQYISVYNVTFESGGSHYIDVEFGINR
IDELKPGEAVIVPYVVRIYYSRSPPINPCLHETKVFKLKAGVVCVEEAGKITLKAQRIHQIVV
KPTCKGCWESVFPVAGKLAFMAIAQKVGQALGNIDDTGVLSTLAGEALNNLESLFDAYNAYKA
NPTKENMENYVKTFNSVKANLASLFMFDPVAYQEINSLQLTLIKTPKGDIAGFAVSRTATPVY
ALGMGVGKIENGQLKVDYKKAVNIANGIVLNVMSKMGGALGGIASGVGLLQLLDKAAEDLPPY
IAQLFLNCAICLMRNDCTLPEGEEIRPIQIIASGSLGGYPSMIPSGLAGGGDGGTAVGRFTCG
GLPTVKKSSTSMSCSTCSSEDVVKERVCRLFRESETHDEEEPSNTLHMCVDLVLTIEQRLTFE
RQAFRASLKFTNTNRNYSLENVSVRVIFFDEEGNRVDDKFFVRLDEKAGLSGSSLEPEKTAEM
KWLIIPKVGAAEKFRARYYVMANITARVGSTKLVYETWPAMIEVEPVPQLVLDYVLPSYVFGD
DPYTPEKELPIPFIFGVRVKNVGYGTARKLRIASAQPKIERSNYPGVYIDFKIIGTLVNGKKV
PNSLTIDFGDLNPGESSTAAWLMIAEVSGKFLQYNATFKHSDELGGNETSLIKEVRTHFLIRA
FNNTENDDGMLDFLVDDDGDGKPEKIIDSRGFDYNVLLLNFTEVEEGSMRKIIPEMKTPFWVY
FTVPFKGSVVRSDGKNPMDQWMENGTLHVLDLGTPEFYILKSNQPPIPRIYVKEPVIANETVV
LDGSLSYDPDGSIIAYTWKIGNESFVGDKVSYVFREPGTYNVTLTVRDDKGTESSKTMEIKVY
LGPKFNESLKVEPQWGIVPFNLSITFNVTNVGDVSGEYSYIIKLGNSTIAEGSEIIESGRWKV
INSTVEIRKEGNYTVTANNLSKTVTAYRKVYGNLTENYIKEKDFGHYKSFYWNEFKRDFEGWV
EEALSTIELPKVNFKVLNYFPGNWSLLNYSEMLNITKGWGWINATYARRVRVEGLEEFKYLIV
NVTQLVVLLGNATHELDESPPTLNVTPSSGIYSEIPKIQVRTCDETGITLVWGAVGNYTKEFT
EVESNGTCSTWEGIVPLNIGNNTVAIYAEDEFGNRGNVSLWIYLNPEAPVIYIESPEEKVYNS
REVMINYTVVNHDLVGVVAYLNGELISSNASYSGFIKLDYGWHNFTIYAWDVSYNVSKSVIFR
VNEPPSVDFSWEVDNLTVKFEANASDEDGISKYLWDFGDNESSLLVNPTHTYRKGGRYNVTLT
VWDSYNLSSSISKEVVVFGSSTLTMVKEYSYTKDFGFYNTTSWKDFLKDFEVWVNLTLRNVTL
PLEYFEEIIEVNVENWSLISVEKNLKNDIGEMSAEYERNATIVGIMNYTRVTLKLTQEVILSG
RARKVEDKIPPLVEILFPRNMTYNETIREIKVRATDESGIANVTATINGESLSLEKVNETWIG
```

```
-continued
RVELDDGKYELNVFASDKWGNVGCSTVNFTINRSVKVRIINGTEIVTIPGDIKTRVYFEGDII

VEIVKESLRFKIPSGGTLVIDERGRKDPWLLARINSTIENISKTSRIFEENGKKVHEIRYRIS

ISRGYAILVVPLEGMKVSSIRIIKNGTVTRDEKHGNYYKLSKGYLFIFLSEDPIVEVTLSKIE

KKDIFRVLYYAGIIWERNYLRLKEEFIMKMSNETSQEAIRLHEEAEKYYLKGREYYPRIPSPS

AIYWYAVYMRKAYLTERKALELLSIS.
```

In certain aspects, the FN3 domain comprises beta strand A, beta strand B, beta strand C, beta strand D, beta strand E, beta strand F, and beta strand G. Connecting beta strands A, B, C, D, E, F, and G are loop regions AB, BC, CD, DE, EF, and FG. Beta strand A precedes the AB loop and beta strand G follows the FG loop. The loop regions correspond to the following amino acid positions in SEQ ID NO:6—AB (13-14) BC (20-27), CD (36-37), DE (40-48), EF (54-59), and FG (67-74).

FN3 polypeptides can be modified by inserting or deleting 1, 2, 3, 4, 5, 6, 7, 8, 9, 10, 20 or more amino acids, or any range derivable therein, in a FN3 loop. Variants are discussed in U.S. Pat. No. 6,673,901, which is hereby incorporated by reference with respect to embodiments regarding FN3 monobodies.

C. FN3 Library

A combinatorial library is a collection of diverse compounds generated by either chemical synthesis or biological synthesis by combining a number of chemical "building blocks." For example, a linear combinatorial chemical library such as a polypeptide (e.g., mutein or variant) library is formed by combining a set of chemical building blocks called amino acids in every possible way for a given compound length. Millions of compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop et al., 1994).

Embodiments of the disclosure are directed to a combinatorial library of FN3 domains. In certain aspects, polypeptides of the library include variations of amino acid sequence in one or more of the beta strands or body of the FN3 domains. In certain aspects, the library includes variations of amino acid sequences in one or more loops of the FN3 domains. In still further aspects, the library includes variation in both loops and beta strands of the FN3 domain.

FN3 variants can include alanine substitutions at one or more of amino acid positions. In certain aspects, any of the 19 other amino acids can be substituted for one or more amino acid of SEQ ID NO:1-4 or 6. Substitutions include, but are not limited to conservative substitutions that have little or no effect on the overall net charge, polarity, or hydrophobicity of the protein.

In certain aspects, FN3 domains will have 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, or 50 amino acid substitutions that include, but are not limited to the following FN3 residue substitutions (corresponding to SEQ ID NO:1): K4V, N14P, D58P, G28Y, Y22A, Y22C, Y22D, Y22E, Y22F, Y22G, Y22H, Y22I, Y22K, Y22L, Y22M, Y22N, Y22P, Y22Q, Y22R, Y22S, Y22T, Y22V, Y22W, D23A, D23C, D23E, D23F, D23G, D23H, D23I, D23K, D23L, D23M, D23N, D23P, D23Q, D23R, D23S, D23T, D23V, D23W, D23Y, T24A, T24C, T24D, T24E, T24F, T24G, T24H, T24I, T24K, T24L, T24M, T24N, T24P, T24Q, T24R, T24S, T24V, T24W, T24Y, N25A, N25C, N25D, N25E, N25F, N25G, N25H, N25I, N25K, N25L, N25M, N25P, N25Q, N25R, N25S, N25T, N25V, N25W, N25Y, A26C, A26D, A26E, A26F, A26G, A26H, A26I, A26K, A26L, A26M, A26N, A26P, A26Q, A26R, A26S, A26T, A26V, A26W, A26Y, S27A, S27C, S27D, S27E, S27F, S27G, S27H, S27I, S27K, S27L, S27M, S27N, S27P, S27Q, S27R, S27T, S27V, S27W, S27Y, N47A, N47C, N47D, N47E, N47F, N47G, N47H, N47I, N47K, N47L, N47M, N47P, N47Q, N47R, N47S, N47T, N47V, N47W, N47Y, V48A, V48C, V48D, V48E, V48F, V48G, V48H, V48I, V48K, V48L, V48M, V48N, V48P, V48Q, V48R, V48S, V48T, V48W, V48Y, T49A, T49C, T49D, T49E, T49F, T49G, T49H, T49I, T49K, T49L, T49M, T49N, T49P, T49Q, T49R, T49S, T49V, T49W, T49Y, S71A, S71C, S71D, S71E, S71F, S71G, S71H, S71I, S71K, S71L, S71M, S71N, S71P, S71Q, S71R, S71T, S71V, S71W, S71Y, L72A, L72C, L72D, L72E, L72F, L72G, L72H, L72I, L72K, L72M, L72N, L72P, L72Q, L72R, L72S, L72T, L72V, L72W, L72Y, G73A, G73C, G73D, G73E, G73F, G73H, G73I, G73K, G73L, G73M, G73N, G73P, G73Q, G73R, G73S, G73T, G73V, G73W, G73Y, N74A, N74C, N74D, N74E, N74F, N74G, N74H, N74I, N74K, N74L, N74M, N74P, N74Q, N74R, N74S, N74T, N74V, N74W, N74Y, G75A, G75C, G75D, G75E, G75F, G75H, G75I, G75K, G75L, G75M, G75N, G75P, G75Q, G75R, G75S, G75T, G75V, G75W, G75Y, T76A, T76C, T76D, T76E, T76F, T76G, T76H, T76I, T76K, T76L, T76M, T76N, T76P, T76Q, T76R, T76S, T76V, T76W, T76Y, P77A, P77C, P77D, P77E, P77F, P77G, P77H, P77I, P77K, P77L, P77M, P77N, P77Q, P77R, P77S, P77T, P77V, P77W, P77Y, S78A, S78C, S78D, S78E, S78F, S78G, S78H, S78I, S78K, S78L, S78M, S78N, S78P, S78Q, S78R, S78T, S78V, S78W, S78Y, D79A, D79C, D79E, D79F, D79G, D79H, D79I, D79K, D79L, D79M, D79N, D79P, D79Q, D79R, D79S, D79T, D79V, D79W, D79Y, I80A, I80C, I80D, I80E, I80F, I80G, I80H, I80K, I80L, I80M, I80N, I80P, I80Q, I80R, I80S, I80T, I80V, I80W, I80Y, N36A, N36C, N36D, N36E, N36F, N36G, N36H, N36I, N36K, N36L, N36M, N36P, N36Q, N36R, N36S, N36T, N36V, N36W, N36Y, F37A, F37C, F37D, F37E, F37G, F37H, F37I, F37K, F37L, F37M, F37N, F37P, F37Q, F37R, F37S, F37T, F37V, F37W, F37Y, G28A, G28C, G28D, G28E, G28F, G28H, G28I, G28K, G28L, G28M, G28N, G28P, G28Q, G28R, G28S, G28T, G28V, G28W, G28Y, Y29A, Y29C, Y29D, Y29E, Y29F, Y29G, Y29H, Y29I, Y29K, Y29L, Y29M, Y29N, Y29P, Y29Q, Y29R, Y29S, Y29T, Y29V, Y29W, Y30A, Y30C, Y30D, Y30E, Y30F, Y30G, Y30H, Y30I, Y30K, Y30L, Y30M, Y30N, Y30P, Y30Q, Y30R, Y30S, Y30T, Y30V, Y30W, I31A, I31C, I31D, I31E, I31F, I31G, I31H, I31K, I31L, I31M, I31N, I31P, I31Q, I31R, I31S, I31T, I31V, I31W, I31Y, T32A, T32C, T32D, T32E, T32F, T32G, T32H, T32I, T32K, T32L, T32M, T32N, T32P, T32Q, T32R, T32S, T32V, T32W, T32Y, Y33A, Y33C, Y33D, Y33E, Y33F, Y33G, Y33H, Y33I, Y33K, Y33L, Y33M, Y33N, Y33P, Y33Q, Y33R, Y33S, Y33T, Y33V, Y33W, W34A, W34C, W34D, W34E, W34F, W34G, W34H, W34I, W34K, W34L, W34M, W34N, W34P, W34Q, W34R, W34S, W34T, W34V, W34Y, S35A, S35C, S35D, S35E, S35F, S35G, S35H, S35I, S35K, S35L, S35M, S35N, S35P, S35Q, S35R, S35T, S35V, S35W, S35Y, S38A, S38C, S38D, S38E, S38F, S38G, S38H, S38I, S38K, S38L, S38M, S38N, S38P, S38Q, S38R, S38T, S38V, S38W, S38Y, Q39A, Q39C, Q39D, Q39E, Q39F, Q39G, Q39H, Q39I, Q39K, Q39L, Q39M, Q39N, Q39P, Q39R, Q39S, Q39T, Q39V, Q39W, Q39Y, K40A, K40C, K40D, K40E, K40F, K40G, K40H, K40I, K40L, K40M, K40N, K40P, K40Q, K40R, K40S, K40T, K40V, K40W, K40Y, V41A, V41C, V41D, V41E, V41F, V41G, V41H, V41I, V41K, V41L, V41M, V41N, V41P, V41Q, V41R, V41S, V41T, V41W, V41Y, T42A, T42C, T42D, T42E, T42F, T42G, T42H, T42I, T42K, T42L, T42M, T42N, T42P, T42Q, T42R, T42S, T42V, T42W, T42Y, I43A, I43C, I43D, I43E, I43F, I43G, I43H, I43K, I43L, I43M, I43N, I43P, I43Q, I43R, I43S, I43T, I43V, I43W, I43Y, N44A, N44C, N44D, N44E, N44F, N44G, N44H, N44I, N44K, N44L, N44M, N44P, N44Q, N44R, N44S, N44T, N44V, N44W, N44Y, V45A, V45C, V45D, V45E, V45F, V45G, V45H, V45I, V45K, V45L, V45M, V45N, V45P, V45Q, V45R, V45S, V45T, V45W, V45Y, G46A, G46C, G46D, G46E, G46F, G46H, G46I, G46K, G46L, G46M, G46N, G46P, G46Q, G46R, G46S, G46T, G46V, G46W, and/or G46Y, and combinations thereof. It is contemplated that one or more of these substitutions may be specifically excluded in embodiments described herein.

In still further embodiments other amino acid substitutions can be introduced before, during, or after introduction of those amino acid substitutions listed above. Further substitutions (corresponding to SEQ ID NO:1) include, but is not limited to 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, or 50 of P1A, P1C, P1D, P1E, P1F, P1G, P1H, P1I, P1K, P1L, P1M, P1N, P1Q, P1R, P1S, P1T, P1V, P1W, P1Y, P2A, P2C, P2D, P2E, P2F, P2G, P2H, P2I, P2K, P2L, P2M, P2N, P2Q, P2R, P2S, P2T, P2V, P2W, P2Y, P3A, P3C, P3D, P3E, P3F, P3G, P3H, P3I, P3K, P3L, P3M, P3N, P3Q, P3R, P3S, P3T, P3V, P3W, P3Y, K4A, K4C, K4D, K4E, K4F, K4G, K4H, K4I, K4L, K4M, K4N, K4P, K4Q, K4R, K4S, K4T, K4V, K4W, K4Y, P5A, P5C, P5D, P5E, P5F, P5G, P5H, P5I, P5K, P5L, P5M, P5N, P5P, P5Q, P5R, P5S, P5T, P5V, P5W, P5Y, Q6A, Q6C, Q6D, Q6E, Q6F, Q6G, Q6H, Q6I, Q6K, Q6L, Q6M, Q6N, Q6P, Q6R, Q6S, Q6T, Q6V, Q6W, Q6Y, I7A, I7C, I7D, I7E, I7F, I7G, I7H, I7K, I7L, I7M, I7N, I7P, I7Q, I7R, I7S, I7T, I7V, I7W, I7Y, A8C, A8D, A8E, A8F, A8G, A8H, A8I, A8K, A8L, A8M, A8N, A8P, A8Q, A8R, A8S, A8T, A8V, A8W, A8Y, S9A, S9C, S9D, S9E, S9F, S9G, S9H, S9I, S9K, S9L, S9M, S9N, S9P, S9Q, S9R, S9T, S9V, S9W, S9Y, I10A, I10C, I10D, I10E, I10F, I10G, I10H, I10K, I10L, I10M, I10N, I10P, I10Q, I10R, I10S, I10T, I10V, I10W, I10Y, A11C, A11D, A11E, A11F, A11G, A11H, A11I, A11K, A11L, A11M, A11N, A11P, A11Q, A11R, A11S, A11T, A11V, A11W, A11Y, S12A, S12C, S12D, S12E, S12F, S12G, S12H, S12I, S12K, S12L, S12M, S12N, S12P, S12Q, S12R, S12T, S12V, S12W, S12Y, G13A, G13C, G13D, G13E, G13F, G13H, G13I, G13K, G13L, G13M, G13N, G13P, G13Q, G13R, G13S, G13T, G13V, G13W, G13Y, N14A, N14C, N14D, N14E, N14F, N14G, N14H, N14I, N14K, N14L, N14M, N14P, N14Q, N14R, N14S, N14T, N14V, N14W, N14Y, E15A, E15C, E15D, E15F, E15G, E15H, E15I, E15K, E15L, E15M, E15N, E15P, E15Q, E15R, E15S, E15T, E15V, E15W, E15Y, T16A, T16C, T16D, T16E, T16F, T16G, T16H, T16I, T16K, T16L, T16M, T16N, T16P, T16Q, T16R, T16S, T16V, T16W, T16Y, I17A, I17C, I17D, I17E, I17F, I17G, I17H, I17K, I17L, I17M, I17N, I17P, I17Q, I17R, I17S, I17T, I17V, I17W, I17Y, T18A, T18C, T18D, T18E, T18F, T18G, T18H, T18I, T18K, T18L, T18M, T18N, T18P, T18Q, T18R, T18S, T18V, T18W, T18Y, V19A, V19C, V19D, V19E, V19F, V19G, V19H, V19I, V19K, V19L, V19M, V19N, V19P, V19Q, V19R, V19S, V19T, V19W, V19Y, K20A, K20C, K20D, K20E, K20F, K20G, K20H, K20I, K20L, K20M, K20N, K20P, K20Q, K20R, K20S, K20T, K20V, K20W, K20Y, W21A, W21C, W21D, W21E, W21F, W21G, W21H, W21I, W21K, W21L, W21M, W21N, W21P, W21Q, W21R, W21S, W21T, W21V, W21Y, S50A, S50C, S50D, S50E, S50F, S50G, S50H, S50I, S50K, S50L, S50M, S50N, S50P, S50Q, S50R, S50T, S50V, S50W, S50Y, Y51A, Y51C, Y51D, Y51E, Y51F, Y51G, Y51H, Y51I, Y51K, Y51L, Y51M, Y51N, Y51P, Y51Q, Y51R, Y51S, Y51T, Y51V, Y51W, T52A, T52C, T52D, T52E, T52F, T52G, T52H, T52I, T52K, T52L, T52M, T52N, T52P, T52Q, T52R, T52S, T52V, T52W, T52Y, I53A, I53C, I53D, I53E, I53F, I53G, I53H, I53K, I53L, I53M, I53N, I53P, I53Q, I53R, I53S, I53T, I53V, I53W, I53Y, K54A, K54C, K54D, K54E, K54F, K54G, K54H, K54I, K54L, K54M, K54N, K54P, K54Q, K54R, K54S, K54T, K54V, K54W, K54Y, H55A, H55C, H55D, H55E, H55F, H55G, H55I, H55K, H55L, H55M, H55N, H55P, H55Q, H55R, H55S, H55T, H55V, H55W, H55Y, L56A, L56C, L56D, L56E, L56F, L56G, L56H, L56I, L56K, L56M, L56N, L56P, L56Q, L56R, L56S, L56T, L56V, L56W, L56Y, K57A, K57C, K57D, K57E, K57F, K57G, K57H, K57I, K57L, K57M, K57N, K57P, K57Q, K57R, K57S, K57T, K57V, K57W, K57Y, D58A, D58C, D58E, D58F, D58G, D58H, D58I, D58K, D58L, D58M, D58N, D58P, D58Q, D58R, D58S, D58T, D58V, D58W, D58Y, G59A, G59C, G59D, G59E, G59F, G59H, G59I, G59K, G59L, G59M, G59N, G59P, G59Q, G59R, G59S, G59T, G59V, G59W, G59Y, V60A, V60C, V60D, V60E, V60F, V60G, V60H, V60I, V60K, V60L, V60M, V60N, V60P, V60Q, V60R, V60S, V60T, V60W, V60Y, T61A, T61C, T61D, T61E, T61F, T61G, T61H, T61I, T61K, T61L, T61M, T61N, T61P, T61Q, T61R, T61S, T61V, T61W, T61Y, Y62A, Y62C, Y62D, Y62E, Y62F, Y62G, Y62H, Y62I, Y62K, Y62L, Y62M, Y62N, Y62P, Y62Q, Y62R, Y62S, Y62T, Y62V, Y62W, Y63A, Y63C, Y63D, Y63E, Y63F, Y63G, Y63H, Y63I, Y63K, Y63L, Y63M, Y63N, Y63P, Y63Q, Y63R, Y63S, Y63T, Y63V, Y63W, I64A, I64C, I64D, I64E, I64F, I64G, I64H, I64K, I64L, I64M, I64N, I64P, I64Q, I64R, I64S, I64T, I64V, I64W, I64Y, Q65A, Q65C, Q65D, Q65E, Q65F, Q65G, Q65H, Q65I, Q65K, Q65L, Q65M, Q65N, Q65P, Q65R, Q65S, Q65T, Q65V, Q65W, Q65Y, I66A, I66C, I66D, I66E, I66F, I66G, I66H, I66K, I66L, I66M, I66N, I66P, I66Q, I66R, I66S, I66T, I66V, I66W, I66Y, V67A, V67C, V67D, V67E, V67F, V67G, V67H, V67I, V67K, V67L, V67M, V67N, V67P, V67Q, V67R, V67S, V67T, V67W, V67Y, P68A, P68C, P68D, P68E, P68F, P68G, P68H, P68I, P68K, P68L, P68M, P68N, P68Q, P68R, P68S, P68T, P68V, P68W, P68Y, Y69A, Y69C, Y69D, Y69E, Y69F, Y69G, Y69H, Y69I, Y69K, Y69L, Y69M, Y69N, Y69P, Y69Q, Y69R, Y69S, Y69T, Y69V, Y69W, N70A, N70C, N70D, N70E, N70F, N70G, N70H, N70I, N70K, N70L, N70M, N70P, N70Q, N70R, N70S, N70T, N70V, N70W, N70Y, I81A, I81C, I81D, I81E, I81F, I81G, I81H, I81K, I81L, I81M, I81N, I81P, I81Q, I81R, I81S, I81T, I81V, I81W, I81Y, S82A, S82C, S82D, S82E, S82F, S82G, S82H, S82I, S82K, S82L, S82M, S82N, S82P, S82Q, S82R, S82T, S82V, S82W, S82Y, A83C, A83D, A83E, A83F, A83G, A83H, A83I, A83K, A83L, A83M, A83N, A83P, A83Q, A83R, A83S, A83T, A83V, A83W, A83Y, T84A, T84C, T84D, T84E, T84F, T84G, T84H, T84I, T84K, T84L, T84M, T84N, T84P, T84Q, T84R, T84S, T84T, T84V, T84W, or T84Y or combinations thereof. It is contemplated that one or more of these substitutions may be specifically excluded in embodiments described herein.

In certain aspects, FN3 domains will have 1, 2, 3, 4, 5, 6, 7, 8, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, or 50 amino acid substitutions that include, but are not limited to the following FN3 residue substitutions (corresponding to SEQ ID NO:6): G13A, G13C, G13D, G13E, G13F, G13H, G13I, G13K, G13L, G13M, G13N, G13P, G13Q, G13R, G13S, G13T, G13V, G13W, G13Y, S14A, S14C, S14D, S14E, S14F, S14G, S14H, S14I, S14K, S14L, S14M, S14N, S14P, S14Q, S14R, S14T, S14V, S14W, 514Y, Y15A, W20A, W20C, W20D, W20E, W20F, W20G, W20H, W20I, W20K, W20L, W20M, W20N, W20P, W20Q, W20R, W20S, W20T, W20V, W20Y, L21A, L21C, L21D, L21E, L21F, L21G, L21H, L21I, L21K, L21M, L21N, L21P, L21Q, L21R, L21S, L21T, L21V, L21W, L21Y, P22A, P22C, P22D, P22E, P22F, P22G, P22H, P22I, P22K, P22L, P22M, P22N, P22Q, P22R, P22S, P22T, P22V, P22W, P22Y, S23A, S23C, S23D, S23E, S23F, S23G, S23H, S23I, S23K, S23L, S23M, S23N, S23P, S23Q, S23R, S23T, S23V, S23W, S23Y, P24A, P24C, P24D, P24E, P24F, P24G, P24H, P24I, P24K, P24L, P24M, P24N, P24Q, P24R, P24S, P24T, P24V, P24W, P24Y, D25A, D25C, D25E, D25F, D25G, D25H, D25I, D25K, D25L, D25M, D25N, D25P, D25Q, D25R, D25S, D25T, D25V, D25W, D25Y, S26A, S26C, S26D, S26E, S26F, S26G, S26H, S26I, S26K, S26L, S26M, S26N, S26P, S26Q, S26R, S26T, S26V, S26W, S26Y, D27A, D27C, D27E, D27F, D27G, D27H, D27I, D27K, D27L, D27M, D27N, D27P, D27Q, D27R, D27S, D27T, D27V, D27W, D27Y, D36A, D36C, D36E, D36F, D36G, D36H, D36I, D36K, D36L, D36M, D36N, D36P, D36Q, D36R, D36S, D36T, D36V, D36W, D36Y, G37A, G37C, G37D, G37E, G37F, G37H, G37I, G37K, G37L, G37M, G37N, G37P, G37Q, G37R, G37S, G37T, G37V, G37W, G37Y, L40A, L40C, L40D, L40E, L40F, L40G, L40H, L40I, L40K, L40M, L40N, L40P, L40Q, L40R, L40S, L40T, L40V, L40W, L40Y, N41A, N41C, N41D, N41E, N41F, N41G, N41H, N41I, N41K, N41L, N41M, N41P, N41Q, N41R, N41S, N41T, N41V, N41W, N41Y, E42A, E42C, E42D, E42F, E42G, E42H, E42I, E42K, E42L, E42M, E42N, E42P, E42Q, E42R, E42S, E42T, E42V, E42W, E42Y, V43A, V43C, V43D, V43E, V43F, V43G, V43H, V43I, V43K, V43L, V43M, V43N, V43P, V43Q, V43R, V43S, V43T, V43W, V43Y, P44A, P44C, P44D, P44E, P44F, P44G, P44H, P44I, P44K, P44L, P44M, P44N, P44Q, P44R, P44S, P44T, P44V, P44W, P44Y, I45A, I45C, I45D, I45E, I45F, I45G, I45H, I45K, I45L, I45M, I45N, I45P, I45Q, I45R, I45S, I45T, I45V, I45W, I45Y, E46A, E46C, E46D, E46F, E46G, E46H, E46I, E46K, E46L, E46M, E46N, E46P, E46Q, E46R, E46S, E46T, E46V, E46W, E46Y, K47A, K47C, K47D, K47E, K47F, K47G, K47H, K47I, K47L, K47M, K47N, K47P, K47Q, K47R, K47S, K47T, K47V, K47W, K47Y, P48A, P48C, P48D, P48E, P48F, P48G, P48H, P48I, P48K, P48L, P48M, P48N, P48Q, P48R, P48S, P48T, P48V, P48W, P48Y, Y54A, Y54C, Y54D, Y54E, Y54F, Y54G, Y54H, Y54I, Y54K, Y54L, Y54M, Y54N, Y54P, Y54Q, Y54R, Y54S, Y54T, Y54V, Y54W, S55A, S55C, S55D, S55E, S55F, S55G, S55H, S55I, S55K, S55L, S55M, S55N, S55P, S55Q, S55R, S55T, S55V, S55W, S55Y, G56A, G56C, G56D, G56E, G56F, G56H, G56I, G56K, G56L, G56M, G56N, G56P, G56Q, G56R, G56S, G56T, G56V, G56W, G56Y, T57A, T57C, T57D, T57E, T57F, T57G, T57H, T57I, T57K, T57L, T57M, T57N, T57P, T57Q, T57R, T57S, T57V, T57W, T57Y, L58A, L58C, L58D, L58E, L58F, L58G, L58H, L58I, L58K, L58M, L58N, L58P, L58Q, L58R, L58S, L58T, L58V, L58W, L58Y, N59A, N59C, N59D, N59E, N59F, N59G, N59H, N59I, N59K, N59L, N59M, N59P, N59Q, N59R, N59S, N59T, N59V, N59W, N59Y, F67A, F67C, F67D, F67E, F67G, F67H, F67I, F67K, F67L, F67M, F67N, F67P, F67Q, F67R, F67S, F67T, F67V, F67W, F67Y, S68A, S68C, S68D, S68E, S68F, S68G, S68H, S68I, S68K, S68L, S68M, S68N, S68P, S68Q, S68R, S68T, S68V, S68W, S68Y, G69A, G69C, G69D, G69E, G69F, G69H, G69I, G69K, G69L, G69M, G69N, G69P, G69Q, G69R, G69S, G69T, G69V, G69W, G69Y, F70A, F70C, F70D, F70E, F70G, F70H, F70I, F70K, F70L, F70M, F70N, F70P, F70Q, F70R, F70S, F70T, F70V, F70W, F70Y, E71A, E71C, E71D, E71F, E71G, E71H, E71I, E71K, E71L, E71M, E71N, E71P, E71Q, E71R, E71S, E71T, E71V, E71W, E71Y, S72A, S72C, S72D, S72E, S72F, S72G, S72H, S72I, S72K, S72L, S72M, S72N, S72P, S72Q, S72R, S72T, S72V, S72W, S72Y, E73A, E73C, E73D, E73F, E73G, E73H, E73I, E73K, E73L, E73M, E73N, E73P, E73Q, E73R, E73S, E73T, E73V, E73W, E73Y, K74A, K74C, K74D, K74E, K74F, K74G, K74H, K74I, K74L, K74M, K74N, K74P, K74Q, K74S, K74T, K74V, K74W, and/or K74Y or combinations thereof. It is contemplated that one or more of these substitutions may be specifically excluded in embodiments described herein.

In still further embodiments other amino acid substitutions can be introduced before, during, or after introduction of those amino acid substitutions listed above. Further substitutions (corresponding to SEQ ID NO:6) include, but is not limited to 2, 3, 4, 5, 6, 7, 8, 9, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, or 50 of P1A, P1C, P1D, P1E, P1F, P1G, P1H, P1I, P1K, P1L, P1M, P1N, P1Q, P1R, P1S, P1T, P1V, P1W, P1Y, S3A, S3C, S3D, S3E, S3F, S3G, S3H, S3I, S3K, S3L, S3M, S3N, S3P, S3Q, S3R, S3T, S3V, S3W, S3Y, P4A, P4C, P4D, P4E, P4F, P4G, P4H, P4I, P4K, P4L, P4M, P4N, P4Q, P4R, P4S, P4T, P4V, P4W, P4Y, S5A, S5C, S5D, S5E, S5F, S5G, S5H, S5I, S5K, S5L, S5M, S5N, S5P, S5Q, S5R, S5T, S5V, S5W, S5Y, G6A, G6C, G6D, G6E, G6F, G6H, G6I, G6K, G6L, G6M, G6N, G6P, G6Q, G6R, G6S, G6T, G6V, G6W, G6Y, V7A, V7C, V7D, V7E, V7F, V7G, V7H, V7I, V7K, V7L, V7M, V7N, V7P, V7Q, V7R, V7S, V7T, V7W, V7Y, T8A, T8C, T8D, T8E, T8F, T8G, T8H, T8I, T8K, T8L, T8M, T8N, T8P, T8Q, T8R, T8S, T8V, T8W, T8Y, L9A, L9C, L9D, L9E, L9F, L9G, L9H, L9I, L9K, L9M, L9N, L9P, L9Q, L9R, L9S, L9T, L9V, L9W, L9Y, M10A, M10C, M10D, M10E, M10F, M10G, M10H, M10I, M10K, M10L, M10N, M10P, M10Q, M10R, M10S, M10T, M10V, M10W, M10Y, L11A, L11C, L11D, L11E, L11F, L11G, L11H, UK L11K, L11M, L11N, L11P, L11Q, L11R, L11S, L11T, L11V, L11W, L11Y, N12A, N12C, N12D, N12E, N12F, N12G, N12H, N12I, N12K, N12L, N12M, N12P, N12Q, N12R, N12S, N12T, N12V, N12W, N12Y, Y15C, Y15D, Y15E, Y15F, Y15G, Y15H, Y15I, Y15K, Y15L, Y15M, Y15N, Y15P, Y15Q, Y15R, Y15S, Y15T, Y15V, Y15W, V16A, V16C, V16D, V16E, V16F, V16G, V16H, V16I, V16K, V16L, V16M, V16N, V16P, V16Q, V16R, V16S, V16T, V16W, V16Y, E17A, E17C, E17D, E17F, E17G, E17H, E17I, E17K, E17L, E17M, E17N, E17P, E17Q, E17R, E17S, E17T, E17V, E17W, E17Y, L18A, L18C, L18D, L18E, L18F, L18G, L18H, L18I, L18K, L18M, L18N, L18P, L18Q, L18R, L18S, L18T, L18V, L18W, L18Y, S19A, S19C, S19D, S19E, S19F, S19G, S19H, S19I, S19K, S19L, S19M, S19N, S19P, S19Q, S19R, S19T, S19V, S19W, S19Y, V28A, V28C, V28D, V28E, V28F, V28G, V28H, V28I, V28K, V28L, V28M, V28N, V28P, V28Q, V28R, V28S, V28T, V28W, V28Y, A29C, A29D, A29E, A29F, A29G, A29H, A29I, A29K, A29L, A29M, A29N, A29P, A29Q, A29R, A29S, A29T, A29V, A29W, A29Y, G30A, G30C, G30D, G30E, G30F, G30G, G30H, G30I, G30K, G30L, G30M, G30N, G30P, G30Q, G30R, G30S, G30T, G30V, G30W, G30Y, Y31A, Y31C, Y31D, Y31E, Y31F, Y31G, Y31H, Y31I, Y31K, Y31L, Y31M, Y31N, Y31P, Y31Q, Y31R, Y31S, Y31T, Y31V, Y31W, F32A, F32C, F32D, F32E, F32G, F32H, F32I, F32K, F32L, F32M, F32N, F32P, F32Q, F32R, F32S, F32T, F32V, F32W, F32Y, I33A, I33C, I33D, I33E, I33F, I33G, I33H, I33K, I33L, I33M, I33N, I33P, I33Q, I33R, I33S, I33T, I33V, I33W, I33Y, Y34A, Y34C, Y34D, Y34E, Y34F, Y34G, Y34H, Y34I, Y34K, Y34L, Y34M, Y34N, Y34P, Y34Q, Y34R, Y34S, Y34T, Y34V, Y34W, K35A, K35C, K35D, K35E, K35F, K35G, K35H, K35I, K35L, K35M, K35N, K35P, K35Q, K35R, K35S, K35T, K35V, K35W, K35Y, K38A, K38C, K38D, K38E, K38F, K38G, K38H, K38I, K38L, K38M, K38N, K38P, K38Q, K38R, K38S, K38T, K38V, K38W, K38Y, R39A, R39C, R39D, R39E, R39F, R39G, R39H, R39I, R39K, R39L, R39M, R39N, R39P, R39Q, R39S, R39T, R39V, R39W, R39Y, N49A, N49C, N49D, N49E, N49F, N49G, N49H, N49I, N49K, N49L, N49M, N49P, N49Q, N49R, N49S, N49T, N49V, N49W, N49Y, F50A, F50C, F50D, F50E, F50G, F50H, F50I, F50K, F50L, F50M, F50N, F50P, F50Q, F50R, F50S, F50T, F50V, F50W, F50Y, R51A, R51C, R51D, R51E, R51F, R51G, R51H, R51I, R51K, R51L, R51M, R51N, R51P, R51Q, R51S, R51T, R51V, R51W, R51Y, D52A, D52C, D52E, D52F, D52G, D52H, D52I, D52K, D52L, D52M, D52N, D52P, D52Q, D52R, D52S, D52T, D52V, D52W, D52Y, I53A, I53C, I53D, I53E, I53F, I53G, I53H, I53K, I53L, I53M, I53N, I53P, I53Q, I53R, I53S, I53T, I53V, I53W, I53Y, Y60A, Y60C, Y60D, Y60E, Y60F, Y60G, Y60H, Y60I, Y60K, Y60L, Y60M, Y60N, Y60P, Y60Q, Y60R, Y60S, Y60T, Y60V, Y60W, S61A, S61C, S61D, S61E, S61F, S61G, S61H, S61I, S61K, S61L, S61M, S61N, S61P, S61Q, S61R, S61T, S61V, S61W, S61Y, I62A, I62C, I62D, I62E, I62F, I62G, I62H, I62K, I62L, I62M, I62N, I62P, I62Q, I62R, I62S, I62T, I62V, I62W, I62Y, S63A, S63C, S63D, S63E, S63F, S63G, S63H, S63I, S63K, S63L, S63M, S63N, S63P, S63Q, S63R, S63T, S63V, S63W, S63Y, A64C, A64D, A64E, A64F, A64G, A64H, A64I, A64K, A64L, A64M, A64N, A64P, A64Q, A64R, A64S, A64T, A64V, A64W, A64Y, I65A, I65C, I65D, I65E, I65F, I65G, I65H, I65K, I65L, I65M, I65N, I65P, I65Q, I65R, I65S, I65T, I65V, I65W, I65Y, D66A, D66C, D66E, D66F, D66G, D66H, D66I, D66K, D66L, D66M, D66N, D66P, D66Q, D66R, D66S, D66T, D66V, D66W, D66Y, T75A, T75C, T75D, T75E, T75F, T75G, T75H, T75I, T75K, T75L, T75M, T75N, T75P, T75Q, T75R, T75S, T75V, T75W, T75Y, E76A, E76C, E76D, E76F, E76G, E76H, E76I, E76K, E76L, E76M, E76N, E76P, E76Q, E76R, E76S, E76T, E76V, E76W, E76Y, V77A, V77C, V77D, V77E, V77F, V77G, V77H, V77I, V77K, V77L, V77M, V77N, V77P, V77Q, V77R, V77S, V77T, V77W, V77Y, F78A, F78C, F78D, F78E, F78G, F78H, F78I, F78K, F78L, F78M, F78N, F78P, F78Q, F78R, F78S, F78T, F78V, F78W, F78Y, P79A, P79C, P79D, P79E, P79F, P79G, P79H, P79I, P79K, P79L, P79M, P79N, P79Q, P79R, P79S, P79T, P79V, P79W, P79Y, V80A, V80C, V80D, V80E, V80F, V80G, V80H, V80I, V80K, V80L, V80M, V80N, V80P, V80Q, V80R, V80S, V80T, V80W, V80Y, K81A, K81C, K81D, K81E, K81F, K81G, K81H, K81I, K81L, K81M, K81N, K81P, K81Q, K81R, K81S, K81T, K81V, K81W, K81Y, L82A, L82C, L82D, L82E, L82F, L82G, L82H, L82I, L82K, L82M, L82N, L82P, L82Q, L82R, L82S, L82T, L82V, L82W, L82Y, E83A, E83C, E83D, E83F, E83G, E83H, E83I, E83K, E83L, E83M, E83N, E83P, E83Q, E83R, E83S, E83T, E83V, E83W, E83Y, V84A, V84C, V84D, V84E, V84F, V84G, V84H, V84I, V84K, V84L, V84M, V84N, V84P, V84Q, V84R, V84S, V84T, V84W, V84Y, D85A, D85C, D85E, D85F, D85G, D85H, D85I, D85K, D85L, D85M, D85N, D85P, D85Q, D85R, D85S, D85T, D85V, D85W, D85Y, E86A, E86C, E86D, E86F, E86G, E86H, E86I, E86K, E86L, E86M, E86N, E86P, E86Q, E86R, E86S, E86T, E86V, E86W, E86Y, E87A, E87C, E87D, E87F, E87G, E87H, E87I, E87K, E87L, E87M, E87N, E87P, E87Q, E87R, E87S, E87T, E87V, E87W, E87Y, N88A, N88C, N88D, N88E, N88F, N88G, N88H, N88I, N88K, N88L, N88M, N88P, N88Q, N88R, N88S, N88T, N88V, N88W, N88Y, L89A, L89C, L89D, L89E, L89F, L89G, L89H, L89I, L89K, L89M, L89N, L89P, L89Q, L89R, L89S, L89T, L89V, L89W, L89Y, T90A, T90C, T90D, T90E, T90F, T90G, T90H, T90I, T90K, T90L, T90M, T90N, T90P, T90Q, T90R, T90S, T90V, T90W, T90Y, A91C, A91D, A91E, A91F, A91G, A91H, A91I, A91K, A91L, A91M, A91N, A91P, A91Q, A91R, A91S, A91T, A91V, A91W, A91Y, G92A, G92C, G92D, G92E, G92F, G92H, G92I, G92K, G92L, G92M, G92N, G92P, G92Q, G92R, G92S, G92T, G92V, G92W, G92Y, Y93A, Y93C, Y93D, Y93E, Y93F, Y93G, Y93H, Y93I, Y93K, Y93L, Y93M, Y93N, Y93P, Y93Q, Y93R, Y93S, Y93T, Y93V, Y93W, P94A, P94C, P94D, P94E, P94F, P94G, P94H, P94I, P94K, P94L, P94M, P94N, P94Q, P94R, P94S, P94T, P94V, P94W, P94Y, G95A, G95C, G95D, G95E, G95F, G95H, G95I, G95K, G95L, G95M, G95N, G95P, G95Q, G95R, G95S, G95T, G95V, G95W, G95Y, A96C, A96D, A96E, A96F, A96G, A96H, A96I, A96K, A96L, A96M, A96N, A96P, A96Q, A96R, A96S, A96T, A96V, A96W, A96Y, V97A, V97C, V97D, V97E, V97F, V97G, V97H, V97I, V97K, V97L, V97M, V97N, V97P, V97Q, V97R, V97S, V97T, V97W, V97Y, K98A, K98C, K98D, K98E, K98F, K98G, K98H, K98I, K98L, K98M, K98N, K98P, K98Q, K98R, K98S, K98T, K98V, K98W, K98Y, V99A, V99C, V99D, V99E, V99F, V99G, V99H, V99I, V99K, V99L, V99M, V99N, V99P, V99Q, V99R, V99S, V99T, V99W, V99Y, K100A, K100C, K100D, K100E, K100F, K100G, K100H, K100I, K100L, K100M, K100N, K100P, K100Q, K100R, K100S, K100T, K100V, K100W, K100Y, V101A, V101C, V101D, V101E, V101F, V101G, V101H, V101I, V101K, V101L, V101M, V101N, V101P, V101Q, V101R, V101S, V101T, V101W, V101Y, E102A, E102C, E102D, E102F, E102G, E102H, E102I, E102K, E102L, E102M, E102N, E102P, E102Q, E102R, E102S, E102T, E102V, E102W, E102Y, N103A, N103C, N103D, N103E, N103F, N103G, N103H, N103I, N103K, N103L, N103M, N103P, N103Q, N103R, N103S, N103T, N103V, N103W, N103Y, L104A, L104C, L104D, L104E, L104F, L104G, L104H, L104I, L104K, L104M, L104N, L104P, L104Q, L104R, L104S, L104T, L104V, L104W, L104Y, D105A, D105C, D105E, D105F, D105G, D105H, D105I, D105K, D105L, D105M, D105N, D105P, D105Q, D105R, D105S, D105T, D105V, D105W, D105Y, G106A, G106C, G106D, G106E, G106F, G106H, G106I, G106K, G106L, G106M, G106N, G106P, G106Q, G106R, G106S, G106T, G106V, G106W, G106Y, E107A, E107C, E107D, E107F, E107G, E107H, E107I, E107K, E107L, E107M, E107N, E107P, E107Q, E107R, E107S, E107T, E107V, E107W, E107Y, A108C, A108D, A108E, A108F, A108G, A108H, A108I, A108K, A108L, A108M, A108N, A108P, A108Q, A108R, A108S, A108T, A108V, A108W, and/or A108Y and combinations thereof. It is contemplated that one or more of these substitutions may be specifically excluded in embodiments described herein.

In certain aspects, the library comprises a variation in an amino acid corresponding to amino acid 1 of SEQ ID NO:1 in combination with one or more residue corresponding to amino acid 2, 3, 4, 14, 28, and 58.

In a further aspect, the library comprises a variation in an amino acid corresponding to amino acid 2 of SEQ ID NO:1 in combination with one or more residue corresponding to amino acid 1, 3, 4, 14, 28, and/or 58.

In a still a further aspect, the library comprises a variation in an amino acid corresponding to amino acid 3 of SEQ ID NO:1 in combination with one or more residue corresponding to amino acid 1, 2, 4, 14, 28, and/or 58.

In a further aspect, the library comprises a variation in an amino acid corresponding to amino acid 4 of SEQ ID NO:1 in combination with one or more residue corresponding to amino acid 1, 2, 3, 14, 28, and/or 58.

In a certain aspect, the library comprises a variation in an amino acid corresponding to amino acid 14 of SEQ ID NO:1 in combination with one or more residue corresponding to amino acid 1, 2, 3, 4, 28, and/or 58.

In a further aspect, the library comprises a variation in an amino acid corresponding to amino acid 28 of SEQ ID NO:1 in combination with one or more residue corresponding to amino acid 1, 2, 3, 4, 14, and/or 58.

In a further aspect, the library comprises a variation in an amino acid corresponding to amino acid 58 of SEQ ID NO:1 in combination with one or more residue corresponding to amino acid 1, 2, 3, 4, 14, and/or 28.

D. Library Screening

Library screening can be conducted in order to select FN3 variants that bind to specific ligands or targets. Combinatorial screening can easily produce and screen a large number of variants, which is not feasible with specific mutagenesis ("rational design") approaches. Amino acid variant at various amino acid positions in FN3 can be generated using a degenerate nucleotide sequence. FN3 variants with desired binding capabilities can be selected in vitro, recovered and amplified. The amino acid sequence of a selected clone can be identified readily by sequencing the nucleic acid encoding the selected FN3.

In some embodiments, a particular FN3-based molecule has an affinity for a target that is at least 2-fold greater than the affinity of the polypeptide prior to substitutions discussed herein. In some embodiments, the affinity is, is at least, or is at most about 2-, 3-, 4-, 5-, 6-, 7-, 8-, 9-, 10-, 15-, 20-, 25-, 30-, 35-, 40-, 45-, 50-, 60-, 70-, 80-, 90-, 100-fold increased (or any range derivable therein) compared to another FN3-based molecule.

Phage Display Library and Selection. A FN3 polypeptide library can be created using a "shaved" template containing polyserine sequence at locations to be diversified (Koide et al., 2007 and Wojcik et al., 2010). A synthetic DNA fragment that encodes signal sequence of DsbA (Steiner et al., 2006) can be fused to the gene for the template, and the fusion gene can be cloned into a phage display vector (Koide et al., 1998). A phage-display combinatorial library can be constructed by introducing codons for amino acid variation into the FN3 polypeptide. Library construction procedures have previously been described (Koide and Koide, 2007).

Phagemid particles can be prepared by growing XL1-Blue cells transfected with the phagemid library in the presence of IPTG and helper phage (Lo Conte et al., 1999; Fellouse et al., 2005). Phagemid library selection can be performed as follows. In the first round, 0.5 □M of a target protein modified with EZ-Link Sulfo-NHS-SS-Biotin (Sulfosuccinimidyl 2(biotinamido)-ethyl-1,3-dithiopropionate; Pierce) can be mixed with a sufficient amount of streptavidin-conjugated magnetic beads (Streptavidin MagneSphere Paramagnetic Particles; Promega, Z5481/2) in TBS (50 mM Tris HCl buffer pH 7.5 150 mM NaCl) containing 0.5% Tween20 (TBST). To this target solution, 1012-13 phagemids suspended in 1 ml TBST plus 0.5% BSA can be added, and the solution can then be mixed and incubated for 15 min at room temperature. After washing the beads twice with TBST, the beads suspension containing bound phagemids can be added to fresh *E. coli* culture. Phagemids were amplified as described before (Fellouse et al., 2005). In a second round, phagemids can be incubated with 0.1 □M target in TBST plus 0.5% BSA, and then captured by streptavidin-conjugated magnetic beads.

Phagemids bound to the target protein can be eluted from the beads by cleaving the linker within the biotinylation reagent with 100 mM DTT in TBST. The phagemids can then be washed and recovered as described above. After amplification, the third round of selection may be performed using 0.02 □M target. Phage display is an established technique for generating binding members and has been described in detail in many publications such as Kontermann & Dubel (2001) and WO92/01047, each of which is incorporated herein by reference in its entirety.

Yeast Surface Display. Yeast surface experiments can be performed according to Boder and Wittrup (2000) with minor modifications. The Express-tag in the yeast display vector, pYD1, (Invitrogen) may be removed, since it can cross-react with anti-FLAG antibodies (Sigma). The genes for monobodies in the phagemid library after three rounds of selection can be amplified using PCR and mixed with the modified pYD1 cut with EcoRI and XhoI, and yeast EBY100 cells can transformed with this mixture. The transformed yeast cells can grown in the SD-CAA media at 30□C for two days, and then monobody expression can be induced by growing the cells in the SG-CAA media at 30□C for 24 h.

Sorting of monobody-displaying yeast cells may be performed as follows. The yeast cells may be incubated with a biotinylated target (50 nM) and mouse anti-V5 antibody (Sigma), then after washing incubated with anti-mouse antibody-FITC conjugate (Sigma) and neutravidin-PE conjugate (Invitrogen). The stained cells can be sorted based on the FITC and PE intensities. Typically, cells exhibiting the top □1% PE intensity and top 10% FITC intensity are recovered.

After FACS sorting, individual clones can be analyzed. Approximate Kd values can be determined from a titration curve by FACS analysis (Boder and Wittrup, 2000). Amino acid sequences can be deduced from DNA sequencing.

Effects of *E. coli* lysate on monobody-target interaction can be tested by comparing binding in the presence and absence of *E. coli* lysate prepared from cell suspension with OD600 of 50.

Protein Expression and Purification. The nucleic acid encoding any targets can be cloned in the appropriate expression vector. In one example, genes for monobodies can be cloned in the expression vector, pHFT2, which is a derivative of pHFT1 (Huang et al., 2006) in which the His-6 tag had been replaced with a His-10 tag. Protein expression and purification can be performed as described previously (Huang et al., 2006).

An expression vector comprising cDNA encoding a FN3 polypeptide or a target molecule is introduced into *Escherichia coli*, yeast, an insect cell, an animal cell or the like for expression to obtain the polypeptide. Polypeptides used in the methods and compositions of the disclosure can be produced, for example, by expressing a DNA encoding it in a host cell using a method described in Molecular Cloning, A Laboratory Manual, Second Edition, Cold Spring Harbor Laboratory Press (1989), Current Protocols in Molecular Biology, John Wiley & Sons (1987-1997) or the like. A recombinant vector is produced by inserting a cDNA downstream of a promoter in an appropriate expression vector. The vector is then introduced into a host cell suitable for the expression vector. The host cell can be any cell so long as it can express the gene of interest, and includes bacteria (e.g., *Escherichia coli*), an animal cell and the like. Expression vector can replicate autonomously in the host cell to be used or vectors which can be integrated into a chromosome comprising an appropriate promoter at such a position that the DNA encoding the polypeptide can be transcribed.

V. Affinity Claims

Embodiments of the disclosure, particularly those comprising a polypeptide comprising a biorecognition module including a molecular recognition domain relate to a polypeptide capable of forming an "affinity clamp" to a target motif.

It is informative to compare characteristics of molecular affinity clamps with those of antibodies, the gold standard of affinity reagents. Antibodies are general and versatile affinity reagents. The immune system can produce an antibody to virtually any molecule. The diversity of the immunoglobulin repertoire is 1010-12, which is similar in size to the diversity of a typical phage display library (1010). This versatility of the antibodies, however, also means that the antibody repertoire is not focused and that only a small subset of the naive repertoire is available to bind to a particular class of antigen. For example, antibodies that bind to lysozyme and those that bind to a phospho-Ser peptide are distinct subsets of the same repertoire.

Economical and scalable production is another important area of consideration for affinity reagents. As noted above, polyclonal antibodies cannot be reproduced, once the original stock is depleted. Monoclonal antibodies can be reproduced, but the maintenance and large-scale culture of hybridoma cells are cumbersome and expensive. Antibodies can also be produced by recombinant technologies, but the natural diversity throughout the antibody molecules (i.e., framework diversity in addition to the extensive diversity within the antigen binding loops) makes formatting them for different applications fundamentally low throughput. Moreover, because of the presence of critical disulfide bonds, recombinant production of antibodies is not straightforward. For this reason, a number of alternative "molecular scaffolds" for engineering affinity reagents have been developed that are small and devoid of disulfide bonds (8-10). Although these new-generation affinity reagents generally have good affinity and specificity, developing affinity reagents for short peptide motifs remains a major challenge in the field, because of the fundamental difficulties stated hereinabove.

In contrast, molecular affinity clamps in accordance with the disclosure are affinity reagents directed to a pre-defined motif. In one aspect, molecular affinity clamps are built with a particular biorecognition module comprising an interaction domain that is specific primarily to the class of target motifs that the interaction domain recognizes. Because of this pre-defined binding specificity, repertoire diversity can then be used to enhance the properties of affinity reagents rather than to blindly search for initial hits. This distinctive feature of the invention may lead to an increased success rate of producing high-affinity reagents for a motif of interest. In another embodiment, the molecular affinity clamps are build with one or more variant FN3 domains.

The two polypeptide molecules of the affinity clamp (e.g. the first polypeptide comprising the variant FN3 domain and the second polypeptide comprising the biorecognition module, which can include an interaction domain or a second variant FN3 domain) are spatially oriented to bind distinct, overlapping, or the same sites within target motif of a target. The configuration of the two biorecognition modules about the target motif is clamp-like or clamshell-like, i.e., the target motif is "clamped" between the two biorecognition modules. The two biorecognition modules of the affinity clamp are capable of together binding a single target motif on a single target. The first polypeptide molecule and second polypeptide molecules may bind at least overlapping portions the target motif on a target. This is unlike other binding molecules, such as an antibody, where the binding molecules recognize non-overlapping target motifs, different target motifs, or the same target motif located on more than one target. In another aspect, the affinity clamp is suitably described as a ternary complex composition of the type:

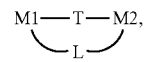

wherein M1 and M2 are independently the polypeptide comprising the variant FN3 domain and the polypeptide comprising the biorecognition module, L is a direct bond or linker moiety used for tethering the first and second biorecognition modules, and T is a target motif. M1 includes a variant FN3 domain bound to a first site of the target motif, and M2 includes a molecular recognition domain bound to a second site of the target motif (or vice versa) without disrupting the binding of the variant FN3 domain. The first and second sites can be the same, overlapping, or distinct sites within the target motif. L as a linker is selected from the group consisting of a peptide which is equal to or shorter than 30 residues, a group capable of disulfide bonding, and a chemical crosslinker.

B. Target Motif

A target motif suitable in accordance with the disclosure may be any motif which can be recognized by a biorecognition module, e.g., an interaction domain. Such target motifs include peptides and covalently modified peptides, including but not limited to peptides that are phosphorylated, methylated, acetylated, ubiquinated, SUMOylated, ISGylated, glycosylated, acylated, prenylated, ribosylated, gammacarboxylated, or sulfated.

C. Biorecognition Module

Among the commonly occurring domains identified in signaling proteins are the so-called "interaction domains." Interaction domains are typically small (usually less than ~100 amino acids) and autonomously folded. Many of them bind to short peptide motifs that often contain modified amino acids. It has been found that a primary binding domain, i.e., the molecular recognition domain, of the biorecognition module is suitably an interaction domain. With molecular affinity clamp technology, the interaction domains as the biorecognition modules can be engineered in such a way that the enhancer domain can be connected in a proper orientation. The bifunctional module architecture of the molecular affinity clamps in accordance with the invention, after optimization, significantly increases the surface areas of the peptide-binding interface by forming the clamshell architecture, leading to higher affinity and/or specificity. Use of interaction domains as the primary binding domain is based on the following common features of these domains: a target peptide motif binds to a shallow groove on the interaction domain surface, and the peptide is still highly exposed; there are turns and/or loops located close to the peptide-binding site; and the N- and C-termini are juxtaposed in space so that they could be connected and a new set of termini could be created elsewhere.

In short, molecular affinity clamp technology makes it possible to define the primary specificity of affinity reagents in advance (e.g., using the specificity of the interaction domain), and then, enhance that affinity and/or specificity. This modular architecture in accordance with the disclosure transforms affinity reagent development from an "unguided fishing expedition" to a focused, rational and robust process.

Interaction domains, suitable as the recognition domain, include, but are not limited to, domains involved in phoshotyrosine binding (e.g. SH2, PTB), phospho-serine binding (e.g. UIM, GAT, CUE, BTB/POZ, VHS, UBA, RING, HECT, WW, 14-3-3, Polo-box), phospho-threonine binding (e.g. FHA, WW, Polo-box), proline-rich region binding (e.g. EVH1, SH3, GYF), acetylated lysine binding (e.g. Bromo), methylated lysine binding (e.g. Chromo, PHD), apoptosis (e.g. BIR, TRAF, DED, Death, CARD, BH), cytoskeleton modulation (e.g. ADF, GEL, DH, CH, FH2), or other cellular functions (e.g. EH, CC, VHL, TUDOR, PUF Repeat, PAS, MH1, LRR, IQ, HEAT, GRIP, TUBBY, SNARE, TPR, TIR, START, SOCS Box, SAM, RGS, PDZ, PB1, LIM, F-BOX, ENTH, EF-Hand, SHADOW, ARM, ANK).

D. Linkers

The variant FN3 polypeptide and polypeptide comprising the biorecognition module may be linked together either directly, e.g., bound together with a peptide sequence via a tail from one of the modules, or indirectly via a linker. As to the latter, the linker generally is bifunctional in that it includes a functionality for linking the biorecognition module and a functionality for linking variant FN3 polypeptide. The linker may suitably be a specific moiety, such as an amino acid sequence of about 30 or fewer residues. It is also contemplated that the two polypeptide domains may be linked non-covalently through a high affinity binding interaction or physical association such as the interaction mediated by coiled-coil peptides.

E. Detection of Affinity Clamp Binding

In general, the different conformational states of modular affinity clamps used in accordance with the disclosure will correspond to different separation distances between the polypeptide modules, whereby changes in conformation may be conveniently monitored by means of a separation sensitive signal.

Various forms of separation sensitive signal systems may be used with the affinity clamps of the disclosure. In such embodiments, the biorecognition module includes a first signaling moiety and the variant FN3 polypeptide includes a second signaling moiety, and the first and second signaling moieties are capable of interacting to produce a detectable signal. The signaling moieties may include dyes, quenchers, reporter proteins and quantum dots. Particularly useful are embodiments in which the polypeptide domains include optical signaling pairs that can produce a detectable signal when the proximity of the modules with respect to each other changes with the binding of the polypeptide domains. Suitably, the first and second signaling modules are a fluorescence resonance energy (FRET) donor group and a receptor group, respectively. The change in proximity of the FRET groups produces an optical signal which differs between when the target motif is present and not present.

It will also be appreciated that various other means may be used for "reading" the presence of target motif binding to a modular affinity clamp, and/or the resultant change in conformational state of the affinity clamp structure. Many different labeling systems may be used, such as fluorophore labeling (including quantum dot), radio-labeling, and redox labeling.

F. Use of Affinity Clamps as Biosensors

Molecular affinity clamps in accordance with the disclosure may be suitably used as a biosensor wherein the polypeptide modules are each labeled with paired signaling moieties as described above.

A plurality of affinity clamps described herein may be immobilized, directly or indirectly to a support or substrate to form an array of clamps or an array of biosensors. Supports or substrates can take a variety of forms such as polymers, glasses, metal and those with coating therein. Arrays are ordered arrangements of elements, allowing them to be displayed and examined in parallel. Arrays of immobilized affinity clamps can be used to detect the target motif and demonstrate the binding reaction. Certain array formats are sometimes referred to as "biochips." Biochips may include a plurality of locations configured so that each location is spatially addressable. Typically, the clamp format is configured in a row and column format with regular spacing between locations, wherein each location has machine-readable (e.g., computer-readable) information to identify the location on the surface of the substrate.

The affinity clamp technology provides a method of detecting the presence and amount of a target motif in a sample by using the affinity clamp as a biosensor. Specifically, a sample is contacted under specific conditions with a biosensor. Fluorescence events are sensed with the binding of the polypeptide modules to the target motif in the sample and in the absence of the sample, and the fluorescence sensing in the absence of the target motif is correlated with a change in the FRET signal in the presence of the target motif. Thus, absence of the target motif generates a specific FRET signal in terms of the wavelength and amplitude of the emission, and the presence of the target motif generates a modulated FRET signal emission in terms of either the wavelength or amplitude or both. Samples may include blood, saliva or tissue.

Accordingly, an affinity clamp array as a biosensor array includes a plurality of affinity clamps or biosensors anchored to the surface of a substrate, each at an addressable site on the substrate.

G. Construction of a Modular Molecular Affinity Clamp

The general engineering of a molecular affinity clamp is given basically in four steps. Step 1 involves identifying the potential locations for attachment, via a linker, of the variant FN3 polypeptide to the biorecognition module by visual inspection of the interaction domain structure and/or from sequence variability among interaction domain family members, and testing the tolerance of identified locations for extensive modifications, for example, by inserting four Gly residues.

Step 2 includes two sub-steps, Step 2a and 2b. Step 2a is included if circular permutations are performed to construct new termini closer to the interaction domain binding site. In some embodiments, Step 2a is not needed. In Step 2a, if circular permutation is performed, a domain is constructed by joining the original termini and cutting the polypeptide at a location closer to the target-binding site of the interaction domain that tolerates mutations. Then, in Step 2b, the variant FN3 polypeptide is attached to the C-terminus of the circularly permutated domain or the natural C-terminus (in the case where no circular permutation is performed.) The N-terminus of FN3 is located close to its functional loops, and thus, connecting the FN3 N-terminus to the interaction domain ensures that the FN3 binding loops are facing the target motif-binding site.

In Step 3, amino acid diversity is introduced in FN3 loops to construct a large combinatorial library of mutated polypeptides, and in Step 4, library sorting is performed to optimize the enhancer domain for a specific target motif.

Further embodiments of the affinity clamp are described in WO/2009/062170, which is herein incorporated by reference.

VI. Polypeptide Compositions

The polypeptides or polynucleotides of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more variant amino acids or nucleic acid substitutions or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with at least, or at most 3, 4, 5, 6, 7, 8, 9, 10, 11, 12, 13, 14, 16, 17, 18, 19, 20, 21, 22, 23, 24, 25, 26, 27, 28, 29, 30, 31, 32, 33, 34, 35, 36, 37, 38, 39, 41, 42, 43, 44, 45, 46, 47, 48, 49, 50, 51, 52, 53, 54, 55, 56, 57, 58, 59, 60, 61, 62, 63, 64, 66, 67, 68, 69, 70, 71, 72, 73, 74, 75, 76, 77, 78, 79, 80, 81, 82, 83, 84, 85, 86, 87, 88, 89, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids or nucleic acids, or any range derivable therein, of SEQ ID NOs:1-7.

The polypeptides or polynucleotides of the disclosure may include 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 36, 37, 38, 39, 40, 41, 42, 43, 44, 45, 46, 47, 48, 49, 50, 51, 52, 53, 54, 55, 56, 57, 58, 59, 61, 62, 63, 64, 65, 66, 67, 68, 69, 70, 71, 72, 73, 74, 75, 76, 77, 78, 79, 80, 81, 82, 83, 84, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more contiguous amino acids, or any range derivable therein, of SEQ ID NO:1-7.

In some aspects there is a nucleic acid molecule or polypeptide starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of any of SEQ ID NOS:1-7 and comprising 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 contiguous nucleotides or polypeptides of any of SEQ ID NOS:1-7.

The polypeptides and nucleic acids of the disclosure may include at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 substitutions.

The substitution may be at amino acid position or nucleic acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 of one of SEQ ID NO:1-7.

Embodiments include polypeptides and polynucleotides with at least, at most, or exactly 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) identity, similarity, or homology to one of SEQ ID NO:1-7.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

The current disclosure concerns methods and compositions related to the identification and use of variants of FN3 and libraries containing the same. As used herein, a "polypeptide" generally is defined herein to refer to a peptide sequence of about 10 to about 1,000 or more amino acid residues.

The polypeptides included in the methods set forth herein are variants in that they comprise a FN3 amino acid sequence that has been altered by substitution, insertion and/or deletion of one or more amino acid. The polypeptides set forth herein may demonstrate a selective and/or specific binding affinity for particular target molecules or portions thereof.

In certain embodiments, the polypeptide is a fusion polypeptide that includes a variant FN3 amino acid sequence linked at the N- or C-terminus to a second peptide or polypeptide. In other embodiments, the polypeptide comprises a linker interposed between the FN3 amino acid sequence and the second peptide or polypeptide sequence. Linkers are discussed in greater detail in the specification below.

Furthermore, the polypeptides set forth herein may comprise a sequence of any number of additional amino acid residues at either the N-terminus or C-terminus of the amino acid sequence that includes the variant FN3 amino acid sequence. For example, there may be an amino acid sequence of about 3 to about 1,000 or more amino acid residues at either the N-terminus, the C-terminus, or both the N-terminus and C-terminus of the amino acid sequence that includes the variant FN3 amino acid sequence.

The polypeptide may include the addition of an antibody epitope or other tag, to facilitate identification, targeting, and/or purification of the polypeptide. The use of 6×His and GST (glutathione S transferase) as tags is well known. Inclusion of a cleavage site at or near the fusion junction will facilitate removal of the extraneous polypeptide after purification. Other amino acid sequences that may be included in the polypeptide include functional domains, such as active sites from enzymes such as a hydrolase, glycosylation domains, cellular targeting signals or transmembrane regions. The polypeptide may further include one or more additional tissue-targeting moieties.

Polypeptides may possess deletions and/or substitutions of amino acids relative to the native sequence. Sequences with amino acid substitutions are contemplated, as are sequences with a deletion, and sequences with a deletion and a substitution. In some embodiments, these polypeptides may further include insertions or added amino acids. Substitutional or replacement variants typically contain the exchange of one amino acid for another at one or more sites within the protein and may be designed to modulate one or more properties of the polypeptide, particularly to increase its efficacy or specificity. Substitutions of this kind may or may not be conservative substitutions. Conservative substitution is when one amino acid is replaced with one of similar shape and charge. Being that the libraries of variant FN3 domains serves to provide a diversity of amino acid sequences and binding selectivity conservative substitutions are not required. However, if used, conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Changes other than those discussed above are generally considered not to be conservative substitutions. It is specifically contemplated that one or more of the conservative substitutions above may be included as embodiments. In other embodiments, such substitutions are specifically excluded. Furthermore, in additional embodiments, substitutions that are not conservative are employed in variants.

In addition to a deletion or substitution, the polypeptides may possess an insertion of one or more residues.

The variant FN3 amino acid sequence may be structurally equivalent to the native counterparts. For example, the variant FN3 amino acid sequence forms the appropriate structure and conformation for binding targets, proteins, or peptide segments.

The following is a discussion based upon changing of the amino acids of a polypeptide to create a library of molecules or a second-generation molecule. For example, certain amino acids may be substituted for other amino acids in a polypeptide without appreciable loss of function, such as ability to interact with a target peptide sequence. Since it is the interactive capacity and nature of a polypeptide that defines that polypeptide's functional activity, certain amino acid substitutions can be made in a polypeptide sequence and nevertheless produce a polypeptide with like properties.

In making such changes, the hydropathic index of amino acids may be considered. The importance of the hydropathic amino acid index in conferring interactive function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. However, in some aspects a non-conservative substitution is contemplated. In certain aspects a random substitution is also contemplated. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

VII. Polynucleotides

Aspects of the disclosure relate to polypeptides and polynucleotides encoding such polypeptides. The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of the disclosure that is a polynucleotide encompasses both the double-stranded form and each of two complementary single-stranded forms known or predicted to make up the double-stranded form.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'. It will be recognized by one of skill in the art that two complementary nucleotide sequences include a sense strand and an antisense strand.

Polypeptides may be encoded by a nucleic acid molecule in the composition. In certain embodiments, the nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody.

The term "expression vector" refers to a vector containing a nucleic acid sequence coding for at least part of a gene product capable of being transcribed or stably integrate into a host cell's genome and subsequently be transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein. It is contemplated that expression vectors that express a marker may be useful in the methods and compositions of the disclosure. In other embodiments, the marker is encoded on an mRNA and not in an expression vector.

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

The particular promoter that is employed to control the expression of a peptide or protein encoding polynucleotide is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter. In some embodiments, the host cell is an eukaryotic cell. In some embodiments, using eukaryotic cells is beneficial, as it provides for secondary modifications that may not be present in certain prokaryotic systems.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The polynucleotides and polypeptides of the disclosure may be transfected of transformed into host cells or expressed in host cells. As used herein, the terms "cell," "cell line," and "cell culture" may be used interchangeably. All of these terms also include both freshly isolated cells and ex vivo cultured, activated or expanded cells. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny. Common host cells include bacteria (such as *E. coli, B. subtilis, S. viofoceoruber*), yeast (such as *S. cerevisiae, P. pastoris*), fungi (such as *A. oryzae*) or eukaryotic cells.

VIII. Kits

Kits are also contemplated as being made or used in certain aspects of the present disclosure. For instance, a polypeptide or nucleic acid of the disclosure can be included in a kit or in a library provided in a kit. A kit can be included in a sealed container. Non-limiting examples of containers include a microtiter plate, a bottle, a metal tube, a laminate tube, a plastic tube, a dispenser, a pressurized container, a barrier container, a package, a compartment, or other types of containers such as injection or blow-molded plastic containers into which the dispersions or compositions or desired bottles, dispensers, or packages are retained. Other examples of containers include glass or plastic vials or bottles. The kit and/or container can include indicia on its surface. The indicia, for example, can be a word, a phrase, an abbreviation, a picture, or a symbol.

The containers can dispense or contain a pre-determined amount of a composition of the present disclosure. The composition can be dispensed as a liquid, a fluid, or a semi-solid. A kit can also include instructions for using the kit and/or compositions. Instructions can include an explanation of how to use and maintain the compositions.

EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of particular embodiments, are exemplary, and are not intended as limitations on the scope of the invention. Changes therein and other uses which are encompassed within the spirit of the invention as defined by the scope of the claims will occur to those skilled in the art.

Example 1: Thermonobodies, Synthetic Binding Proteins Based on a Hyperthermophilic Fibronectin Type III Domain A. Identification of FN3 Domain from Hyperthermophiles The inventors utilized the SMART database to explore FN3 domains from hyperthermophiles. The database predicted many FN3 domains in hyperthermophilic archaea and bacteria such as *Thermococcus kodakaraensis, Sulfolobus tokodaii, Pyrococcus horikoshii* and *Thermotoga lettingae*. The inventors first eliminated predicted domains that were shorter than the length of the shortest FN3 domains that had been structurally characterized (75 amino acids). Then, four FN3 domains in the sequence of Kelch domain-containing protein ST0939 from the hyperthermophilic archaeon *Sulfolobus tokodaii* DSM 16993 were chosen as the candidate proteins, because of their detectably homology to a human FN3. In the predicted constructs, termed STOFN3-1, -2, -3 and -4, consist of 84 (positions 315-398), 86 (399-484), 79 (488-566) and 76 (568-643) amino acids, respectively, and each construct maintain at least two of the three highly conserved hydrophobic amino acids of FN3 domains (FIG. 1A).

Expression vectors for these constructs were constructed using synthetic genes. It was found that only the N-terminal two domains (STOFN3-1 and -2) were robustly produced in *E. coli* as soluble proteins that were predominantly monomeric (FIG. 1B). We detected little protein for the third domain, and the fourth domain was expressed mostly as insoluble proteins. These results demonstrate the challenge of predicting constructs that behave well as purified proteins, even for members of the well characterized FN3 domain. Melting temperatures obtained by differential scanning fluorimetry (DSF) were 80° C. for STOFN3-1 and 70° C. for STOFN3-2, respectively, confirming that they were indeed thermostable proteins (FIG. 1C).

To confirm that STOFN3-1 and STOFN3-2 had the FN3 fold, we determined their crystal structures at 1.28 and 2.45 Å resolutions, respectively. Both segments indeed adopt the FN3 fold consisting of seven anti-parallel β-strands and six loops (FIG. 2A, 2B). Superposition with the FN3fn10 (PDB ID: 1FNA), the well characterized FN3 scaffold, demonstrated that the structures of the segments are highly similar to FN3fn10 with an average RMSD value of 1.9 Å for STOFN3-1 and 1.8 Å for STOFN3-2, respectively, for aligned backbone Cα atoms (excluding loops) (FIG. 2C). STOFN3-1 was then chosen for further experiments, because of its superior biophysical properties to STOFN3-2 in terms of expression level, thermal stability, solubility and the ease to obtain high-resolution structure.

In the crystal structure, three continuous Pro residues (P315, P316 and P317) in the N-terminal region of STOFN3-1 were highly ordered and positioned between the BC and FG loops, the loops commonly utilized for presenting diversified residues (FIG. 3A). Because this N-terminal segment may interfere with creating a target binding site by presenting BC and/or FG loops, the Pro residues were substituted with Ser residues to reduce hydrophobicity and increase flexibility. The high-resolution crystal structure showed that the segment N-terminal to P317S of the mutant had low electron density indicative of conformational disorder (FIG. 3B), strongly suggesting that this segment was dislodged from the folded portion within the construct. The apparent dissociation of this fragment only slightly decreased the stability FIG. 3D).

The crystal structure of STOFN3-1 also revealed that, surprisingly, the last residues of the FN3 domain according to the SMART database prediction (T398) was located in the middle of the last β-strand (G strand). The β-strand continued by incorporating a Ser residue we added as an artificial extension to the predicted C-terminus (FIG. 3C), suggesting that the predicted boundaries did not accurately match the structural boundary of the domain. We thus extended the C-terminus by adding four residues (P399, 5400, 5401 and an extra Serine residue) of ST0939, of which P399-S401 were predicted to be N-terminal residues of STOFN3-2 by the SMART database. The crystal structure of this extended construct confirmed that the added segment was properly incorporated into the β-sheet (FIG. 3C), and the construct was more thermostable than the original one (FIG. 3D).

The stability of STOFN3-1 was further improved by structure-guided design. Based on a structure-guided alignment with FN3 domains, it was found that STOFN3-1 lacked highly conserved Proline residues in FN3 domains. Replacing these residues with Pro (N328P in the AB loop and D372P in the EF loop) improved the thermostability (FIG. 3D). The variant containing all the improvements, namely, the N-terminal substitution, C-terminal extension and Pro mutations now exhibited very high thermal stability with the melting temperature exceeding 95° C. (FIG. 3D). This construct was used as the template for constructing combinatorial libraries (termed STOTEMP2).

B. Identification of Positions Permissive to Amino Acid Diversification

In parallel to the scaffold improvements described above, the inventors identified positions of STOFN3-1 that are tolerant to amino acid diversification so that library designs avoid mutating positions critical for maintaining thermal stability and high solubility. A series of point mutations and insertions were introduced to the STOFN3-1 construct and their thermal stabilities were measured (FIG. 4A-C).

On the bottom end of the molecule as depicted in FIG. 2A, the poly-Ser mutations of the AB and CD loops resulted in little destabilization. In contrast, whereas that of EF loop destabilized STOFN3-1 by 16° C. The sensitivity of the EF loop to mutations is consistent with previous reports for other FN3 domains, which can be rationalized by the presence of the structurally important "Tyrosine corner" motif in the EF loop of STOFN3-1. On the top end of the molecule, the mutation of the BC loop slightly destabilized STOFN3-1 and that of the DE loop showed no destabilizing effect. The serine mutation of G360 immediately N-terminal to the DE loop resulted in inclusion body formation in *E. coli* and also dramatically decreased the stability (Tm reduction by more than 15° C.). Four sets of poly-Serine mutations of the FG loop all showed karge destabilization effect (13-20° C.), and all but FGser1 were expressed predominantly as inclusion bodies. This result suggested that both Y383 and P391, residues not mutated in the FGser1 mutant, were critical for efficient folding of STOFN3-1.

In addition to substation mutations, insertions of 2, 4 and 8 Serine residues into the BC, CD, DE and FG loops, the loops that tolerated substitution mutations were tested (FIG. 4C). Of these loops, the BC loop highly tolerated the insertions, whereas insertions in the CD and FG loops were destabilizing but these mutants still maintained the Tm of around 70° C. A very large destabilizing effect was observed for the DE-loop elongation. Even an insertion of two residues decreased the stability by 25° C. None of these insertion mutants resulted in substantial inclusion body formation. Taken together, these systematic mutation experiments identified that DE, EF and FG loops are less permissive to mutations than the other loops, but the most destabilized mutants still had Tm higher than 50° C.

In the crystal structure, the side chain of Y383, the structurally important Tyr in the F strand, interacts with G342 in the C strand, apparently providing the "Aromatic rescue" of the destabilizing Gly residue in a 0-strand (Regan ref). The impact of Y383 mutation completely disappeared when we substituted G342 with Tyr, an equivalent residue in FN3fn10 (FIG. 3D and FIG. 4B). Because it was envisioned that introducing Tyr, an amino acid particularly suitable for binding, at position 342 and the ability to diversify position 383 would both positively contribute to creating molecular recognition surfaces, the G342Y mutation was incorporated in the scaffold.

C. Phage and Yeast Display of STOFN3-1

Figure 5:
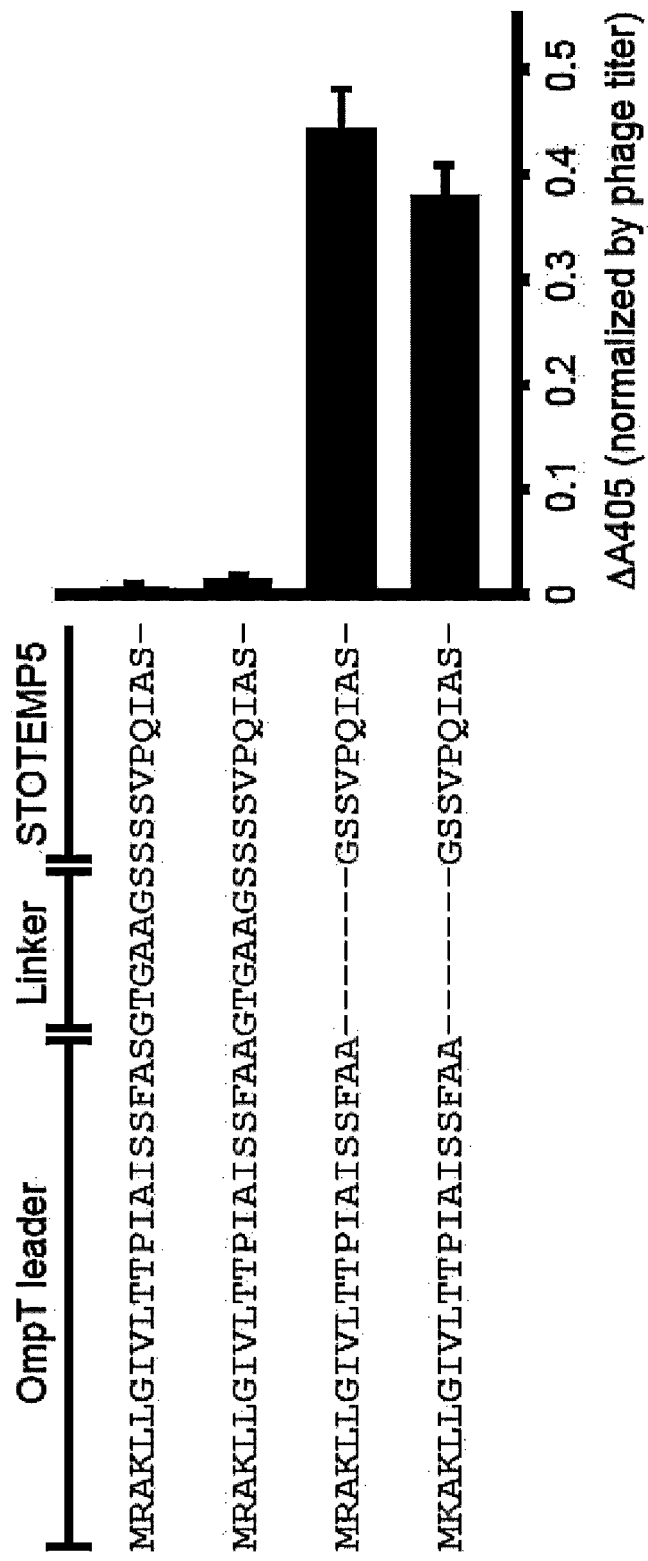
FIG. 5. Optimization of the signal sequence and linker length for the efficient display of STOTEMP5. The amino acid sequences corresponding to OmpT leader, linker and STOTEMP5 are shown. Mutated residues are colored in red. Deleted residues are denoted as dashes. The display of STOTEMP5 on phage particle was measured by phage ELISA using an anti-V5 tag antibody and a HRP conjugated anti-M13 phage antibody. The absorbance changes at 405 nm after the reaction with 1-step Ultra TMB ELISA for 10 min at 25° C. are shown. For this measurement, aliquots of 50 μL of phage particles with normalized titers of 2×106 cfu/mL pre-blocked in 0.5% BSA/TBS were added per well. Shown are SEQ ID NOS:55-58.

Efficient display of a scaffold on the phage particle is a prerequisite for efficient selection of binding proteins using phage display. Highly stable, rapidly folding proteins present challenges in phage display, because phage display requires that the displayed protein fused to a phage coat protein be translocated into the periplasm of *E. coli* and highly stable proteins are not efficiently translocated across the *E. coli* inner membrane using a conventional, posttranslational secretion signal such as OmpT. An elegant solution was to use a co-translational secretion signal sequence such as the DsbA signal. Different signal sequences were examined for robust display of STOFN3-1. For this examination, the variant of STOTEMP4 with K318V mutation (STOTEMP5) was used because this mutation was crucial to function as the enhancer domain of affinity clamp (see below). Unexpectedly, it was found that an OmpT-based system achieved high levels of display of STOFN3-1 on the phage after optimization of the signal sequence and a linker length between the signal and STOFN3-1 with use of the C-terminal domain of M13 pIII. Notably, a single point mutation of the signal peptidase cleavage site from -SSFA/S- found in the vector pET12a (where the slash denotes the cleavage site) to -SSFA/A- and no additional residues between this signal sequence and the first residue of STOFN3-1 were crucial for the efficient display (FIG. 5). Unlike in a previous report, the R2K mutation of the OmpT signal did not improve surface display. For yeast surface display of STOFN3-1, a standard Aga2-mediated system as previously described that robustly displayed the protein as confirmed using flow cytometric analysis was used (data not shown).

D. Design and Evaluation of Combinatorial Libraries

Following previous designs of combinatorial libraries of FNfn10, two distinct libraries were constructed. One library is "loop only" library where positions in the BC, DE, and FG loops are utilized (FIG. 6A). The other library is "side-and-loop library" where residues in the C strand (residues 346 and 348) and the D strand (residues 352-354, 356 and 358) as well as residues in the CD and FG loops are utilized (FIG. 6B). Both libraries used highly biased amino acid diversity that emphasized Tyr, Ser, Gly and excluded Cys and Met, similar to designs used for FNfn10 and Fab libraries. In both libraries, the length of the FG loop was varied. In the "loop only" library, the length of the BC loop was varied. In the "side-and-loop" library, the same design of diversification as previous studies was applied to residues in the C and D strands and the CD loop. For diversifying the position of W348 on the C-strand, two sets of oligos were used for each length of CD-loop (3, 4, and 5 residues). One contains a codon for Tryptophan and the other contains codons for Serine, Threonine, Asparagine and Tyrosine so that this position could be diversified to five amino acids. Both libraries were constructed using the STOTEMP5 as a template scaffold in the phage-display format described above with estimated numbers of independent sequences of 2.5× 109 and 1.7×109 for the loop only and side-and-loop libraries, respectively.

Figure 6C:
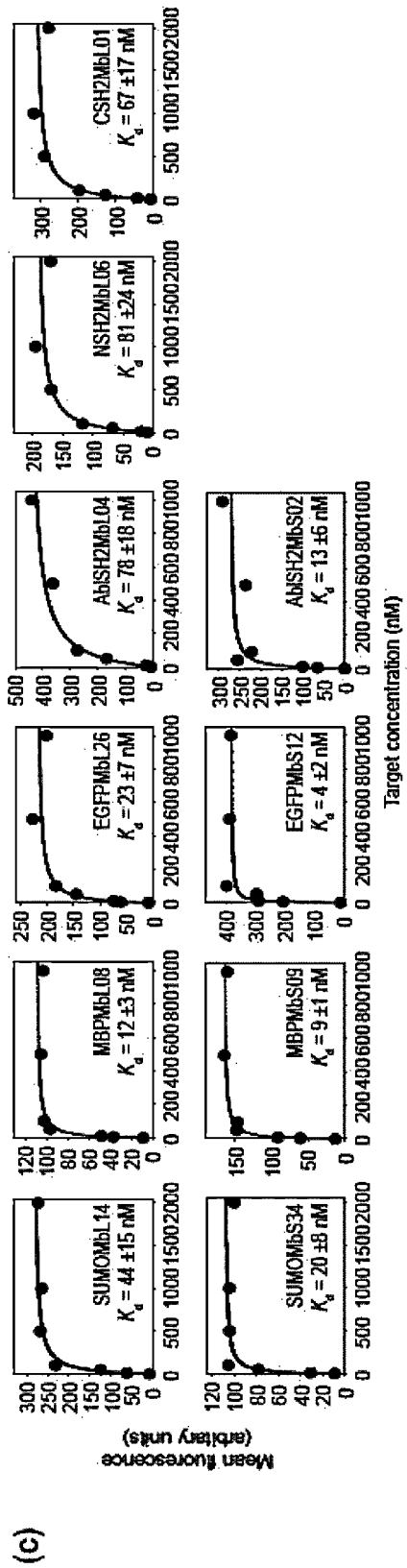

The inventors evaluated the performance of the two libraries using a total of six target proteins, yeast small ubiquitin-like modifier (ySUMO), maltose-binding protein (MBP), enhanced green fluorescent protein (GFP), Abl SH2, SHP2 N- and C-SH2 domains. For each combination of target and library, the inventors first enriched binding clones from the phage-display library, performed gene shuffling among the enriched population and identified high-affinity clones using yeast surface display. The inventors successfully generated binding proteins, called therMonobodies (thermophilic Monobodies), to ySUMO, MBP, EGFP and Abl SH2 from both libraries and SHP2 N- and C-SH2 from the loop-only library (FIG. 6A, 6B). Most therMonobodies had Kd values in the low nanomolar range as measured in the yeast-display format (FIG. 6C). Residues in the FG loop were mutated in almost all the therMonobodies derived from either library, suggesting the importance of residues in the FG loop in target binding. Only exceptions were tMb (ABLSH2_L03) and tMb(ABLSH2_S01) that had no mutations in the FG loop, suggesting the possibility of achieving high affinity without utilizing the FG loop. We identified loop lengths that were not encoded in our designs. tMb (SUMO_L03) had 13 residues in the FG oop, one residue longer than the longest design, and tMb(NSH2_L06) and tMb(NSH2_ L10) had four residues in the BC loop, one residue shorter than the shorted design. These sequences probably arose from errors in DNA synthesis and/or PCR errors, and their high functionality indicates that we could potentially expand the range of loop lengths in our library designs. For position 348, only Trp was selected, even though the position was diversified to a combination of five amino acids, Trp, Ser, Thr, Asn and Tyr. Subsequent mutation analysis showed that the replacement of W348 with Tyr or Ser destabilized STOTEMP5 by >18° C. and >25° C., respectively, indicating the importance of W348. In the crystal structure, the indole ring of W348 interacts with Y377 on the adjacent F-strand and also form a cation-7c interaction with K354 on the adjacent D-strand. Replacement of W348 may well disrupt or weaken these interactions, and this destabilization effect may lead to the low occurrence frequencies.

These results clearly demonstrate that the combinatorial libraries constructed on the newly developed scaffold and the selection strategy can generate high affinity binding proteins.

E. Biophysical Characterization of therMonobodies

Figure 7A:
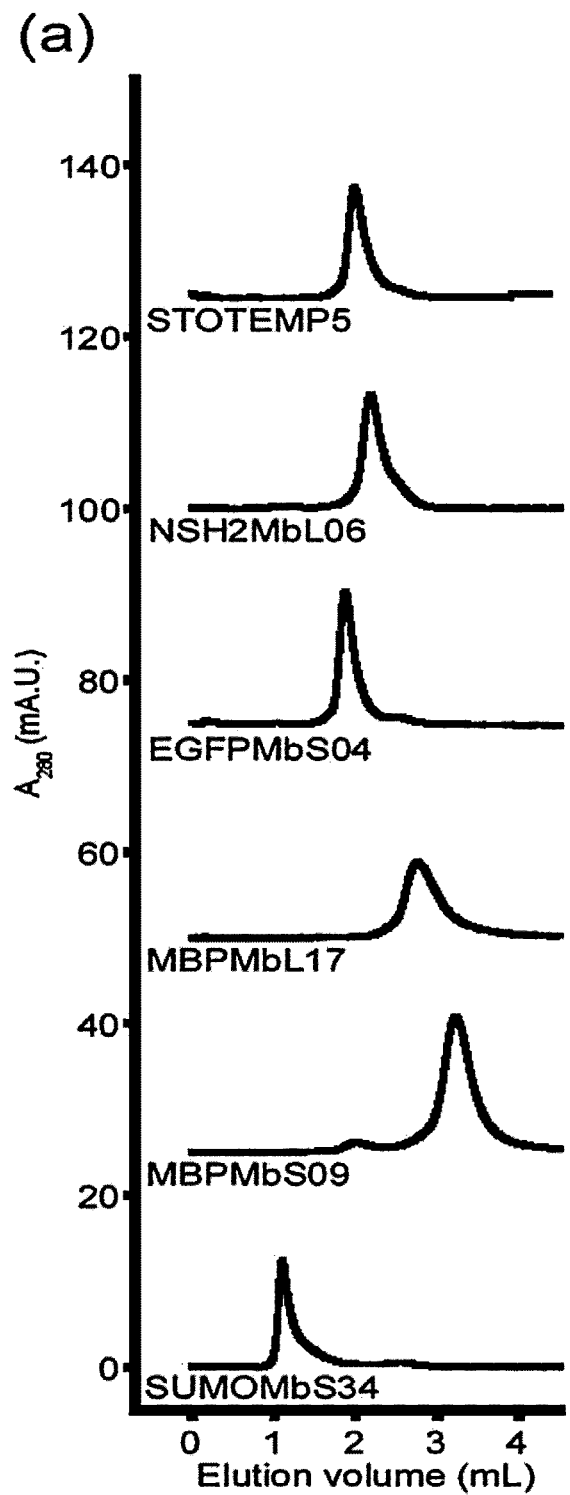
Figure 7B:
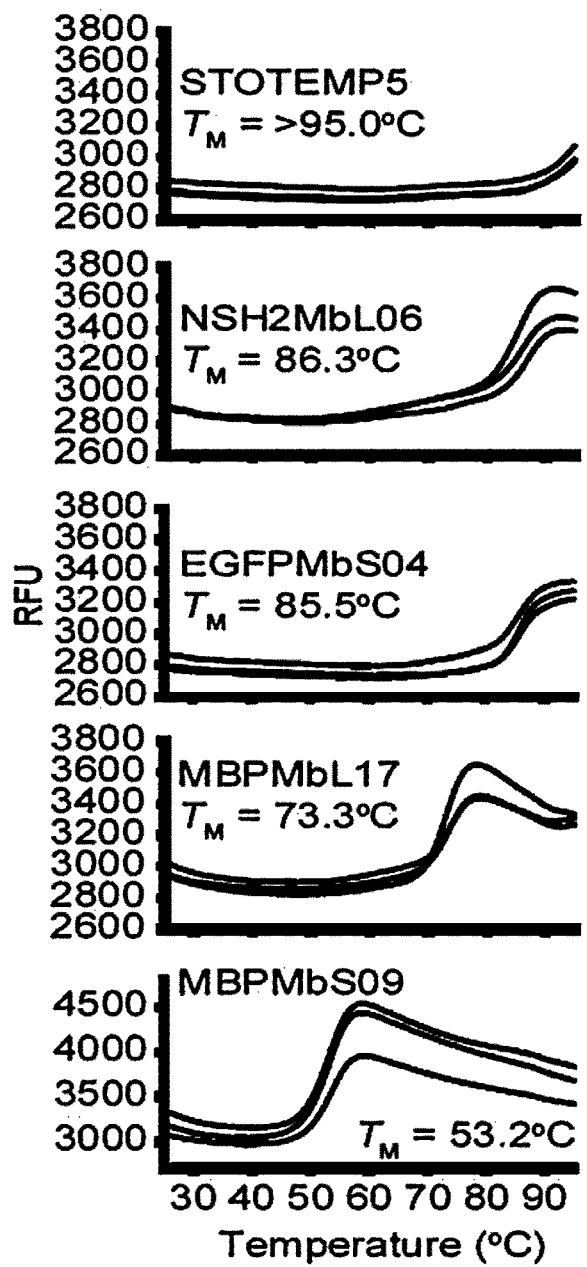

The inventors characterized the oligomerization state and thermal stability of purified therMonobodies (FIG. 7). Of 24 therMonobodies tested, 15 were predominantly monomeric as assayed using size-exclusion chromatography (SEC). Six eluted from the SEC as a monodispersed peak at the volume corresponding to a molecular weight much smaller than expected, suggesting that they were predominantly monomeric but weakly interacted with the column. The remaining three proteins eluted at the void volume, indicative of large aggregates. Thus, the vast majority (21/24) of these therMonobodies were produced as soluble, monomeric species. The thermal stability of the monomeric therMonobodies was assessed using DSF (FIG. 7B, C). The therMonobodies derived from the loop only library had a mean Tm value of 68±10° C. with the highest and lowest of 86.3 and 53.5° C., respectively. Those generated from the side-and-loop library had a mean Tm value of 59.2±11.3° C. with the highest and lowest of and 50.5° C., respectively. Interestingly, the most stable clones, tMb(NSH2_L06) and tMb(NSH2_L10), had four residues in the BC loop, which is one residue shorter than the designed range of the BC loop length. This finding suggests a new library design that better maintain the high stability of the underlying STOFN3-1 scaffold.

The highest Tm value of 86° C. and the lowest Tm value of 50° C. are both 13° C. higher than those of previously generated monobodies built from the FNfn10 scaffold (ref. Vazquez-Lombardi, 2015, Drug Discov Today). Thus, these results suggest that the therMonobodies system is better suited for generating thermostable binding proteins.

F. therMonobody Functions as the Enhancer Domain of Affinity Clamps

The affinity clamping technology involves connecting a FN3 domain to a peptide-binding domain (such as an interaction domain or another FN3 domain) and subsequent optimization of the FN3 domain via directed evolution so as to create clamshell architecture that "clamps" a target motif in the newly generated interface between the two domains. The enlarged ligand interaction interface relative to that afforded by either domain achieves high specificity and high affinity. In this context, the FN3 portion is termed as the enhancer domain. To determine whether therMonobody can be used as the enhancer domain for affinity clamping technology, the FNfn10-based monobody was replaced in an affinity clamp directed to a phosphotyrosine (pY)-containing peptide with a therMonobody. The pY-clamp consists of an engineered Grb2 SH2 domain linked, via short linker, to a FNfn10 monobody. STOFN3-1 was structurally aligned with the FNfn10 monobody segment in the pY-clamp, clamp(Ptpn11_pY580). Residues of the monobody segment that were located within 5A from the Grb2 SH2 domain or 6A from the target pY-peptide were grafted to the structurally equivalent positions of STOTEMP4 (FIG. 8A). Because V4 located in the N-terminal tail of the monobody segment participates in the interaction with the Grb2 SH2 domain in the pY-clamp, the inventors also prepared a construct in which structurally equivalent K318 of STOTEMP4 was mutated to Val.

The inventors first examined biophysical properties of the designed therMonobody segments of the designed pY-clamps in isolation, i.e. not linked to the engineered SH2 domain. The therMonobody segments with and without the K318V mutation were expressed as >50% of soluble proteins and showed monodispersed size-exclusion chromatography profiles with an elution time consistent with that of their parent templates. The Tm values obtained from DSF were 68.7 and 63.5° C. for the variants without and with K318V mutation, respectively, indicating that both variants retained high stability. Together with the results mentioned in the above section, these results demonstrate the high tolerance of therMonobody template to extensive mutations.

Next the inventors examined binding properties of the designed pY-clamps to the target pY-peptide (Ptpn11 pY580). A total of six constructs were tested by combining the presence and absence of the K318V mutation with linker lengths of 0, 2 and 5 amino acids between the Grb2 SH2 domain and the therMonobody segment. Two of them, with the K318V mutation and linker lengths of 2 or 5 residues showed significantly higher binding to the pY-peptide than the original Grb2 SH2 domain alone (FIG. 8B), with KD values of 156±42 and 121±21 nM for the 2- and 5-residue linkers, respectively (FIG. 8C). For comparison, clamp (Ptpn11_pY580) with the optimized enhancer domain based on FNfn10 had a 6 amino acids linker between the Grb2 SH2 domain and the monobody segment and a KD value of 2.5 nM. Although the affinity of the therMonobody versions of the pY-clamp was lower, these results clearly indicates that therMonobody can readily be used as a building block for generating affinity clamps.

Example 2: Hyperthermophilic Fn3 Domain from *Pyrococcus horikoshii* Ot3

Figure 9:
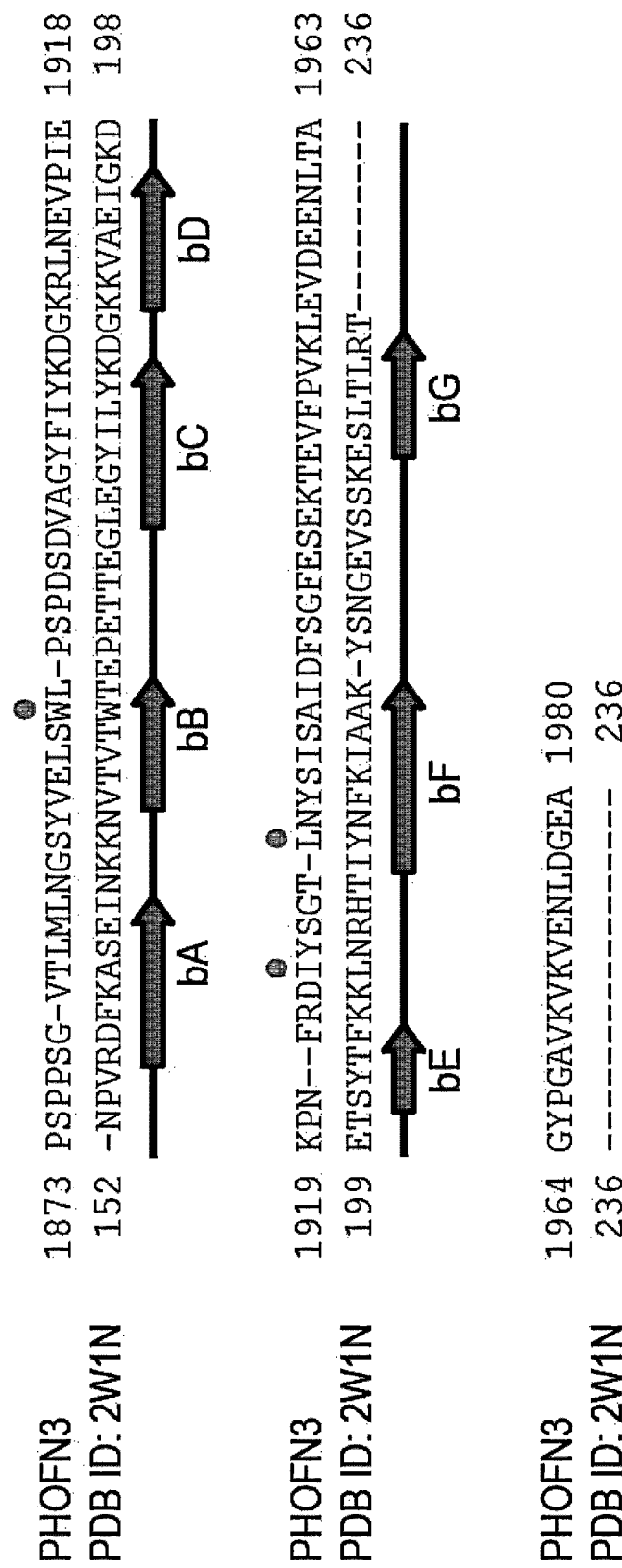
FIG. 9. Sequence alignment of predicted PHOFN3 and the bacterial FN3 domain in *Clostridium perfringens* Glycoside Hydrolase Gh84c (PDB ID: 2W1N). Gaps are denoted as dashes. The bacterial FN3 domain shows the sequence identities of 25% to PHOFN3, which is the highest among PDB entries. The locations of beta-strands in the bacterial FN3 domain are shown as the green arrows. Red dots indicate the highly conserved residues of FN3 domains reported by Main et al. and Dickinson et al. (Main et al., 1992; Dickinson et al., 1994). Shown in FIG. 9 are SEQ ID NOS:94-98.

The inventors utilized the SMART database to explore FN3 domains from hyperthermophiles. The database predicted many FN3 domains in hyperthermophilic archaea and bacteria such as *Thermococcus kodakaraensis, Sulfolobus tokodaii, Pyrococcus horikoshii* and *Thermotoga lettingae*. Predicted domains that were shorter than the length of the shortest FN3 domains that had been structurally characterized (75 amino acids) were first eliminated. Then, a FN3 domain in the sequence of putative uncharacterized protein PH0954 from the hyperthermophilic archaeon *Pyrococcus horikoshii* OT3, termed PHOFN3 was chosen as the candidate protein, because of its detectably homology to a bacterial FN3 domain in the *Clostridium Perfringens* Glycoside Hydrolase Gh84c whose FN3 fold has been experimentally confirmed (PDB ID: 2W1N). The SMART database predicted PHOFN3 with 108 (P1873-A1980) amino acid residues, but the C-terminal 26 residues (E1955-A1980) did not have detectable homology to the sequence of the bacterial homologue (FIG. 9).

Figure 10:
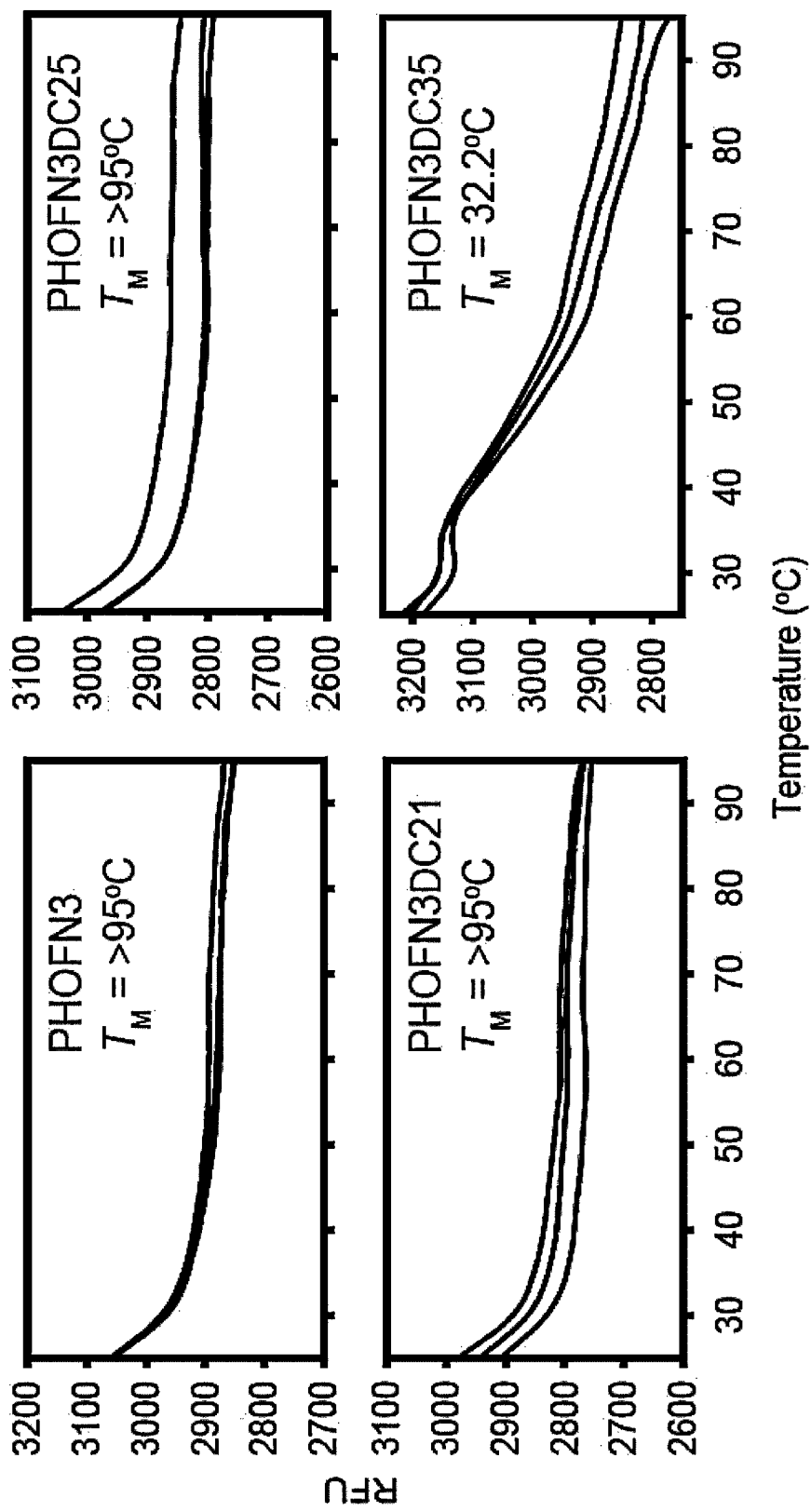
FIG. 10. Thermal stability of purified PHOFN3 and its truncated variants monitored by DSF. Triplicate measurements are shown for each sample. The melting curves were measured by heating the samples at a rate of 0.5° C. per 30 seconds. Only PHOFN3□C35 exhibited an inflection point indicative of thermal denaturation. The TM value for PHOFN3□C35 is the mean of the inflection points from triplicates.

In order to confirm whether the C-terminal extended region is a part of the core structure of PHOFN3, the inventors constructed expression vectors for different segments of PHOFN3 with the same N-terminus but with different truncations from the C-terminus, PHOFN3 (P1873-A1980), PHOFN3ΔC21 (P1873-E1959), PHOFN3ΔC25 (P1873-E1955) and PHOFN3ΔC35 (P1873-E1945), and analyzed their soluble expressions in *E. coli* and thermal stabilities. It was found that PHOFN3, PHOFN3ΔC21 and PHOFN3ΔC25 were robustly produced in *E. coli* as soluble proteins that were predominantly monomeric. Melting temperatures obtained by differential scanning fluorimetry (DSF) were >95° C. for PHOFN3, PHOFN3ΔC21 and PHOFN3ΔC25 at pH 7.4, confirming that they were highly thermostable proteins (FIG. 10). These results suggested that the C-terminal extended region, which was not aligned with the bacterial homologue, was not a part of the core structure of PHOFN3. In contrast, PHOFN3ΔC35 was expressed mostly as insoluble proteins and the melting temperature was 32.2° C. at pH 7.4 (FIG. 10), suggesting that the region of K1946-E1955 was important for folding a proper structure and for thermal stability as the region was aligned with the last β-strand (G strand) of the bacterial homologue.

Figure 11:
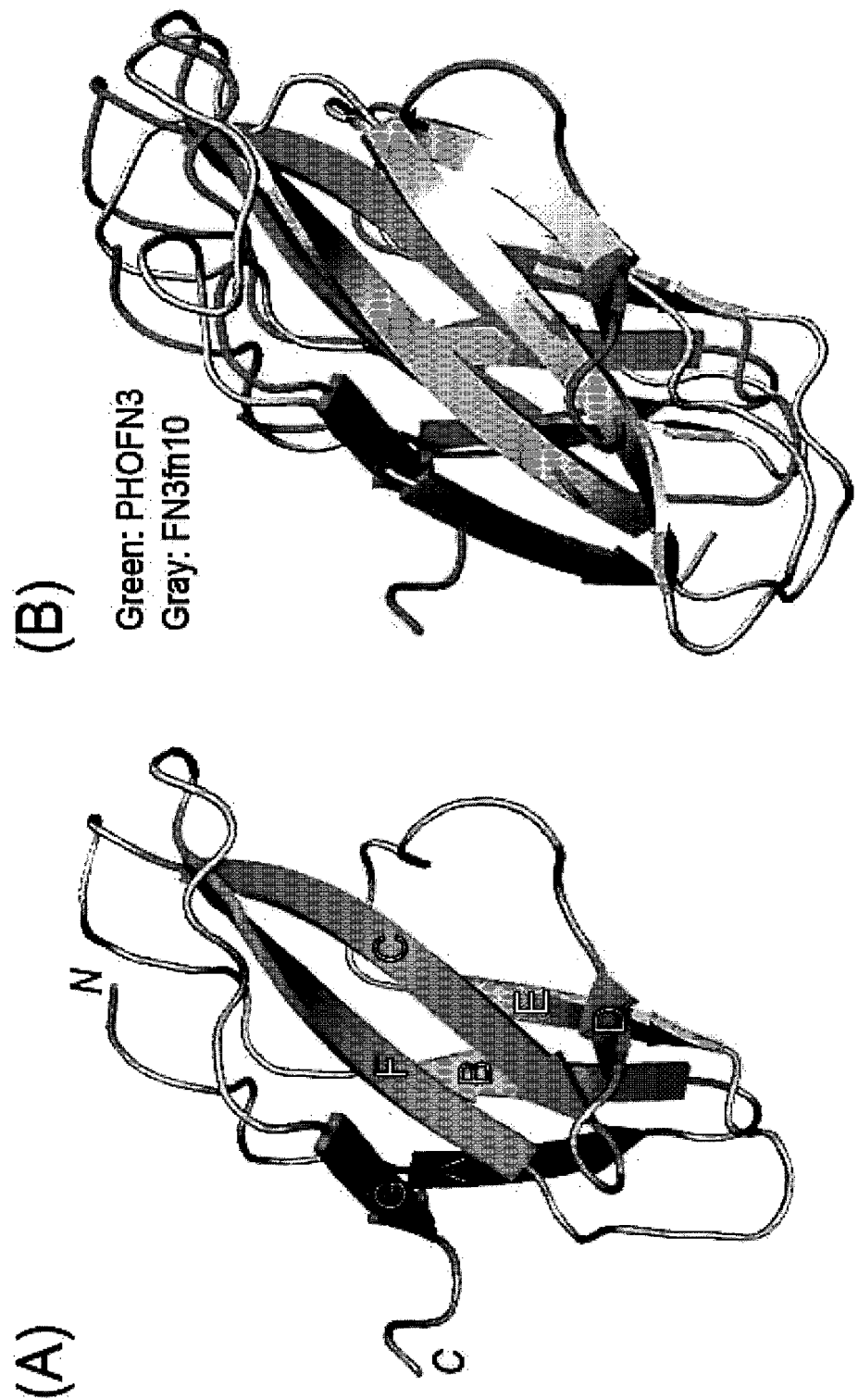
FIG. 11A-B. A) The crystal structures of SeMet-labeled PHOFN3ΔC25. The seven β-strands are colored and labeled A-G. N- and C-terminus are labeled. B) Superposition of PHOFN3ΔC25 and FN3fn10 (PDBID: 1FNA). PHOFN3ΔC25 and FN3fn10 are colored green and gray, respectively.

To confirm that PHOFN3 had the FN3 fold, the inventors determined the crystal structure of PHOFN3ΔC25 at 1.7 Å resolution with Se-Met labeled at M1882 and I1905M. The PHOFN3ΔC25 segment indeed adopts the FN3 fold consisting of seven anti-parallel β-strands and six loops (FIG. 11A). Superposition with the FN3fn10 (PDB ID: 1FNA), the most well characterized FN3 domain, demonstrated that the structure of the segment is highly similar to FN3fn10 with an average RMSD value of 2.2 Å for aligned backbone Cα atoms excluding residues in loops (FIG. 11B). Figure E shows the schematic drawing of the amino acid sequence of PHOFN3ΔC25 in its secondary structure context.

Figure 12:
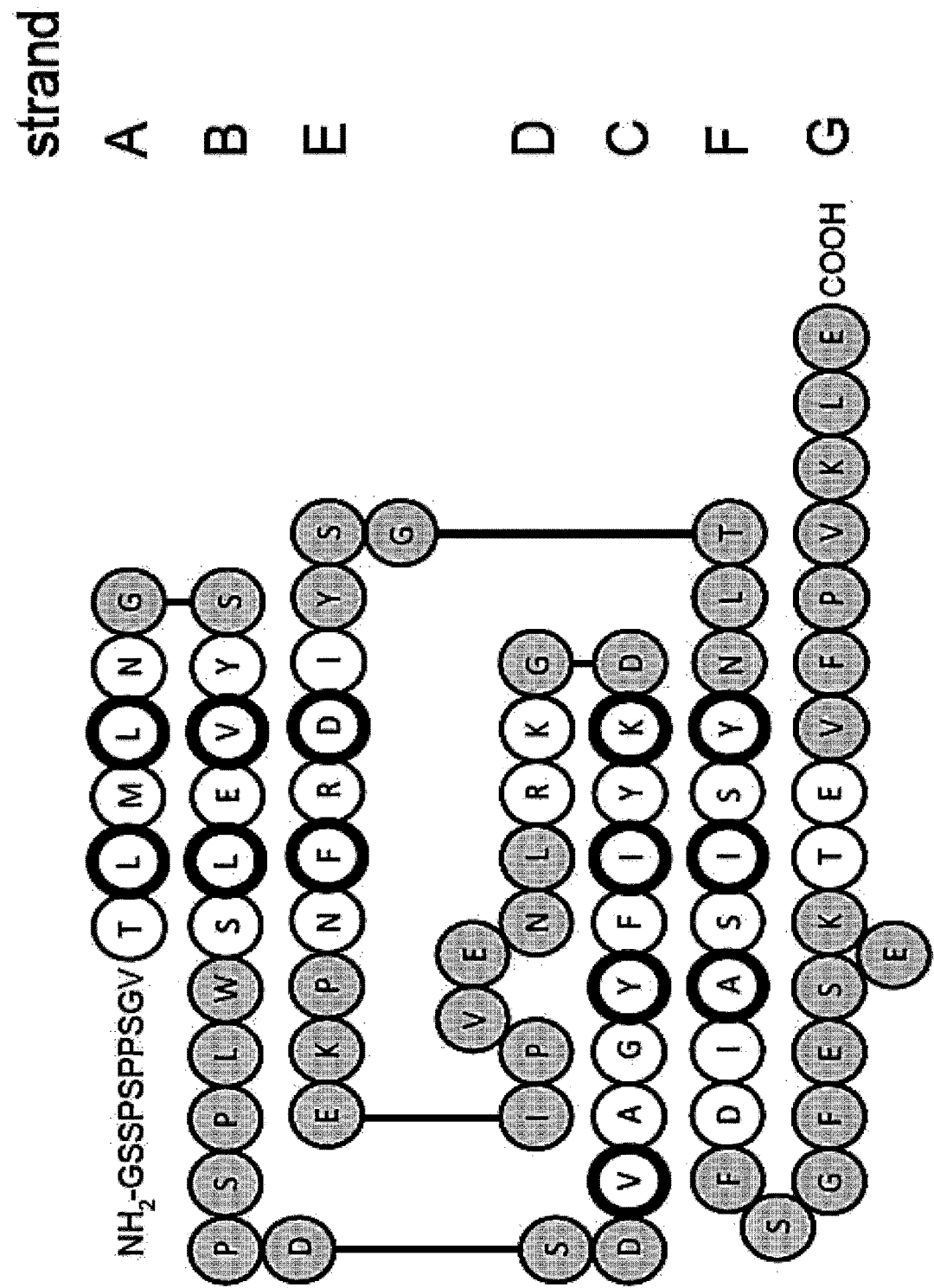
FIG. 12. Schematic drawing of the amino acid sequence of PHOFN3ΔC25 in its secondary structure context. Loop residues as assigned by the program DSSP are shown in yellow. Residues of the β-strands whose side chain forms the hydrophobic core are enclosed in circles with thicker ring.
Figure 13:
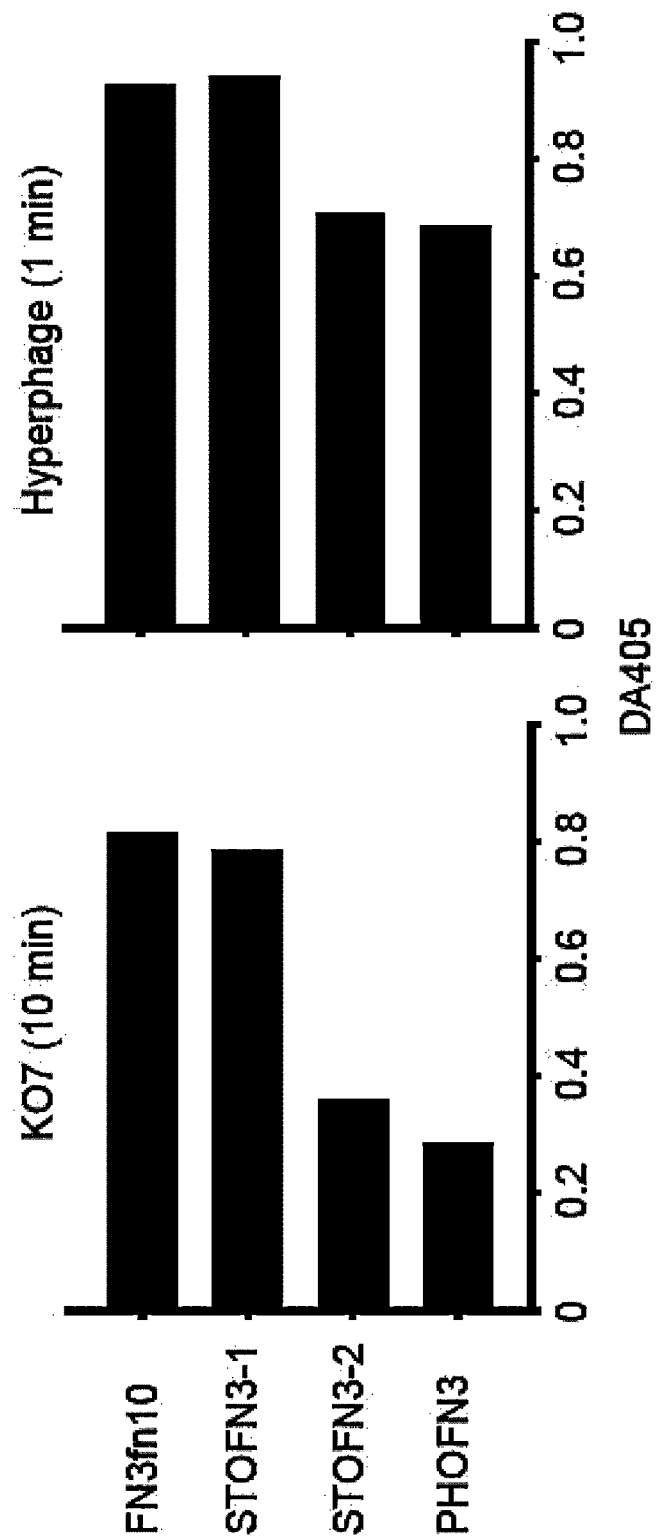
FIG. 13. Phage ELISA analysis for surface display of PHOFN3 on phage particles. Binding of phage particles to an anti-V5 tag antibody. The V5 tag is located in the linker between PHOFN3 and the phage coat protein, P3, in the phage display vector. The absorbance changes at 405 nm after the HRP reaction with 1-step Ultra TMB ELISA for 10 min for phages produced with the M13KO7 helper phage or 1 min for hyperphage-produced phages are shown. For these measurements, 50 µL of 0.5% BSA/TBS containing 2.3×106 cfu/mL M13KO7-produced phages or 7.4×106 cfu/mL hyperphage-produced phages were added to each well and bound phages were detected with a HRP conjugated anti-M13 phage antibody.

Phage display of PHOFN3. A vector for phage display of PHOFN3 (without C-terminal deletion, P1873-A1980) was constructed based on the previously reported DsbA-based vector containing the V5 tag sequence for display detection (Wojcik et al., NSMB). Phage particles were produced using helper phage, M13KO7 or hyperphage, and the display of PHOFN3 on phage particles was examined by phage ELISA using an anti-V5 tag antibody, a HRP conjugated anti-M13 phage antibody and 1-step Ultra TMB ELISA (Thermo Scientific). The absorbance changes at 405 nm after the HRP reaction for 10 min for M13KO7-produced phages or 1 min for hyperphage-produced phages are shown in FIG. 12. FIG. 13 shows the significant levels of display of PHOFN3 on phage particles. The phage ELISA signals for PHOFN3 with M13KO7 and hyperphage were lower than those for FN3fn10 only by 2.9 and 1.3-folds, respectively, strongly suggesting that a combinatorial library similar to those for FNfn10 can be constructed using phage display from which novel binding proteins can be identified.

Although certain embodiments have been described above with a certain degree of particularity, or with reference to one or more individual embodiments, those skilled in the art could make numerous alterations to the disclosed embodiments without departing from the scope of this invention. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments. Any reference to a patent publication or other publication is a herein a specific incorporation by reference of the disclosure of that publication. The claims are not to be interpreted as including means-plus- or step-plus-function limitations, unless such a limitation is explicitly recited in a given claim using the phrase(s) "means for" or "step for," respectively.

The invention claimed is:

1. A polypeptide comprising a variant fibronectin type III (FN3) domain from *Sulfolobus tokodaii* comprising a first region comprising amino acids 1-12 of SEQ ID NO:1 with P1S, P2S, and P3S substitutions and optionally a K4V substitution, a second region comprising amino acids 13-16 of SEQ ID NO:1 with a substitution of N14P, a third region comprising amino acids 54-60 of SEQ ID NO:1 with a substitution of D58P, and a fourth region comprising amino acids 81-84 of SEQ ID NO:1 with an insertion of the amino acids PSS after amino acid 84; wherein the polypeptide is a fusion protein comprising the variant FN3 domain.

2. The polypeptide of claim 1, wherein the fusion protein comprises the variant FN3 domain fused to an interaction domain comprising one or more of a PDZ, WW, SH2, PTB, SH3, Bromo, Chromo, PHD, Polo-box and FHA domain.

3. A polynucleotide encoding the polypeptide of claim 1.

4. A kit comprising a plurality of polypeptides as described in claim 1.

5. A method of making a polypeptide or polypeptide library comprising expressing the polynucleotide of claim 3 in a host cell.

6. The polypeptide of claim 1, wherein the polypeptide comprises one or more amino acid substitutions or insertions relative to SEQ ID NO:1 and outside of the specifically defined amino acids and amino acid substitutions of the first, second, third, and fourth regions.

7. A polypeptide library comprising a plurality of modified FN3 domain polypeptides according to claim 6.

8. The polypeptide of claim 1, wherein the polypeptide comprises a substitution at the amino acid position corresponding to amino acid 28 of SEQ ID NO: 1.

9. The polypeptide of claim 8, wherein the substitution corresponding to amino acid position 28 of SEQ ID NO: 1 is with a tyrosine.

10. The polypeptide of claim 1, wherein the polypeptide is recombinant.

11. The polypeptide of claim 1, wherein the polypeptide further comprises a signaling moiety and wherein the signaling moiety comprises a dye, a quencher, a reporter protein, or a quantum dot.

12. The polypeptide of claim 1, wherein the polypeptide is synthetic.

* * * * *

UNITED STATES PATENT AND TRADEMARK OFFICE
CERTIFICATE OF CORRECTION

PATENT NO. : 12,312,392 B2
APPLICATION NO. : 18/312100
DATED : May 27, 2025
INVENTOR(S) : Shohei Koide et al.

Page 1 of 1

It is certified that error appears in the above-identified patent and that said Letters Patent is hereby corrected as shown below:

In the Claims

Column 57, Line 19:
Delete "PIS" and replace with --P1S--.

Signed and Sealed this
Eighth Day of July, 2025

Coke Morgan Stewart
*Acting Director of the United States Patent and Trademark Office*